US009057072B2

(12) United States Patent
Swennen et al.

(10) Patent No.: US 9,057,072 B2
(45) Date of Patent: Jun. 16, 2015

(54) BANANA PROMOTERS

(75) Inventors: Rony Swennen, Blanden (BE); Laszlo Sagi, Szodliget (HU); Serge Remy, Linden (BE); Liesbet Smeijers, Vorst (BE); Ilse Constant Marie Wiame, Heemstede (NL)

(73) Assignees: KATHOLIEKE UNIVERSITEIT LEUVEN, K.U. LEUVEN R&D, Leuven (BE); INVERENSIONES EUROPAS NICARAGUENSES SA, Ciudad Panama (PA)

( * ) Notice: Subject to any disclaimer, the term of this patent is extended or adjusted under 35 U.S.C. 154(b) by 401 days.

(21) Appl. No.: 13/511,057

(22) PCT Filed: Nov. 24, 2010

(86) PCT No.: PCT/EP2010/068068
§ 371 (c)(1),
(2), (4) Date: May 21, 2012

(87) PCT Pub. No.: WO2011/064224
PCT Pub. Date: Jun. 3, 2011

(65) Prior Publication Data
US 2012/0295011 A1  Nov. 22, 2012

Related U.S. Application Data

(60) Provisional application No. 61/281,874, filed on Nov. 24, 2009.

(51) Int. Cl.
*C12N 15/82* (2006.01)
*C07H 21/04* (2006.01)

(52) U.S. Cl.
CPC .................................. *C12N 15/8216* (2013.01)

(58) Field of Classification Search
None
See application file for complete search history.

(56) References Cited

U.S. PATENT DOCUMENTS 6,441,273 B1 *  8/2002  Aldwinckle et al. .......... 800/278

FOREIGN PATENT DOCUMENTS

| WO | WO 93/07279 | 4/1993 |
| WO | WO 97/38106 | 10/1997 |
| WO | WO 00/56863 | 9/2000 |

OTHER PUBLICATIONS

Chen et al., Environ Exper Bot 66(1):31-37 (2009).*
Santos et al., BMC Plant Biology 9:77 (2009).*
Potenza_In Vitro Cell Dev Biol Plant_40_1_2004.*
Donald_EMBO J_9_1717_1990.*
Dolferus_Plant Phys_105_1075_1994.*
Kim_Plant Mol Biol_24_105_1994.*
Chen, et al. "Expression of PAL and HSPS in Fresh-cut Banana Fruit," *Environmental and Experimental Botany*, vol. 66, No. 1, pp. 31-37, Apr. 2009.
Choudhury, et al. "Differential Transcriptional Regulation of Banana Sucrose Phosphate Synthase Gene in Response to Ethylene, Auxin, Wounding, Low Temperature and Different Photoperiods During Fruit Ripening and Functional Analysis of Banana SPS Gene Promoter," *Planta*, vol. 229, No. 1, pp. 207-223, Dec. 2008.
Santos, et al. "Characterization and Isolation of a T-DNA Tagged Banana Promoter Active During In Vitro Culture and Low Temperature Stress," *BMC Plant Biology*, vol. 9, pp. 1-15, Jun. 2009.
Wang, et al. "Cloning and Expression Analysis of Phenylalanine Ammonia-lyase in Relational to Chilling Tolerance in Harvested Banana Fruit," *Postharvest Biology and Technology*, vol. 44, No. 1, pp. 34-41, Mar. 8, 2007.
International Search Report dated Apr. 14, 2011 issued to international application No. PCT/EP2010/068068.

* cited by examiner

*Primary Examiner* — Medina A Ibrahim
*Assistant Examiner* — Russell Boggs
(74) *Attorney, Agent, or Firm* — Knobbe, Martens, Olson & Bear LLP

(57) ABSTRACT

This invention provides promoter sequences that are useful for modulating transcription of a desired polynucleotide and/or in the construction of recombinant genes for plant transformation to enable expression of foreign or endogenous coding sequences in plants. The promoters are functional in a both monocotyledonous and dicotyledonous plant species and are active in a wide range of vegetative or generative plant organs. The invention also provides a polynucleotide construct comprising a promoter of the invention operably linked to a foreign or endogenous polynucleotide encoding a protein of interest or a transcript capable of modulating expression of a target gene. The invention is further concerned with transformed plant cells, as well as differentiated plants, plant parts, plant tissues or plant seeds containing the construct.

12 Claims, 11 Drawing Sheets

BANANA PROMOTERS

CROSS-REFERENCE TO RELATED APPLICATIONS

This application is the U.S. National Phase under 35 U.S.C. §371 of International Application PCT/EP2010/068068, filed Nov. 24, 2010, which claims priority to U.S. Provisional Application No. 61/281,874, filed Nov. 24, 2009.

FIELD OF THE INVENTION

This invention provides promoter sequences that are useful for modulating transcription of a desired polynucleotide and/or in the construction of recombinant genes for plant transformation to enable expression of foreign or endogenous coding sequences in monocotyledonous and dicotyledonous plants. The invention also relates to polynucleotide constructs comprising a promoter of the invention operably linked to a foreign or endogenous polynucleotide encoding a protein of interest or a transcript capable of modulating expression of a target gene. The invention is further concerned with transformed plant cells, as well as transformed plants and progeny thereof, plant parts or reproductive material of said plants, containing the construct.

BACKGROUND OF THE INVENTION

A primary goal of genetic engineering is to obtain plants having improved characteristics or traits. Many different types of characteristics or traits are considered advantageous, but those of particular importance include resistance to plant diseases, resistance to viruses or insects and resistance to herbicides. Other advantageous characteristics or traits include tolerance to cold or soil salinity, enhanced stability or shelf life of the ultimate consumer product obtained from a plant, or improvement in the nutritional value of edible portions of a plant.

Recent advances in genetic engineering have enabled the incorporation of a selected gene (or genes) into plant cells to impart a desired quality (or qualities) to a plant of interest. The selected gene (or genes) may be derived from a source different from the plant of interest or may be native to the desired plant, but either engineered to have different or improved qualities or confer altered properties to the plant upon modified expression level or pattern. Expression of such a gene (or genes) in cells of the regenerated plant confers the new plant trait or characteristic.

In order to render a new gene functional in a genome, the three main components of a gene (as a structural and functional unit in a broad sense) have to be considered. In addition to the coding sequence (or the gene sensu stricto), which encodes a polypeptide that will execute the gene's function, the immediately upstream as well as downstream regulatory regions that are required for controlling the expression of the coding sequence in space and time needs to be present and in the proper location. The upstream (also called 5') regulatory region contains the promoter sequence, which is not transcribed into RNA and the so-called 5' untranslated region (UTR) or leader sequence, which is transcribed into RNA but not translated into a protein. Of these two groups of sequences, the promoter plays the most pronounced role because it serves as docking place for a number of DNA-binding and DNA-bending transcription factor proteins as well as for the whole transcription machinery including the DNA-dependent RNA polymerase holoenzyme and other cofactors. In comparison, the 3' UTR has a minor, modulating role in regulating gene expression.

The efficiency of gene expression is governed largely by the promoter used to express the gene. A promoter is typically a DNA sequence that directs the cellular machinery of a plant to produce (transcribe) RNA (transcript) from a contiguous transcribable region downstream (3') of the promoter. The promoter influences the rate at which the transcript of the gene is made. Assuming the transcript includes a coding region with appropriate translational signals, the promoter also influences the rate at which the resultant protein product of the gene is produced. Promoter activity also can depend on the presence of several other cis-acting regulatory elements which, in conjunction with cellular factors, determine strength, specificity, and transcription initiation site (for a review, see Zawel and Reinberg, 1992, Curr. Opin. Cell Biol. 4: 488).

It has been shown that certain promoters are able to direct RNA synthesis at a higher rate relative to other promoters. These are called "strong promoters". Certain other promoters have been shown to direct RNA production at higher levels only in particular types of cells or tissues and are often referred to as "tissue-specific promoters". "Regulated or inducible promoters" control gene expression in certain organs, tissues and cell types during a specific developmental phase(s), or are activated by a defined chemical or environmental signal, respectively. Promoters that are capable of directing RNA production in many or all tissues of a plant are called "constitutive promoters". Examples of constitutive promoters in higher plants include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill. Thus, expression of a gene (or genes) introduced into a cell, particularly a plant cell, may potentially be controlled by identifying and using a promoter with the desired characteristics.

For many purposes in plant genetic engineering, a strong nearly constitutive promoter is required to ensure sufficient expression throughout the plant. Several strong nearly constitutive promoters for the genetic manipulation of plants are known in the art (e.g. the 35S promoter of cauliflower mosaic virus—see U.S. Pat. No. 5,352,605, U.S. Pat. No. 5,164,316, U.S. Pat. No. 5,196,525. U.S. Pat. No. 5,322,938 and U.S. Pat. No. 5,359,142). However, having more than one nearly constitutive promoter can be very useful when several different genes need to be expressed in plants (gene pyramiding). It has been frequently observed that gene silencing occurs in plants transformed with several genes that are each regulated by the same promoter (Flavell, *Proc. Natl. Acad. Sci. USA* 91, 3490-3496 [1994]; Finnegan and McElroy, *Bio/Technology* 12, 883-888 [1994]; Matzke et al., *Mol. Gen. Genet.* 244, 219-229 [1994]: Park et al., *The Plant Journal* 9, 183-194 [1996]). This problem is thought to be caused by homology-based genetic interference and can be avoided using different promoters for gene pyramiding. In addition, new promoters are also needed in the context of the intragenic concept, i.e. the transfer of a DNA sequence into a plant genome which has its documented origin from within the same or a sexually compatible plant species. In addition, there are possible scenarios, when it is preferable to introduce the new (intra)gene under a different promoter, but still from the same (or a sexually compatible) species, rather than with its own promoter. One of these scenarios is the situation when invading pathogens manage to down-regulate promoters of genes acting in the host's defense machinery. In this case, it is desirable that the gene to be transferred is fused to another promoter of a similar or even different gene that is not affected by the pathogen, which ensures that the gene will be correctly expressed even under adverse conditions.

SUMMARY OF THE INVENTION

It is an object of the present invention to provide isolated polynucleotide sequences that comprise promoters and promoter elements from plants, especially from banana (*Musa* sp.) PAL genes. Said promoters and promoter elements are operative in plant cells and can be used in genetic engineering for regulation of gene expression.

In a first aspect, the invention provides polynucleotide sequences with promoter activity in a plant cell. More particularly, the invention provides isolated polynucleotides having plant promoter activity, wherein the polynucleotide comprises a polynucleotide having nucleotide sequence SEQ ID NO:4, or a biologically active fragment or homologue thereof having a nucleotide sequence with at least 70% sequence identity with SEQ ID NO:4.

Preferably, the homologue comprises a polynucleotide having a nucleotide sequence with at least 70%, preferably at least 80% or 85%, more preferably 90%, most preferably at least 95% or 97% sequence identity with SEQ ID NO:4 after best alignment of the homologue or variant polynucleotide with SEQ ID NO:4 and with exclusion of gap positions having a gap length of at least 5 nucleotides, preferably at least 6, 7, 8, 9 or 10 nucleotides.

In a particular embodiment, the polynucleotides having plant promoter activity comprise a polynucleotide having nucleotide sequence of SEQ ID NO:1, SEQ ID NO:2, SEQ ID NO:3 or SEQ ID NO:4.

In a further embodiment of the invention, there is provided an isolated promoter polynucleotide sequence operative in a plant cell, said promoter sequence comprising
(i) nucleotide sequence SEQ ID NO:1 or SEQ ID NO:2; or
(ii) a truncated promoter-active fragment of the isolated polynucleotide of (i); or
(iii) a polynucleotide sequence which is a homologue or a variant of (i) or (ii);

Preferably, said homologue or variant comprise a polynucleotide having a nucleotide sequence with at least 70%, preferably at least 80% or 85%, more preferably 90%, most preferably at least 95% or 97% sequence identity with SEQ ID NO:1 or SEQ ID NO:2 or one or more segments thereof that are longer than 100 contiguous nucleotides, preferably longer than 150 or 200 contiguous nucleotides, most preferably longer than 300 contiguous nucleotides. Alternatively, said homologue or variant comprises a polynucleotide which hybridises under stringent conditions to (the complement of) SEQ ID NO:1 or SEQ ID NO:2 or a truncated promoter-active fragment thereof.

Preferably, said truncated promoter-active fragment comprises SEQ ID NO:3 or SEQ ID NO:4 or a variant thereof having a polynucleotide which hybridises under stringent conditions to (the complement of) SEQ ID NO:3 or SEQ ID NO:4.

Preferably, said promoters comprise one or more elements are capable of serving as or fulfilling the function of, for example, a TATA box, a PAL box, a CAAT box, a GATA box, an AS1 element, MYB/WRE3 element, a translation start signal, a polymerase binding site, an initiator site, a transcription factor binding site, an enhancer, an inverted repeat, a locus control region, or a scaffold/matrix attachment region.

It is a further object of the present invention to provide polynucleotide constructs, preferably DNA constructs, or expression vectors comprising said isolated polynucleotide sequence with plant promoter activity, or a variant or homologue thereof or biologically active fragment thereof operatively linked to a second, heterologous polynucleotide sequence that is a coding sequence encoding for an RNA and/or a polypeptide or that is a regulatory sequence. Yet another object of the present invention provides vectors comprising said polynucleotide construct of the present invention.

It is another object of the present invention to provide transformed host cells, preferably transformed plant cells comprising said polynucleotide constructs comprising the polynucleotide sequence with plant promoter activity according to the present invention. Preferably, said promoter polynucleotide and/or said polynucleotide construct of the present invention is stably incorporated in the genome of said plant cells. The invention also contemplates methods for producing transformed plant cells, comprising introducing into regenerable plant cells a polynucleotide construct according to the present invention so as to yield transformed plant cells and identifying or selecting transformed plant cells. Said transformed plant cells can be monocot or dicot plant cells, preferably a plant cell from a plant species belonging to the Musaceae, Poaceae, Brassicaceae or Solanaceae, or a plant cell from soybean, sunflower, sugar beet, alfalfa, peanuts, cotton, coffee, coconut, pineapple or citrus fruits. According to particular embodiments of the invention, the plant is a Musaceae Plant, more particularly a banana.

In particular embodiments of the present invention, said transformed plant cells are capable of regenerating into a plant. The invention further contemplates methods for producing transgenic plants, comprising introducing a polynucleotide construct according to the present invention into regenerable plant cells so as to yield regenerable transformed cells, identifying or selecting one or a population of transformed plant cells, and regenerating a transgenic plant from said cell or cell population.

Another object of the present invention provides transformed plants or plant parts, plant tissue or reproductive material of a plant, wherein the transformed plants or plant parts, tissue or reproductive material comprises the plant cells according to the invention, comprising said polynucleotide constructs of the present invention. The invention also provides fruits, seeds and progeny plants or parts thereof derived from said transgenic plants.

In a further aspect of the present invention, there is provided methods of expressing a product in a plant cell or in a plant, said method comprising introducing the polynucleotide construct of the present invention into cells of a plant, wherein the coding sequence of the construct or RNA transcript thereof encodes said product.

In yet another aspect the invention provides processed food products, comprising the polynucleotide constructs described herein.

DETAILED DESCRIPTION

Legends to the Figures

Figure 4:
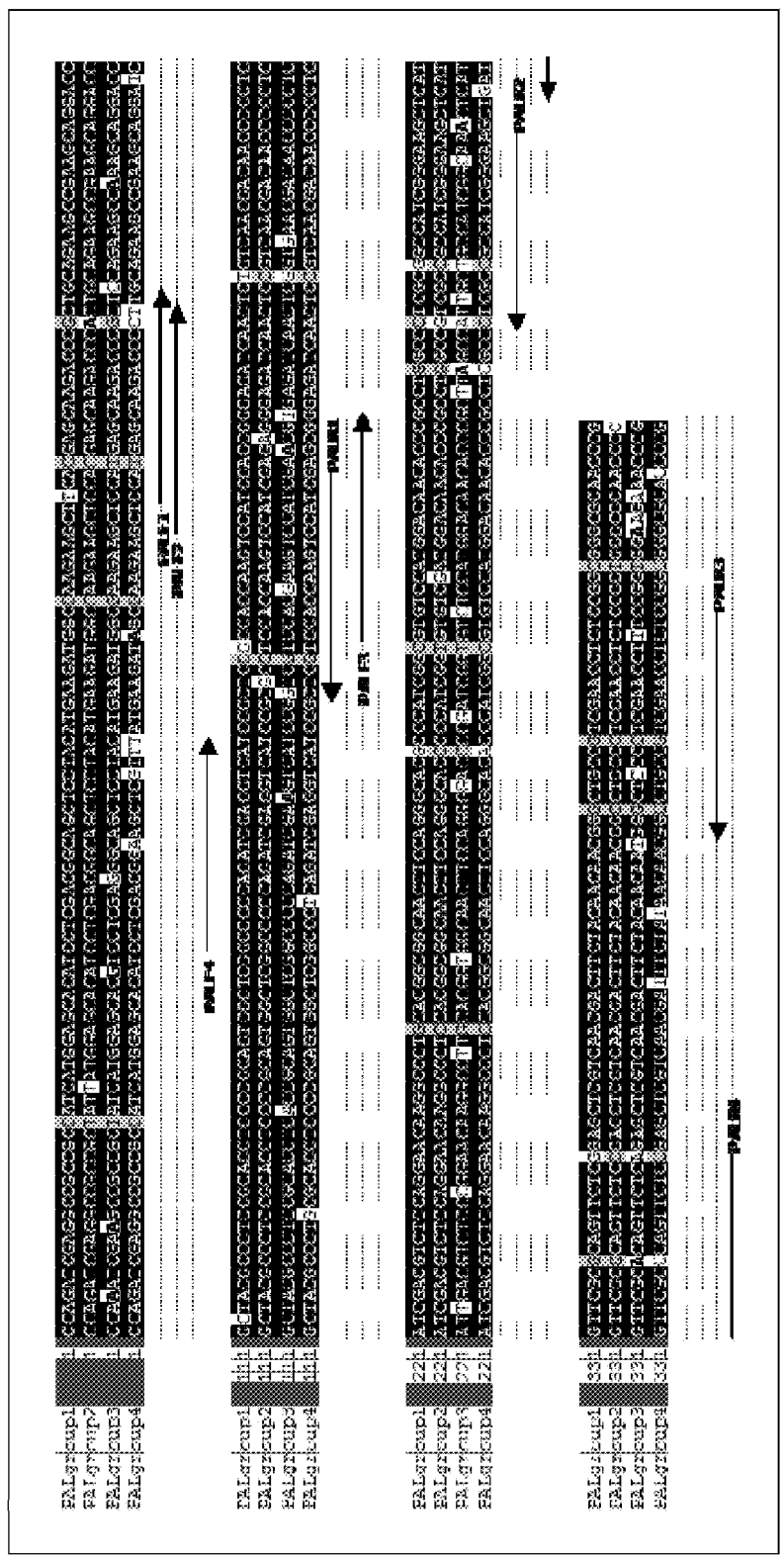

FIG. 4 shows the sequence alignment of the four groups of cloned banana PAL sequences and positions of group-specific primers. The following primer combinations are specific for each of the four groups: PAL(GN)F1 and PAL(GN)R1 for group 1; PAL(CA)F2 and PAL(CA)R2 for group 2; PAL(GN) F3 and PAL(GN)R3 for group 3; PAL(CA)F4 and PAL(CA) R4 for group 4. The sequence does not contain the primers and starts with the 8th codon (CAG) for glutamine (Q). PALgroup1=SEQ ID NO:33; PALgroup2=SEQ ID NO:34; PALgroup3=SEQ ID NO:35 and PALgroup4=SEQ ID NO:36.

Figure 5:
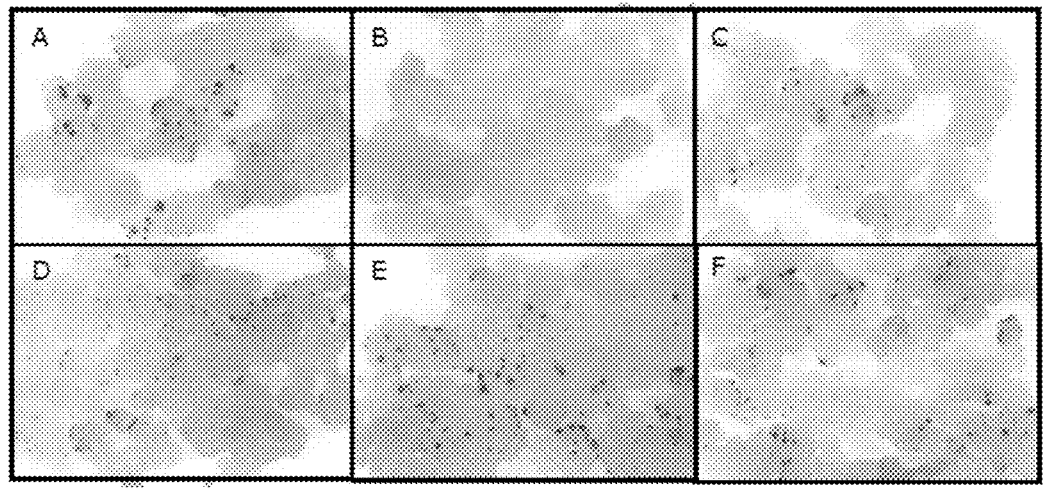

FIG. 5 shows the transient GUS expression in banana embryogenic cells 1 day after microparticle transformation with different promoter constructs. A positive control: plasmid AHC27 containing the uidA reporter gene fused to the maize ubiquitin promoter (UBI); B negative control: untransformed cells; C pLS07 (CAS); D pLS08 (GNL); E pLS11 (CAL); F pLS12 (GNS). Magnification: 30×.

Figure 6:
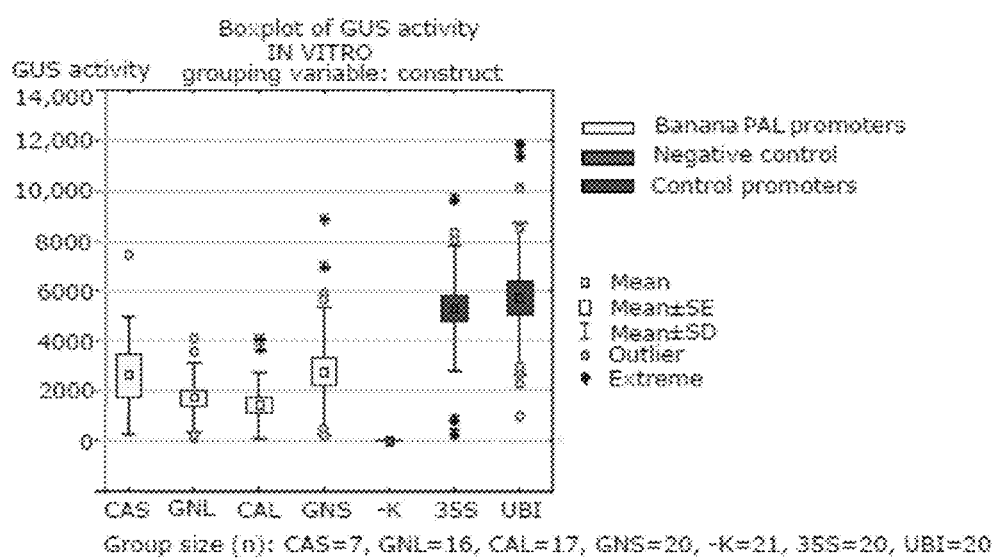
Figure 7:
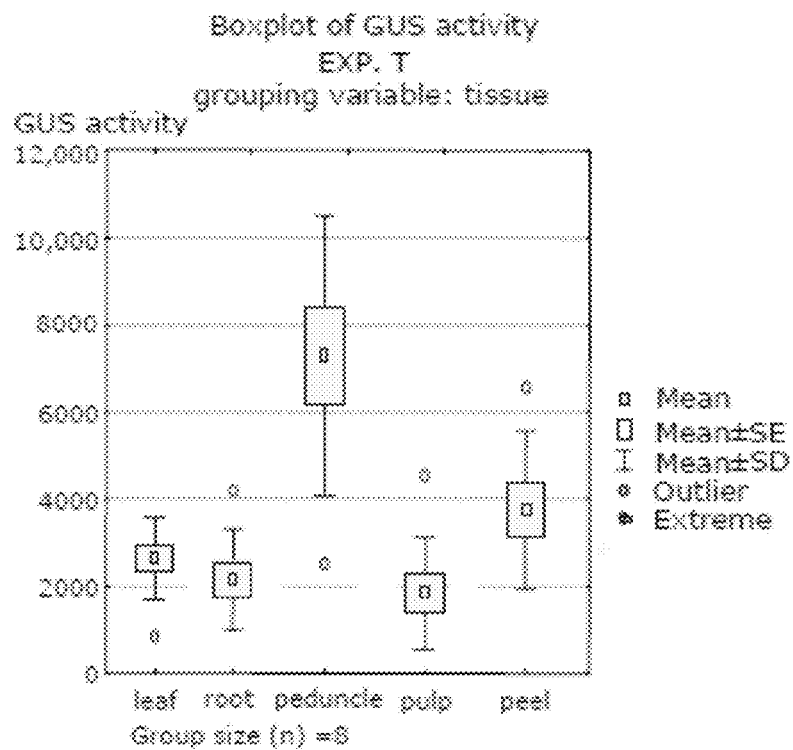

FIG. 6 shows GUS enzymatic activity in leaves of independent transgenic banana in vitro plants expressing different promoter constructs. Specific GUS enzymatic activity expressed in pmoles MU/h/µg total protein. n=number of replicates (samples) tested FIG. 7 shows GUS enzymatic activity in leaf, root, peduncle, pulp and peel of independent transgenic banana plants expressing banana PAL promoter constructs in the field. Specific GUS enzymatic activity expressed in pmoles MU/h/µg total protein. n=number of replicates (samples) tested.

Figure 8:
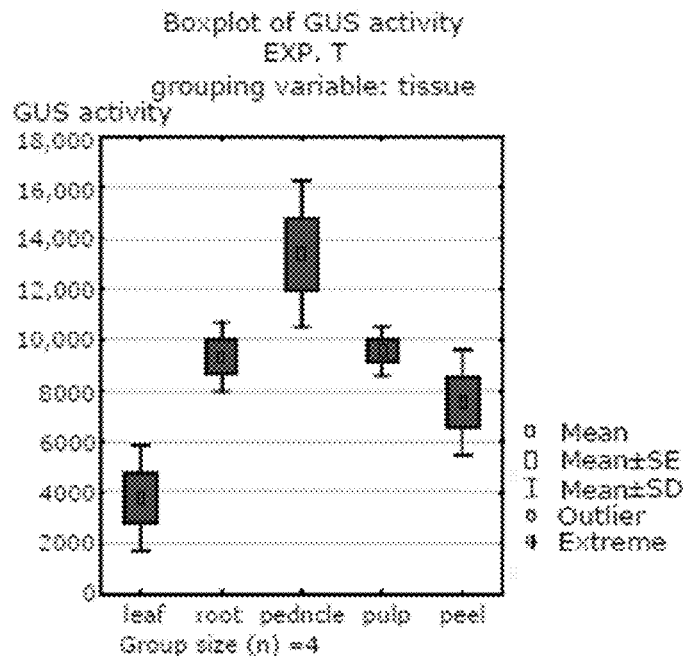

FIG. 8 shows GUS enzymatic activity in leaf, root, peduncle, pulp and peel of independent transgenic banana field expressing constitutive promoter constructs in the field. Specific GUS enzymatic activity expressed in pmoles MU/h/µg total protein. n=number of replicates (samples) tested.

Figure 9:
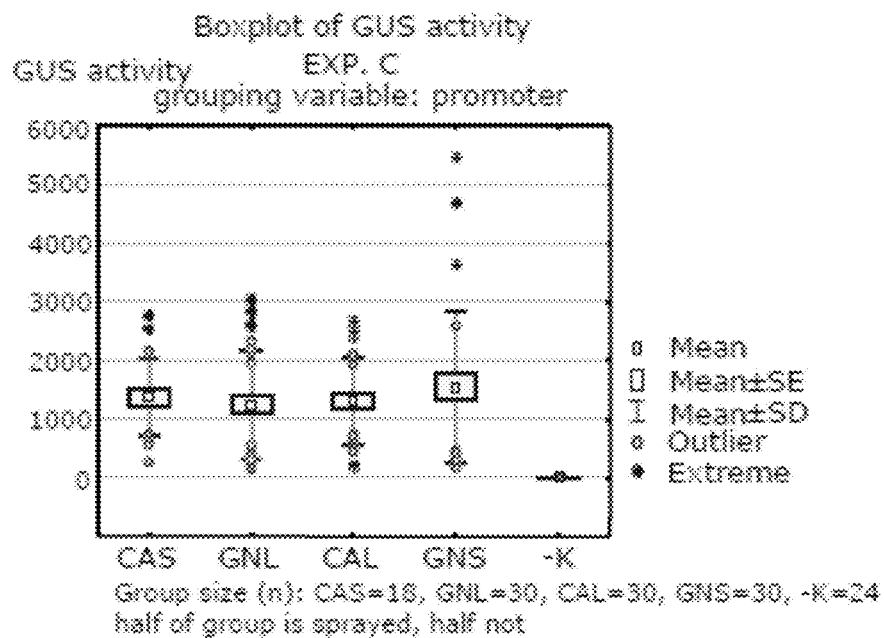

FIG. 9 shows GUS enzymatic activity in leaves of independent transgenic banana plants expressing banana PAL promoter constructs in the screenhouse. Specific GUS enzymatic activity expressed in pmoles MU/h/µg total protein. n=number of replicates (samples) tested.

Figure 10:
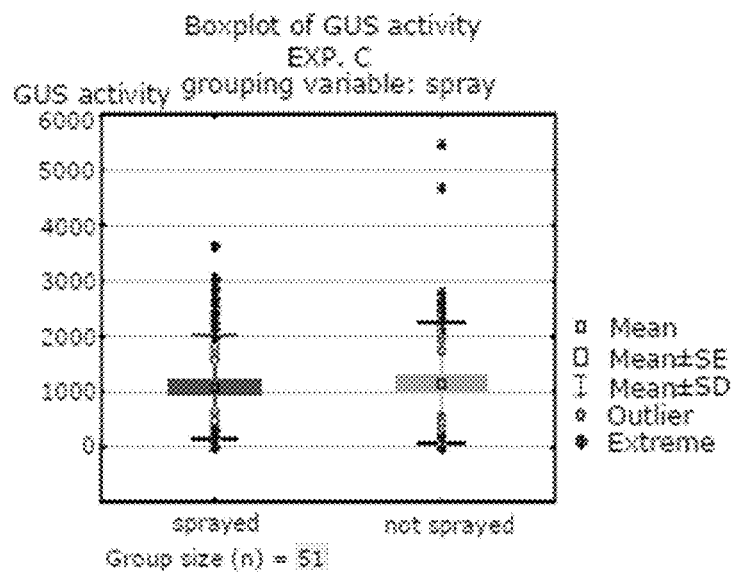

FIG. 10 shows GUS enzymatic activity combined for sprayed or not sprayed leaves of independent transgenic banana plants expressing banana PAL promoter constructs in the screenhouse. Specific GUS enzymatic activity expressed in pmoles MU/h/µg total protein. n=number of replicates (samples) tested.

Figure 11:
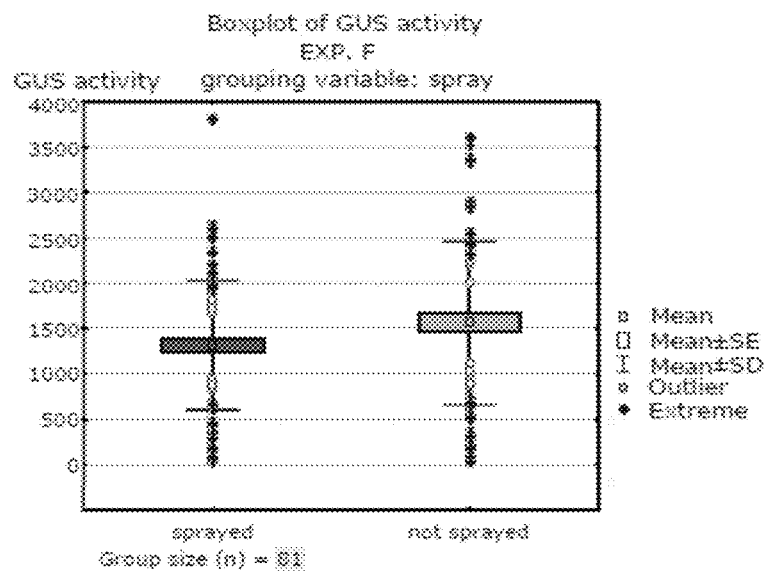

FIG. 11 shows GUS enzymatic activity combined for not infected and infected (resp. sprayed or not sprayed leaves) of independent transgenic banana plants expressing different promoter constructs in the field. Specific GUS enzymatic activity expressed in pmoles MU/h/µg total protein. n=number of replicates (samples) tested.

Figure 12:
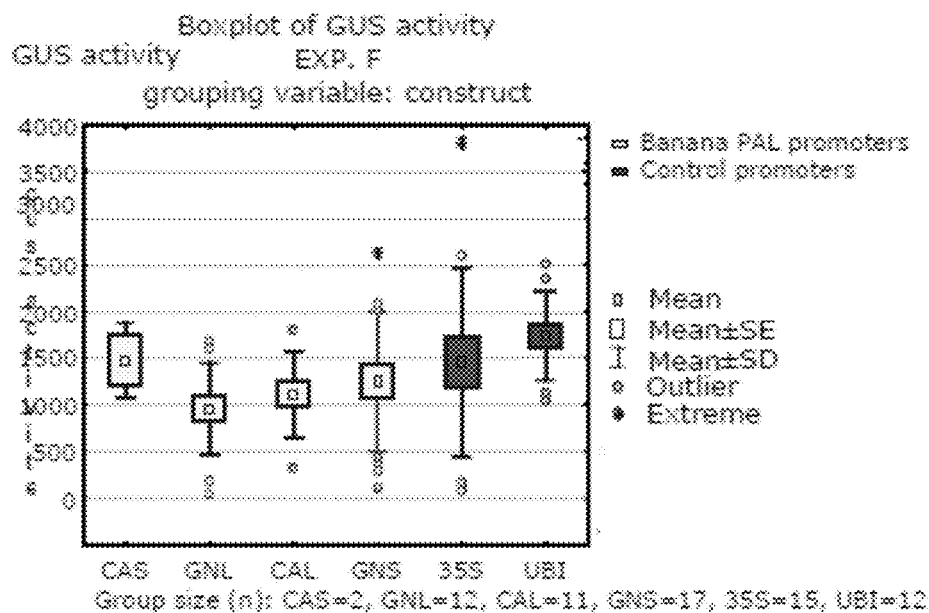

FIG. 12 shows GUS enzymatic activity in sprayed leaves of independent transgenic banana plants expressing different promoter constructs in the field. Specific GUS enzymatic activity expressed in pmoles MU/h/µg total protein. n=number of replicates (samples) tested.

Figure 13:
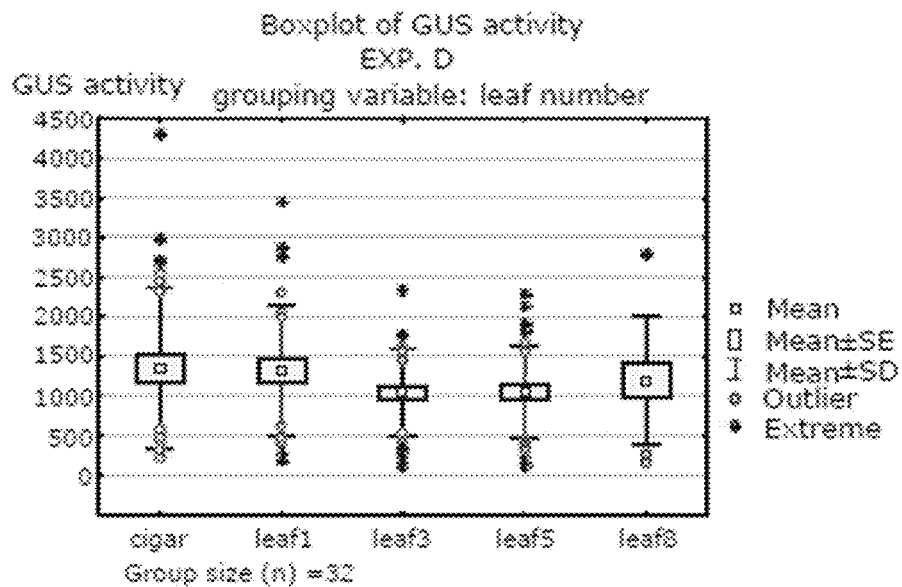

FIG. 13 shows GUS enzymatic activity combined for different leaves of independent transgenic banana plants expressing banana PAL promoter constructs in the field. Specific GUS enzymatic activity expressed in pmoles MU/h/µg total protein. Group size (n=number of replicates (samples) tested): cigar (30); leaf1 (31), leaf3 (32); leaf5 (31); leaf8 (14).

Figure 14:
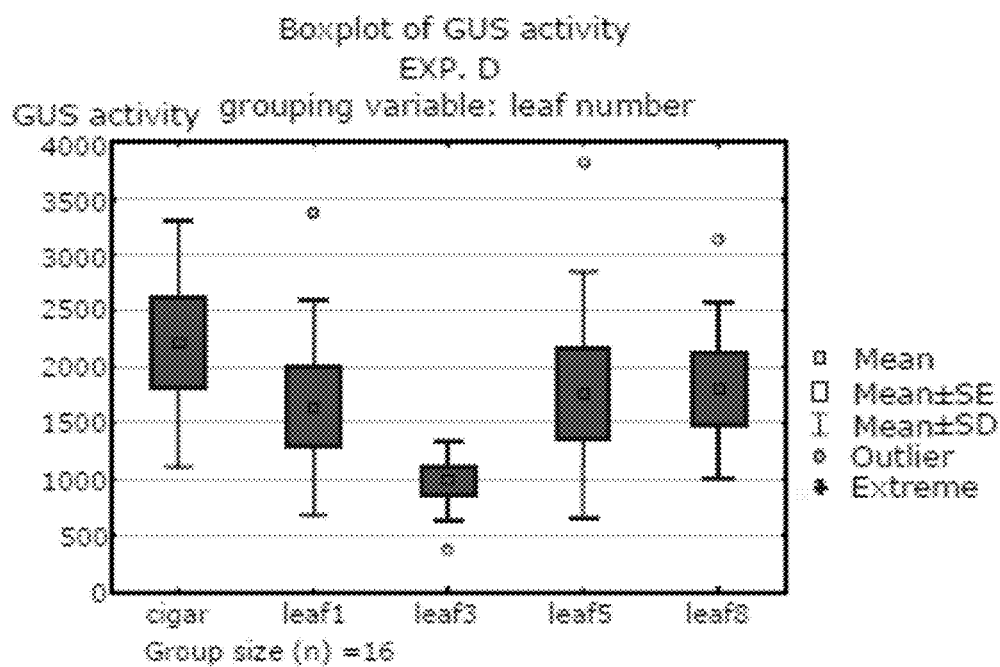

FIG. 14 shows GUS enzymatic activity combined for different leaves of independent transgenic banana plants expressing constitutive promoter constructs in the field. Specific GUS enzymatic activity expressed in pmoles MU/h/µg total protein. Group size (n=number of replicates (samples) tested): cigar (7); leaf1 (7); leaf3 (7); leaf5 (7); leaf8 (6).

Figure 15A:
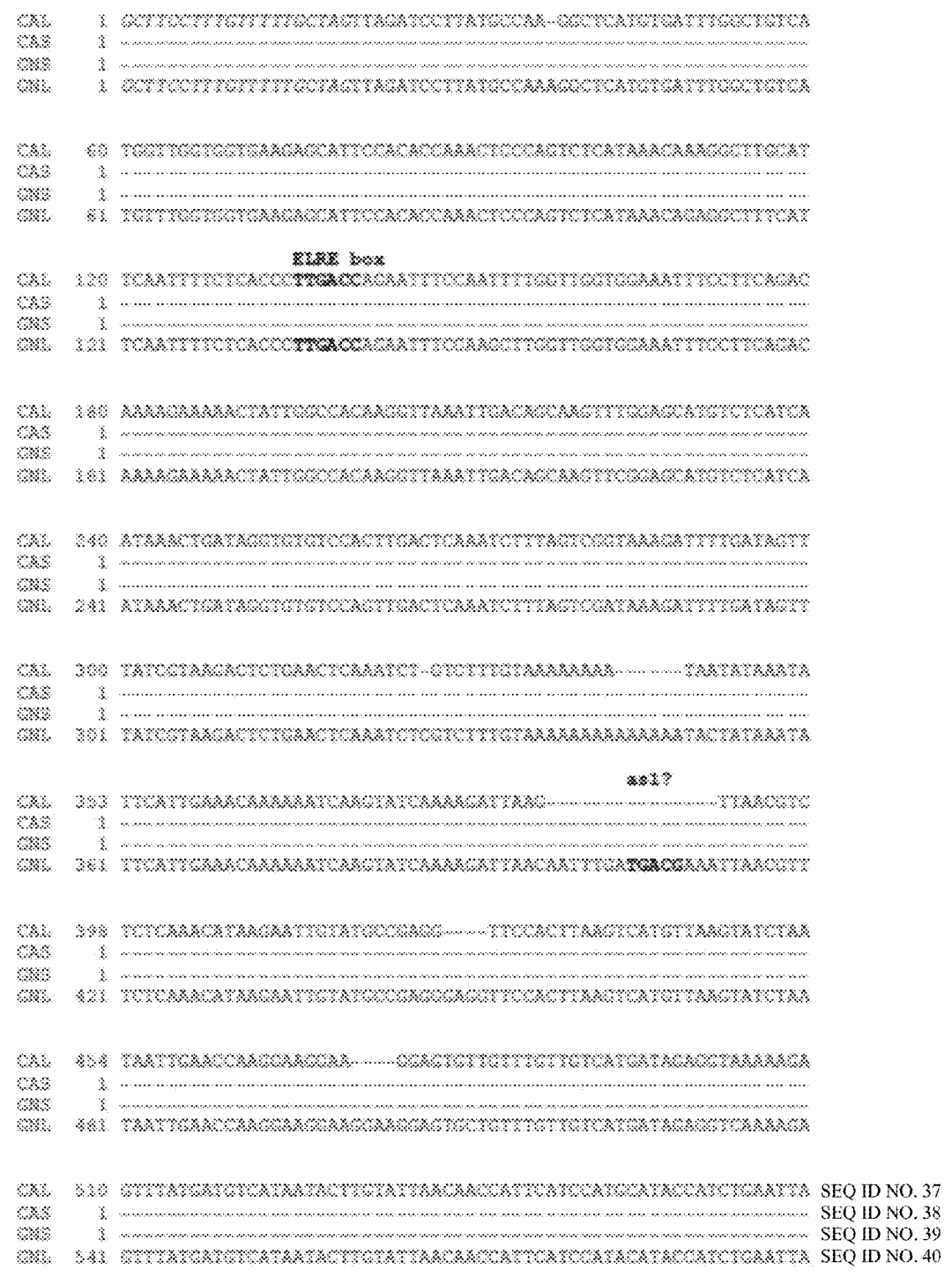
Figure 15B:
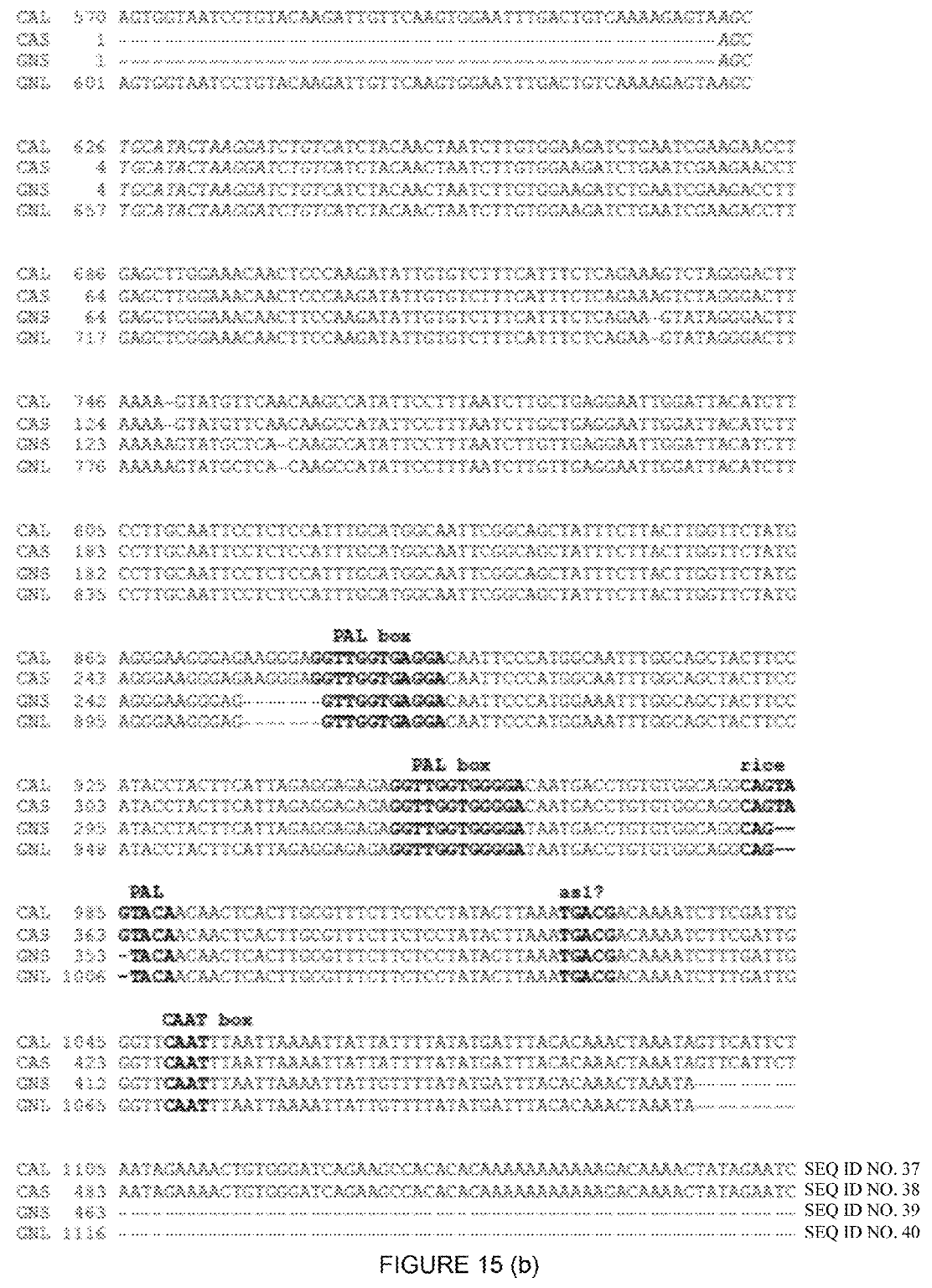
Figure 15C:
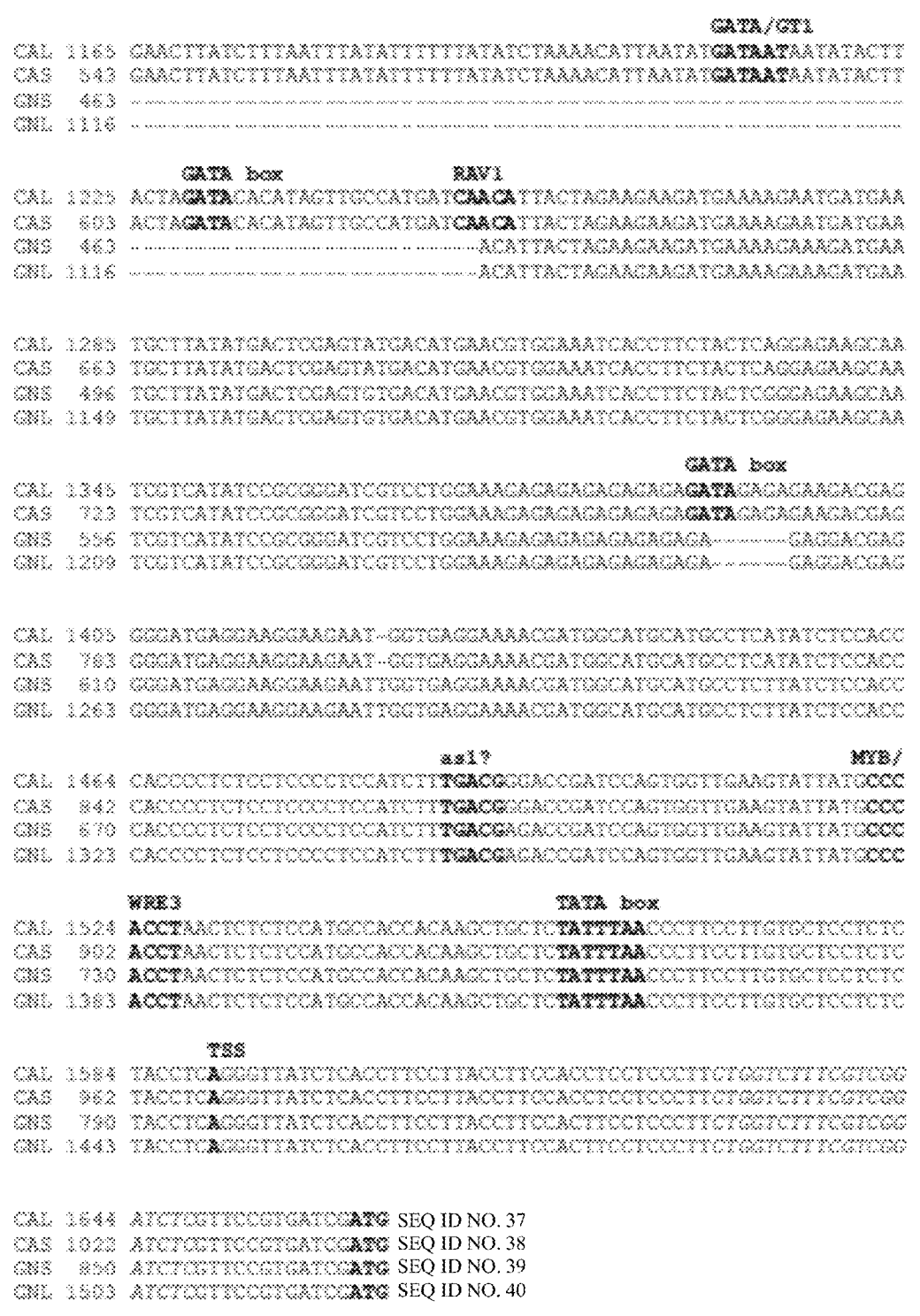

FIG. 15 shows the alignment of the 4 PAL promoter sequences, with their promoter elements.

DESCRIPTION

1. Definitions

So that terms used throughout the description will have a clear and consistent meaning, the following definitions are provided:

By "biologically active fragment" or "active fragment" is meant a fragment of a reference amino acid or nucleotide sequence that has at least about 0.1%, preferably at least about 10%, and more preferably at least about 25% of the activity of a reference promoter sequence. It will also be understood that the phrase "biologically active fragment" or "active fragment" refers to a part of an indicated polynucleotide sequence, preferably a DNA sequence, that initiates RNA transcription or that, when fused to a particular coding sequence and introduced into a plant cell, causes expression of the coding sequence at a level higher than is possible in the absence of such part of the indicated DNA sequence.

Coding sequence: A polynucleotide sequence that encodes a functional RNA transcript, which may or may not be subsequently translated into a polypeptide.

Constitutive Promoter: Promoters referred to herein as "constitutive promoters" actively promote transcription under most, but not necessarily all, environmental conditions and states of development or cell differentiation. Constitutive promoters are active in the majority of cells in an organism. By use of the term nearly constitutive it is implied that the promoter will be in most cases active in all types of cells during plant development, but may be active at a different rate in different types of cells during different stages of plant development.

Endogenous: The term "endogenous," within the context of the current invention refers to any polynucleotide, polypeptide or protein sequence which is a natural part of a cell or organisms regenerated from said cell.

Heterologous sequences: "Heterologous sequences" are those that are not operatively linked or are not contiguous to each other in nature. For example, a promoter from banana is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other. Accordingly a heterologous regulatory and/or coding sequence as used herein referring to a construct comprising a promoter polynucleotide according to the invention indicates that the regulatory sequence and/or coding sequence are not contiguous to each other in nature.

Homologue: A polynucleotide, such as from another organism (virus, bacteria, fungi, animal or plant) that has a sequence identity of at least 70% with a reference promoter sequence after best alignment of the homologue with said reference promoter sequence and preferably with exclusion of gap position having a gap length of at least 5, 6, 7, 8, 9 or 10 nucleotides, and has substantially the same function as the reference polynucleotide sequence. Preferably, the homologue has a sequence identity of at least 80% or 85%, preferably at least 85% or 90%, more preferably at least 95%. In the context of the present invention, substantially the same function refers to having plant promoter activity, more preferably it refers to ensuring substantially the same expression pattern as the reference polynucleotide sequence according to the invention.

Terms used to describe sequence relationships between two or more polynucleotides or polypeptides include "reference sequence", "comparison window", "sequence identity", "percentage of sequence identity" and "substantial identity". "Reference sequence" in the context of the present invention include nucleotide sequence SEQ ID NO:1, SEQ ID NO:2, SEQ ID NO:3 or, more particularly SEQ ID NO:4 or one or more segments thereof that constitute a comparison window of sufficient length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 100 contiguous nucleotides, preferably of at least 150 or 200 contiguous nucleotides, more preferably of at least 300 contiguous nucleotides, most preferably of at least half or substantially all of the nucleotides of a sequence, in which said sequence is compared to a reference sequence of the same number of contiguous positions after the two sequences are optimally aligned. A preferred comparison window covers substantially all of the nucleotides of the sequences, particularly of the shortest sequence. The comparison window may comprise additions or deletions (i.e., gaps) of about 10% or 20% or less as compared to the reference sequence (which does not comprise additions or deletions) for optimal alignment of the two sequences. Optimal alignment of sequences for aligning a comparison window may be conducted by computerised implementations of algorithms (ClustalW, GAP, BESTFIT, FASTA, and TFASTA) or by inspection and the best alignment (i.e., resulting in the highest percentage of identity over the comparison window) generated by any of the various methods selected. Reference also may be made to the BLAST family of programs as for example disclosed by Altschul et al., 1997 (Nucl, Acids Res. 25:3389). A detailed discussion of sequence analysis can be found in Unit 19.3 of Ausubel et al., "Current Protocols in Molecular Biology", John Wiley & Sons Inc, 1994-1998, Chapter 15.

The term "sequence identity" as used herein refers to the extent that sequences are identical on a nucleotide-by-nucleotide basis (DNA or RNA) or an amino acid-by-amino acid basis in the best alignment of said sequences. Thus, a "percentage of sequence identity," as used herein, is determined by comparing two optimally aligned sequences over a comparison window, where the fragment of the polynucleotide in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison (i.e., the "window size"), preferably with exclusion of gap positions of at least 5, 6, 7, 8, 9 or 10 nucleotides, and multiplying the result by 100 to yield the percentage of sequence identity. Another preferred window size corresponds to the number of nucleotides in the shorter of the two sequences.

In particular embodiments of the invention, the optimal alignment of two nucleotide sequences is performed by the basic BLASTn algorithm with the default settings [i.e, "Expect threshold"=10; "word size"=11; "Match/mismatch scores"=(2,-3); "Gap costs"=(existence: 5-extension: 2); filter for low complexity regions & mask for lookup table only). The procedure is typically as follows:

(A) SEQ ID NO:1 and SEQ ID NO:2 were aligned using the basic Blastn algorithm with the default parameters. Very high sequence identity was observed in two regions which constitutes a comparison window of sufficient length: (1) The sequence of the segment between nucleotide 1 and nucleotide 1095 of SEQ ID NO:1 aligned with the sequence of the segment between nucleotide 1 and nucleotide 1120 of SEQ ID NO:2 with 1060 of the nucleotides being identical. Taken into account that the nucleotide sequence of the segment of SEQ ID No:1 is the shortest (1095 nt), this corresponds to ca. 96% sequence identity (1060/1095). (2) The sequence of the segment between nucleotide 1251 and nucleotide 1664 of SEQ ID NO:1 aligned with the sequence of the segment between nucleotide 1120 and nucleotide 1527 of SEQ ID NO:2 with 402 of the nucleotides being identical. Taken into account that the nucleotide sequence of the segment of SEQ ID NO:2 is the shortest (408 nt), this corresponds to ca. 98% sequence identity (402/408).

(B) SEQ ID NO:3 and SEQ ID NO:4 were aligned using the basic Blastn algorithm with the default parameters. Very high sequence identity was observed in two regions which constitutes a comparison window of sufficient length: (1) The sequence of the segment between nucleotide 1 and nucleotide 472 of SEQ ID NO:1 aligned with the sequence of the segment between nucleotide 1 and nucleotide 463 of SEQ ID NO:2 with 451 of the nucleotides being identical. Taken into account that the nucleotide sequence of the segment of SEQ ID NO:2 is the shortest (463 nt), this corresponds to ca. 97% sequence identity (451/463). (2) The sequence of the segment between nucleotide 628 and nucleotide 1041 of SEQ ID NO:1 aligned with the sequence of the segment between nucleotide 463 and nucleotide 870 of SEQ ID NO:2 with 402 of the nucleotides being identical. Taken into account that the nucleotide sequence of the segment of SEQ ID NO:2 is the shortest (408 nt), this corresponds to ca. 98% sequence identity (402/408).

(C) SEQ ID NO:1 and SEQ ID NO:4 were aligned using the basic Blastn algorithm with the default parameters. Very high sequence identity was observed in two regions which constitutes a comparison window of sufficient length: (1) The sequence of the segment between nucleotide 624 and nucleotide 1095 of SEQ ID NO:1 aligned with the sequence of the segment between nucleotide 1 and nucleotide 463 of SEQ ID NO:2 with 451 of the nucleotides being identical. Taken into account that the nucleotide sequence of the segment of SEQ ID NO:2 is the shortest (463 nt), this corresponds to ca. 97% sequence identity (451/463). (2) The sequence of the segment between nucleotide 1251 and nucleotide 1664 of SEQ ID NO:1 aligned with the sequence of the segment between nucleotide 463 and nucleotide 870 of SEQ ID NO:2 with 402 of the nucleotides being identical. Taken into account that the nucleotide sequence of the segment of SEQ ID NO:2 is the shortest (408 nt), this corresponds to ca. 98% sequence identity (402/408).

In yet another particular embodiment of the present invention the optimal alignment & percentage of sequence identity of multiple nucleotide sequences is performed by ClustalW algorithm with the default settings [i.e. for pairwise alignment: alignment type=slow; DNA weight matrix=IUB; gap open=10; gap extension=0.1; for multiple sequence alignment: DNA weight matrix=IUB; Gap open=10; Gap extension=0.2; no end gaps=no; iteration=none; numiter=1; clustering=NJ]. In the ClustalW programme, a pairwise score is calculated for every pair of sequences that are to be aligned. Pairwise scores are calculated as the number of identities in the best alignment divided by the number of residues compared (which will approximately correspond to the shortest sequence and gap positions are excluded). As the pairwise score is calculated independently of the matrix and gaps chosen, it will always be the same value for a particular pair of sequences. Alignment & scoring of SEQ ID NO:1, SEQ ID NO:2; SEQ ID NO:3 and SEQ ID NO:4 shows that:

SEQ ID NO:4 and SEQ ID NO:3 have 97% sequence identity;
SEQ ID NO:4 and SEQ ID NO:1 have 97% sequence identity;
SEQ ID NO:4 and SEQ ID NO:2 have 100% sequence identity (since the latter sequence
comprises SEQ ID NO:4 and hence identical nucleotides)
SEQ ID NO:1 and SEQ ID NO:2 have 95% sequence identity;
SEQ ID NO:1 and SEQ ID NO:3 have 1000% sequence identity (since the latter sequence comprises SEQ ID NO:4 and hence identical nucleotides).

"Substantial sequence identity" or "substantial identity" is in the meaning of a reference sequence and another polynucleotide, preferably of about the same length, and optimally aligned with the reference sequence having at least 70% sequence identity, preferably at least 80% or 85%, more preferably at least 90%, 95% or 97% sequence identity.

The promoters of the invention are in particular embodiments provided as isolated polynucleotides. An "isolated" nucleic acid as used herein is substantially free of flanking sequences, (i.e., sequences located 5' or 3' thereof) present in the native genome of the organism from which the nucleic acid is derived. Preferably, an "isolated" nucleic acid as used herein is in addition substantially free of other cellular materials or culture medium when produced by recombinant techniques, or substantially free of chemical precursors when chemically synthesized.

The term "operably linked" or "operatively linked" as used herein means the functional linkage of a promoter and a second polynucleotide (i.e. the coding sequence), generally orientated in the 5' to 3' direction, in such a way that the transcription of the second polynucleotide is initiated and mediated by the promoter. In general, polynucleotides which are in operative association are contiguous.

The term "polynucleotide" or "nucleic acid" as used herein designates mRNA, RNA, cRNA, cDNA or DNA, preferably DNA. The term typically refers to molecules greater than 30 nucleotides in length.

Promoter: A DNA sequence flanking the coding sequence of a gene at the 5' end thereof which includes an element or elements involved in the initiation of transcription of the coding sequence. A "plant promoter" or "polynucleotide having plant promoter activity" is a promoter capable of initiating transcription in plant cells and can modulate transcription of a polynucleotide. Such promoters need not be of plant origin. For example, promoters derived from plant viruses, such as the CaMV 35S promoter or from *Agrobacterium tumefaciens* such as the T-DNA promoters, can be plant promoters.

"Stringency" as used herein is a function of polynucleotide or probe length, polynucleotide or probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship of hybridization conditions to $T_m$ (in ° C.) is expressed in the mathematical equation $$T_m=81.5-16.6(\log_{10}[Na^+])+0.41(\% G+C)-(600/N) \quad (1)$$

where N is the length of the polynucleotide or probe.

This equation works well for nucleic acids or probes of 14 to 70 nucleotides in length that are identical to the target sequence. The equation below for $T_m$ of DNA-DNA hybrids is useful for polynucleotides or probes in the range of 50 to greater than 500 nucleotides, and for conditions that include an organic solvent (formamide).

$$T_m=81.5+16.6\log\{[Na^+]/(1+0.7[Na^+])\}+0.41(\% G+C)-500/L\ 0.63(\% \text{formamide}) \quad (2)$$

where L is the length of the polynucleotide probe. (P. Tijessen, "Hybridization with Nucleic Acid Probes" in *Laboratory Techniques in Biochemistry and Molecular Biology*, P. C. van der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used [Bonner et al., J. Mol. Biol. 81:123 (1973)], stringency conditions can be adjusted to favour detection of identical genes or related family members.

Variant: The term "variant" is used herein to denote a polynucleotide molecule that differs from a reference polynucleotide in some way, but which preferably have a similar primary biological function as the reference polynucleotide. In general, a "polynucleotide variant" displays substantial sequence identity with a reference polynucleotide sequence or hybridises with a reference sequence under stringent conditions. It will be understood that there may be sequence variations within sequences or fragments used or disclosed in this application.

The terms "variant" or "polynucleotide variant" also encompass polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. Accordingly, "variant" or "polynucleotide variant" in the context of the present promoter polynucleotides encompass polynucleotides that initiate RNA transcription or that, when fused to a particular gene and introduced into a plant cell, cause expression of the gene at a level higher than is possible in the absence of such polynucleotides. The terms "polynucleotide variant" and "variant" also include naturally occurring allelic variants.

Additionally, polynucleotide variants can comprise changes that add or delete a specific polynucleotide sequence to/from the reference sequence, such as e.g. but not limited to a specific UTR or exon sequence. Such addition or deletion can also occur internally, such as e.g. the region between nucleotide 1096 and nucleotide 1251 of SEQ ID NO:1, or at the 5' or 3' end of the polynucleotides of the present invention (e.g. the ATG sequence at the end of SEQ ID NO:1, SEQ ID NO:2; SEQ ID NO:3 or SEQ ID NO:4). Preferably, variants comprise one or more segments of contiguous nucleotides of sufficient length that show at least 70% or 80%, preferably at least 85%, 90%, 95%, or 97%, sequence identity with the corresponding region of the reference promoter sequence of identical size or when compared to an optimally aligned sequence in which the alignment is performed by a computer homology program known in the art. What constitutes suitable variants may be determined by conventional techniques. For example, a reference polynucleotide can be mutated using random mutagenesis (e.g., transposon mutagenesis), oligonucleotide-mediated (or site-directed) mutagenesis, PCR mutagenesis and cassette mutagenesis of an earlier prepared variant or non-variant version of an isolated natural promoter according to the invention.

The one letter code for nucleotides in DNA conforms to the IUPAC-IUB standard described in *The Biochemical Journal* 219:345-373 (1984).

2. Description
2.1 Promoter Sequences

The inventors have isolated promoter sequences and promoter elements following TAIL-PCR of banana phenylalanine ammonia lyase (PAL) gene sequences. These promoters and promoter elements, as well as homologues and variants thereof, can be used (separately or in combination) in conjunction with appropriate coding sequences to prepare transgenic plants capable of expression of the coding sequence(s) of interest at a suitable level.

Thus, in one aspect, the invention provides isolated polynucleotide molecules with plant promoter activity or a promoter-active fragment or a variant or homologue of these. More particularly, the invention provides isolated polynucleotides having plant promoter activity, wherein the polynucleotide comprises a polynucleotide having nucleotide sequence SEQ ID NO:4, or a biologically active fragment or homologue thereof having a nucleotide sequence with at least 70% sequence identity with SEQ ID NO:4.

In particular embodiments the homologues comprise a polynucleotide having a nucleotide sequence with at least 70%, preferably at least 80% or 85%, more preferably 90%, most preferably at least 95% or 97% sequence identity with SEQ ID NO:4 after best alignment of the homologue or variant polynucleotide with SEQ ID NO:4 and preferably with exclusion of gap positions having a gap length of at least 5 nucleotides, preferably at least 6, 7, 8, 9 or 10 nucleotides or by dividing the number of identical position by the number of nucleotides of the shortest of the aligned sequences.

Particular promoter polynucleotides according to the invention comprise a polynucleotide having at least 80%, 85%, 90% or 93%, such as at least 95% or 97% sequence identity with SEQ ID NO:1, SEQ ID NO:2 or SEQ ID NO:3.

Further particular promoter polynucleotides according to the invention comprise a polynucleotide having at least 80%, 85%, 90% or 93%, such as at least 95% or 97% sequence identity with SEQ ID NO:1 and SEQ ID NO:3 or with SEQ ID NO:2 and SEQ ID NO:4.

In further particular embodiments, the isolated promoter polynucleotide sequence operative in a plant cell of the present invention comprises (i) nucleotide sequence SEQ ID NO:1, SEQ ID NO:2, SEQ ID NO: 3 or SEQ ID NO: 4; or (ii) a truncated promoter-active fragment of the isolated polynucleotide of (i); or (iii) a polynucleotide homologue or a variant of (i) or (ii), comprising a polynucleotide having a nucleotide sequence with at least 70%, preferably at least 80% or 85%, more preferably at least 90%, most preferably at least 95% sequence identity with SEQ ID NO:1, SEQ ID NO:2, SEQ ID NO: 3 or SEQ ID NO:4, or comprising one or more segments thereof that constitute a comparison window of sufficient length; or (iv) a polynucleotide homologue or a variant of (i) or (ii) comprising a polynucleotide which hybridises under stringent conditions to (the complement of) the polynucleotide of (i) or (ii).

In a particular embodiment, said polynucleotide homologues or variants of SEQ ID NO:1 comprise a polynucleotide having a nucleotide sequence with at least 70%, preferably at least 80% or 85%, more preferably 90%, most preferably at least 95% sequence identity with the nucleotide sequence between nucleotide 624 and nucleotide 1095 of SEQ ID NO:1 and/or between nucleotide 1252 and nucleotide 1661 of SEQ ID NO:1. In further embodiments said polynucleotide homologues or variants of SEQ ID NO:1 comprise a polynucleotide having substantial sequence identity to SEQ ID NO:1 and/or SEQ ID NO:3 and additionally, as an insert or n- or c-terminal to the polynucleotide(s) having substantial sequence identity, one or more polynucleotide sequences added thereto or deleted therefrom, as compared to SEQ ID NO:1 or SEQ ID NO:3. More particularly, said polynucleotide variant of SEQ ID NO:1 comprises a polynucleotide having substantial sequence identity to SEQ ID NO:1 and/or SEQ ID NO:3 and from which the region between nucleotide 1095 and nucleotide 1252 of SEQ ID NO:1 or part thereof is deleted. In yet a further embodiment of the invention, said polynucleotide homologues or variants of SEQ ID NO:1 comprise SEQ ID NO:2 or SEQ ID NO:4, or polynucleotides having substantial sequence identity thereto.

According to current knowledge, promoter sequences and promoter elements exist as functionally important regions, such as protein binding sites and other promoter elements, and spacer regions. These spacer regions are apparently required for proper positioning of the protein binding sites. Thus, nucleotide substitutions, insertions and deletions can be tolerated in these spacer regions to a certain degree without loss of function. In contrast, less variation is permissible in the functionally important regions, since changes in the sequence can interfere with protein binding. Nonetheless, some variation in the functionally important regions is permissible so long as function is conserved.

Therefore, polynucleotide homologues or variants according to the present invention include polynucleotides with plant promoter activity comprising one or more regions that have substantial sequence identity with the corresponding region or optimally aligned region of the reference promoter sequence SEQ ID NO:1, SEQ ID NO:2, SEQ ID NO:3 or SEQ ID NO:4. It is understood that such regions comprise a comparison window of sufficient length. In the context of the present invention, a comparison window of sufficient length relates to one or more segments of at least 100 contiguous nucleotides, preferably of at least 150 or 200 contiguous nucleotides, more preferably of at least 300 contiguous nucleotides of nucleotide sequence SEQ ID NO:1, SEQ ID NO:2, SEQ ID NO:3 or SEQ ID NO:4. Preferably, the comparison window comprises one or more promoter elements, such as a TATA box, a PAL box, a CAAT box, a GATA box, an AS1 element, MYB/WRE3 element, a translation start signal, a polymerase binding site, an initiator site, a transcription factor binding site, an enhancer, an inverted repeat, a locus control region, or a scaffold/matrix attachment region.

Preferred comparison windows comprise segments of SEQ ID NO:1 or SEQ ID NO:2 of at least 100 contiguous nucleotides, preferably of at least 150 or 200 contiguous nucleotides, more preferably of at least 300 contiguous nucleotides. Other preferred comparison windows comprise the region between nucleotide 624 and nucleotide 1661 of SEQ ID NO:1 or between nucleotide 658 and nucleotide 1524 of SEQ ID NO:2 or segments thereof of at least 100 contiguous nucleotides, preferably of at least 150 or 200 contiguous nucleotides, more preferably of at least 300 contiguous nucleotides. More preferred comparison windows comprise the regions between nucleotide 624 and nucleotide 1095 of SEQ ID NO:1 and/or between nucleotide 1252 and nucleotide 1661 of SEQ ID NO:1 or one or more segments thereof of at least 100 contiguous nucleotides, preferably of at least 150 or 200 contiguous nucleotides, more preferably of at least 300 contiguous nucleotides.

The invention further relates to truncated promoter-active fragments of the promoter sequences disclosed herein. Truncated promoter-active fragments according to the present invention are modified forms of SEQ ID NO:1 or SEQ ID NO:2 or homologues or variants thereof which have plant promoter activity and which are missing at least one nucleotide, preferably at least 10, 50, 100, 150, 200, 250, 300, 400, 500, 600 or more nucleotides from the 3' or 5' end of SEQ ID NO:1 or SEQ ID NO:2 or homologues or variants thereof. Particular truncated promoter-active fragments of promoter sequences of the invention comprises
(i) nucleotide sequence SEQ ID NO:3 or SEQ ID NO:4, or
(ii) a polynucleotide having a nucleotide sequence with at least 70%, preferably at least 80% or 85%, more preferably at least 90%, most preferably at least 95% sequence identity with SEQ ID NO:3 or SEQ ID NO:4 or a segment thereof that constitutes a comparison window of sufficient length.

Those of ordinary skill in the art can determine the nucleotide sequence of plant promoter-active fragments from SEQ ID NO:1 or SEQ ID NO:2, or homologues or variants thereof, required to maintain promoter activity, for example by generating deletion fragments of SEQ ID NO:1 or SEQ ID NO:2, or homologues or variants thereof to obtain putative promoters, operable fusing the putative promoter to a transgene, introducing the construct into a host cell, and measuring expression of the transgene. The transgene may be a reporter, for example, the beta-glucuronidase (gus), green fluorescent protein (gfp), chloramphenicol acetyl transferase (cat), or luciferase (luc) genes. The construct containing the promoter and transgene is cloned into a vector, and the vector is used to transform host cells. Expression of the transgene is measured by assaying for the transgene product. Standard assays are available to sensitively detect the reporter gene product. For example, GUS can be measured by histochemical or fluorometric assays (Mendel et al., 1989; Cervero, 1984). The presence of the transgene product is indicative of a functional promoter.

Isolated polynucleotides comprising the promoters according to the invention can be obtained by cloning DNA from a plant genome, preferably from the genome of banana (*Musa* sp.), such as e.g. from cultivars Grand Naine and Calcutta 4, as known by the person skilled in the art. For instance, these promoter sequences can be generated by direct polymerase chain reaction (PCR) amplification of genomic DNA. Corresponding polynucleotides, preferably DNA, from other species can also be isolated using PCR. The required primers to probe a plant genomic library, such as from banana (*Musa* sp.) or other species, can be designed and optimized from the nucleotide sequence data of SEQ ID NO: 1, SEQ ID NO: 2, SEQ ID NO: 3 or SEQ ID NO:4. Other procedures for isolating polynucleotides comprising the promoter sequences of the invention include, without limitation, tail-PCR, and 5' rapid amplification of cDNA ends (RACE). Yet another method of producing the polynucleotides of the present invention is by DNA synthesis. Complementary oligonucleotides can also be synthetised to form a double-stranded molecule of the desired polynucleotide sequence. In addition, well-known methods of enzymatic and chemical synthesis and modification of nucleic acids may be used to obtain promoter sequences having substantial sequence identity to SEQ ID NO:1, SEQ ID NO:2, SEQ ID NO:3, SEQ ID NO:4 or fragments thereof.

The present invention is also directed to methods for isolating the promoter of the present invention from plants comprising (a) probing a plant genome with a polynucleotide comprising the sequence of SEQ ID NO: 1, SEQ ID NO: 2, SEQ ID NO: 3 or SEQ ID NO:4 or one or more fragments thereof, (b) hybridizing said polynucleotide to a nucleic acid of the plant genome under stringent conditions, and (c) isolating the promoter from the plant genome. Preferably, the plant genome is a banana (*Musa* sp.) genomic library.

Accordingly the present invention provides sequences which are complementary to the promoter polynucleotide sequences of the present invention, more particularly which are capable of specifically hybridizing to the sequences of the present invention and homologues or variants thereof. In particular embodiments the probes and primers according to this aspect of the invention comprise a sequence which is complementary to a sequence which contains at least 70% sequence identity with a region within SEQ ID NO:1, SEQ ID: 2, SEQ ID NO: 3 and/or SEQ ID NO:4 and which does not comprise 100% sequence identity with any other natural sequence. In particular embodiments, the primers and probes have a length of between 10 and 100 nucleotides.

2.2 Constructs & Vectors

The present invention further provides polynucleotide constructs comprising said promoter polynucleotide sequences according to the present invention operably linked to a heterologous coding sequence and/or regulatory sequence. Thus, said polynucleotide constructs comprise a polynucleotide with plant promoter activity operably linked to a heterologous coding sequence or another, heterologous, regulatory sequence wherein said promoter sequences comprise More particularly, the invention provides polynucleotide constructs comprising promoter polynucleotides having plant promoter activity linked to a heterologous coding sequence and/or regulatory sequence, wherein the promoter polynucleotide comprises a polynucleotide having nucleotide sequence SEQ ID NO:4, or a biologically active fragment or homologue thereof having a nucleotide sequence with at least 70% sequence identity with SEQ ID NO:4.

Particular embodiments of the promoter polynucleotide sequences for use in the polynucleotide constructs according to the invention correspond to the embodiments of the promoter polynucleotide sequences described above.

Said heterologous coding sequence can encode an RNA which functions as antisense RNA, a ribozyme or as a structural component, or is translated into a polypeptide which functions as an enzyme, a structural component, a marker, or has some physiological effect. Said heterologous coding sequence includes all synthetically engineered and biologically derived coding sequences or genes which may be introduced into a plant by genetic engineering, including but not limited to non-plant genes, foreign or endogenous plant genes, modified genes, synthetic genes and portion of genes. Said coding sequence can encode more than one RNA or more than one polypeptide. Furthermore, Said coding sequence can encode a combination of at least one RNA and at least one polypeptide. Said coding sequences include, for example, an open reading frame, a portion of an open reading frame, a polynucleotide encoding a fusion protein, an antisense sequence, a sequence encoding a double-stranded RNA sequence, a transgene, and the like.

Non-limiting examples of transgene products which can be usefully expressed in transgenic plants using promoters according to the invention are gene products that help (1) to obtain disease resistance or tolerance against plant-infecting viruses, bacteria, fungi or nematodes; (2) to obtain resistance against herbivores and other pests; (3) to obtain resistance against herbicides, heavy metals or selectable marker reagents; (4) to confer resistance against abiotic factors and environmental stress (e.g. draught, salt, cold, anaerobic conditions); (5) to conduct functional analyses of genes and gene products for research (by using selectable and/or screenable marker genes); (6) to confer silencing or enhancement of genes and gene products (modulation of gene expression); (7) to modify the composition of macromolecules and secondary metabolites (e.g. to increase nutritional value or to alter structural composition, such as to improve starch properties or quantity, oil quantity and quality, amino acid or protein composition and the like); (8) to modify plant development, or (9) to improve fruit or crop yield and/or quality (e.g. post harvest shelf life or disease resistance).

In a particular embodiment, the polynucleotide construct according to the present invention is further characterised in that said promoter or biologically active fragment or variant thereof, is capable of conferring transcription, preferably high levels of transcription, of the foreign or endogenous, but heterologous, coding sequence in specific, many or all tissues of a plant. Said plant tissues include differentiated and undifferentiated tissues or plants, including but not limited to roots, stems, shoots, cotyledons, epicotyl, hypocotyl, leaves, pollen, seeds, tumor tissue and various forms of cells in culture such as single cells, protoplast, embryos, and callus tissue. Said plant tissue may be in plants or in organ, tissue or cell culture.

Representative coding sequences include, for example, a bacterial dap A gene for increased lysine; genes that encode *Bacillus thuringiensis* (Bt) endotoxins (inter alia U.S. Pat. Nos. 5,460,963; 5,683,691; 5,545,565; 5,530,197; 5,317,096) or insecticidal toxins isolated from *Photorhabdus* (WO97/17432 or WO98/08932) for insect resistance; lytic peptides genes for disease resistance, genes imparting tolerance to oxynil herbicides (U.S. Pat. Nos. 4,810,648 and 5,559,024), bacterial or plant EPSPS for resistance to glyphosate and EPSPS inhibitor herbicides (U.S. Pat. Nos. 4,940, 835; 5,188,642; 4,971,908; 5,145,783; 5,312,910; 5,633,435; 5,627,061; 5,310,667, WO 97/04103); genes imparting tolerance to glufosinate (EP 242 236) bacterial or plant HPPD (WO 96/38567, WO 98/02562) for resistance to HPPD-inhibitor herbicides (i.e. diketones, isoxazoles, etc.), chitinase or glucan endo-1,3-β-glucosidase for fungicidal properties, ACC synthase and ACC oxidase for fruit ripening control. Also, the coding sequence may be introduced to act as a genetic tool to generate mutants and/or assist in the identification, genetic tagging, or isolation of segments of genes, e.g. monocot genes.

The polynucleotide construct comprising the promoter sequence of the present invention can include more than one promoter operatively linked to the coding sequence. These additional promoters can be identical promoters, derivatives of the same promoter, or heterologous promoters. In addition, operatively linked regulatory elements such as enhancers or silencers can be included in the polynucleotide constructs.

The polynucleotide construct comprising the promoter of the present invention operably linked to a heterologous coding sequence may be constructed by methods well-known in the art. The construct may also contain polyadenylation sites at the 3'-end of the coding sequence.

Vectors are a useful component of the present invention. In particular, the present promoters and/or promoter control elements may be delivered to a system such as a cell by way of a vector. For the purposes of this invention, such delivery may range from simply introducing the promoter or promoter control element by itself randomly into a cell to integration of a cloning vector containing the present promoter or promoter control element. Thus, a vector need not be limited to a DNA molecule such as a plasmid, cosmid or bacterial phage that has the capability of replicating autonomously in a host cell. All other manner of delivery of the promoters and promoter control elements of the invention are envisioned. Many useful vectors are commercially available. Thus, in a further aspect, the present invention provides vectors comprising the promoters or polynucleotide constructs of the present invention.

The vectors may be derived from plasmids, cosmids, bacteriophage and viruses. The vectors include direct DNA delivery vectors, and vectors for *Agrobacterium*-mediated gene transfer. Direct DNA delivery vectors and *Agrobacterium* based vectors, and methods for their construction, are well-known in the art and disclosed for example in "Gene Transfer to Plants", Potrykus et al., eds., Springer-Verlag, Berlin 1995 and "Plant Molecular Biology: A Practical Approach", Shaw, ed., IRL Press, Oxford 1988.

Vectors for direct DNA delivery generally contain the polynucleotide construct of the invention in a selectable bacterial replicon, and may further contain additional regulatory elements, reporter genes, and selectable markers. Vectors for *Agrobacterium*-mediated gene transfer generally contain functions to allow maintenance in *E. coli* and *Agrobacterium*, transfer from *E. coli* to *Agrobacterium*, and, *Agrobacterium* T-DNA border fragments. The vectors may be integrative or binary vectors. In a preferred embodiment, the vector is a binary vector for *Agrobacterium*-mediated gene transfer.

The vectors may further contain selectable markers and reporter genes to facilitate identification and selection of transformed cells, and suitable regulatory sequences to enable expression in plants. Weising et al. (1988) Annual Rev. Genetics 22:241 describe components that may be included in the subject vectors such as polyadenylation sequences, marker genes, reporter genes, enhancers, and introns.

The present vectors will generally contain either a selectable marker or a reporter gene or both to facilitate identification and selection of transformed cells. Alternatively, the selectable marker may be carried on a separate vector and used in a co-transformation procedure. Both selectable markers and reporter genes may be flanked with appropriate regulatory sequences to enable expression in plants. Useful selectable markers are well known in the art and include, for example, antibiotic and herbicide resistance genes. Specific examples of such genes are disclosed in Weising et al. (cf supra) and Miki and McHugh (Journal of Biotechnology, 2004, 107: 193-232). Other selectable marker genes include genes encoding for xylose isomerase, phosphomannose isomerase, cyanamide hydratase, acetolactate synthase, EPSP synthase, glutamin synthase, tryptophan decarboxylase. A preferred selectable marker gene is the hygromycin B phosphotransferase (hpt) coding sequence, which may be derived from *E. coli*. Other preferred selectable markers known in the art include aminoglyvoside phosphotransferase gene of transposon Tn5 (AphII) which encodes resistance to the antibiotics kanamycin, neomycin, and G418, as well as those genes which code for resistance or tolerance to glyphosate, bialaphos, methotrexate, imidazolinones, sulfonylureas, bromoxynil, dalapon, and the like. Selectable marker genes that confer herbicide tolerance are also of commercial utility in the resulting transformed plants.

To determine whether a particular combination of a coding sequence and recipient plant cells are suitable for use herein, the vector may include a reporter gene. Reporter genes which encode easily assayable marker proteins are well known in the art. In general, a reporter gene is a gene which is not present or expressed by the recipient organism or tissue and which encodes a protein whose expression is manifested by some easily detectable property, e.g., phenotypic change of enzymatic activity. Examples of such genes are provided in Weising et al., supra. Preferred genes include the beta-glu-ronidase (gus) gene of the uidA locus of *E. coli*, the chloramphenicol acetyl transferase (cat) gene from Tn9 of *E. coli*, the green fluorescence protein (GFP) gene from *Aequoria victoria*, and the luciferase (luc) gene from the firefly *Photinus pyralis*.

Other elements such as introns, enhancers, polyadenylation sequences and the like, may also be present in the construct or vector of the present invention. These elements must be compatible with the remainder of the gene constructions. Such elements may or may not be necessary for the function of the gene, although they may provide a better expression or functioning of the gene by effecting transcription, stability of the mRNA, or the like. Such elements may be included in the polynucleotide as desired to obtain the optimal performance of the transforming gene in the plant. For example, the maize Adh1 S first intron may be placed between the promoter and the coding sequence. This intron, when included in a gene construction, is known to generally increase expression in maize cells of a protein (Callis et al. (1987) Genes Dev. 1:1183). However, sufficient expression for a selectable marker to perform satisfactorily can often be obtained without an intron (Battraw et al. (1990) Plant Mol. Biol. 15:527).

Transcription activators such as enhancers include the tobacco mosaic virus (TMV) translation activator (WO087/07644) and the tobacco etch virus (TEV) translation activator (Carrington et al. (1990) J. Virol. 64:1590). Polyadenylation and terminator regulation sequences include sequences of bacterial origin, such as the nopaline synthase (nos) terminator of *Agrobacterium tumifaciens*, or of plant origin such as the histone terminator (EP 0633317). The vector comprising the promoter of the present invention operably linked to a coding sequence may also comprise sequences coding for a transit peptide, to drive the protein coded by the coding sequence into the chromoplasts of the plant cells. Such transit peptides are well known to those of ordinary skill in the art, and may include single transit peptides, as well as multiple transit peptides obtained by the combination of sequences coding for at least two transit peptides.

2.3 Transformation of Plants, Plant Tissue and Plant Cells

Techniques for introducing the polynucleotide constructs of the present invention into the genome of a plant are well known in the art and are described, for example by Sági et al., (Bio/Technology, 1995, 13, 481-485), May et al. (Bio/Technology, 1995, 13, 485-492), Zhong et al., Plant Physiol., 1996, 110, 1097-1107). The constructs of the present invention are introduced into plant cells by methods known in the art. Direct gene transfer methods include gene transfer to protoplasts by microinjection, electroporation, chemically-induced DNA uptake (Potrykus, supra) and biolistic (microprojectile bombardment) approaches (Klein et al. (1987) Nature 327:70). *Agrobacterium* mediated gene transfer methods include leaf disk transformation, protoplast culture, transformation of seed, stem or root explants, in planta vacuum-infiltration (Potrykus, supra), and transformation of inflorescence (U.S. Pat. No. 6,037,522).

It is another object of the present invention to provide a transformed host cells, preferably transformed plant cells comprising the polynucleotide sequences with plant promoter activity operably linked to a heterologous (foreign or endogenous) coding sequence and more particularly the polynucleotide constructs of the present invention or fragment thereof as described hereinabove.

Preferably, said promoter polynucleotide or said polynucleotide construct of the present invention is stably incorporated in the genome of said plant cell. The invention also contemplates methods for producing transformed host cells, preferably plant cells, comprising introducing into regenerable plant cells a polynucleotide construct according to the present invention so as to yield transformed plant cells and identifying or selecting transformed plant cells.

Plant cells into which the polynucleotides of the present invention can be introduced include cells of all plants into which polynucleotides can be transferred. Plant cells include undifferentiated tissues such as calli and differentiated tissues such as embryos, plant portions, plants, fruits and seeds. Promoters according to the invention can be used in monocotelydonous and dicotelydonous plant cells. In a preferred embodiment promoters according to the invention are used in plant cells from a plant species belonging to the Musaceae, Poaceae, Brassicaceae or Solanaceae, or a plant cell from soybean, sunflower, sugar beet, alfalfa, peanuts, cotton, coffee, coconut, pineapple or citrus fruits. In a more preferred embodiment said transformed plant cell is a plant cell from banana, rice, corn, wheat, barley, oat, rye, sorghum, sugar cane, potato, tomato, tobacco or oil-seed rape.

In particular embodiments, transformation of plant cells with the promoters, polynucleotide constructs or vectors of the present invention imparts a phenotypic characteristic to the transformed cells.

The promoters, polynucleotide constructs, vectors, and plant cells of the present invention are useful for making recombinant gene products in vitro, and for making transgenic plants with desirable properties.

Accordingly, a further aspect of the invention provides transgenic plants, progeny thereof, plant parts, plant tissues, plant fruits and seeds and other parts thereof containing the polynucleotide construct, preferably DNA construct, of the present invention, stably integrated into the genome. Thus, the present invention provides transgenic plants, progeny thereof, plant parts, plant tissues, fruits and seeds and other parts thereof comprising the promoter-active polynucleotides of the present invention operably linked to a heterologous sequence which is a coding sequence or another regulatory sequence as described herein or comprising the polynucleotide constructs described herein.

Both monocotyledonous and dicotyledonous plants are contemplated. It has been demonstrated that the promoters according to the present invention can direct expression in both monocots and dicots. In particular embodiments, transformed plants, progeny thereof, plant parts, plant tissues, fruits and seeds and other parts thereof comprising the promoters or polynucleotide constructs comprising said promoter sequences operably linked to a heterologous coding sequence or another regulatory sequence, are from a plant species belonging to the Musaceae, Poaceae, Brassicaceae or Solanaceae, or a plant cell from soybean, sunflower, sugar beet, alfalfa, peanuts, cotton, coffee, coconut, pineapple or citrus fruits. In a more preferred embodiment said transformed plants, progeny thereof, plant parts, plant tissues and seeds and other parts thereof selected from the group consisting of banana, rice, corn, wheat, barley, oat, rye, sorghum, sugar cane, potato, tomato, tobacco and oil-seed rape. In particular embodiments, the plants are monocots, most particularly from the family of the Musaceae and Poaceae.

The transgenic plants, progeny thereof, plant parts, plant tissues, plant fruits and seeds and other parts thereof containing the polynucleotide construct of the present invention may be subject to further processing steps, particularly food processing steps, including but not limited to milling, cutting, peeling, mashing, drying, cooking, baking, frying, freezing, etc. Accordingly, the present invention also envisages processed products, such as, but not limited to food products, comprising the polynucleotide constructs according to the present invention.

Particular embodiments of the invention relate to banana plants comprising the promoters or polynucleotide constructs according to the invention. The present inventors identified novel banana promoters which can be used to direct transgene expression in banana. This is of particular interest where the use of non-plant promoters is to be avoided. The banana promoters off the present invention are of particular use for directing expression constitutively in banana which is of interest in the context of disease and/or pest (e.g. fungus) resistance or other traits (including production of proteins such as vaccines) for which constitutive expression is desirable. Accordingly, particular embodiments of the invention relate to banana plants or banana fruit comprising, integrated into their genome, one or more polynucleotide constructs according to the invention comprising nucleotide sequences with plant promoter activity according to the invention driving the expression of one or more genes conferring a trait of interest to the banana plant.

In further particular embodiments of the invention, the plants comprising the promoter or polynucleotide constructs of the present invention are selected from rice and tobacco.

According to a particular aspect of the invention, transformation of plant cells with the promoters, polynucleotide constructs or vectors of the present invention imparts a phenotypic characteristic to the transformed cells. Plant cells are transformed with the polynucleotide construct by any of the plant transformation methods known in the art, such as those described above, and regenerated into a complete transgenic plant by methods well known to those of ordinary skill in the art (Potrykus, supra, Shaw, supra). For in planta transformation methods, the regeneration step is not needed. Generally, germinating seeds or wounded plants are inoculated with *Agrobacterium* containing the nucleic acid construct, plants are grown to maturity, and seeds are collected, sown, and transformants are selected.

A method of making a transgenic plant comprising the polynucleotide construct of the present invention comprises transforming a plant cell with a vector comprising one or more of the promoter polynucleotides of the present invention (i.e. a polynucleotide comprising SEQ ID NO:4 or a homologue or variant thereof or a biologically active truncated fragment thereof such as the polynucleotides comprising SEQ ID NO:1, SEQ ID NO:2, SEQ ID NO:3 or SEQ ID NO:4) operably linked to a heterologous coding sequence to provide a transformed plant cell, and regenerating a transgenic plant from the transformed plant cell. A further method of making a transgenic plant comprising the polynucleotide construct of the present invention comprises transforming a seed or immature plant with a vector comprising one or more of the promoter polynucleotides of the present invention (i.e. a polynucleotide comprising SEQ ID NO:4 or a homologue or variant thereof or a biologically active fragment thereof) operably linked to a foreign or endogenous coding sequence, growing the seed or plant to maturity, obtaining the seeds of the plant, and generating transgenic plants from the seeds. The transgenic plants of the present invention are useful in that they may express a gene product for a desired property such as fungal resistance, disease resistance, insect resistance, pesticide resistance, heat, cold or drought tolerance, herbicide tolerance, improved properties, and so on.

The resulting transformed plant of this invention expresses the inserted coding sequence under the control of one or more of the promoter sequences of the present invention. Such a plant can be used in a conventional breeding scheme to produce more transformed plants with the same improved phenotypic characteristics, or to introduce the gene into other varieties of the same or related plant species. The transgenic plants of the invention may be crossed with similar transgenic plants or with plants lacking the promoter of the invention operably linked to a coding sequence, using known methods of plant breeding, to prepare seed. Seeds, which are obtained from transformed plants, contain the gene as a stable genomic insert. The seed is then planted to obtain a crossed fertile transgenic plant comprising the coding sequence of interest operatively linked to the promoter of the invention. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants.

The invention is further embodied in a crop comprising a plurality of the transgenic plants of the invention, planted together in an agricultural field.

It will be understood that this is not an exclusive list, but merely suggestive of the wide range of utility of the polynucleotides and regulatory elements of the present invention.

The following examples are presented in order to more fully illustrate the preferred embodiments of the invention. They should in no way be construed, however, as limiting the broad scope of the invention.

EXAMPLES

Materials & Methods

1. Materials

The different banana landraces used for infection, inoculation and gene cloning, together with their characteristics, are listed in Table 1.

TABLE 1

Banana landraces

| Land race | Genome comp. | Resistance to M.f. | Origin | Accession number | Code |
|---|---|---|---|---|---|
| 'Calcutta 4' | AA | Total | ITC Leuven | ITC.0249 | CA |
| 'Tuu Gia' | AA | Total | ITC Leuven | ITC.0610 | TG |
| 'Grande Naine' | AAA | Susceptible | ITC Leuven | ITC.0180 | GN |

M.f.: *Mycosphaerella fijiensis*,
ITC: International Transit Centre of Bioversity at Katholieke Universiteit Leuven For genetic transformation, the following four species and respective material were employed.

In banana, embryogenic cell suspension cultures of the commercial dessert banana cultivar 'Grande Naine' (GN, ITC.1256, cell lines 128f and 128h) were maintained and subcultured in half-strength MS medium (Murashige and Skoog, 1962) supplemented with 5 µM 2,4-D and 1 µM zeatin, called ZZ medium (Dhed'a et al., 1991).

In rice, embryogenic calli were induced from sterilized mature seeds of the standard *japonica* cultivar 'Nipponbare' as described by Sallaud et al. (2003).

For *Arabidopsis*, seeds of the standard ecotype Col0 and the sgs2 [suppressor of gene silencing—SGS2 encodes an RNA-dependent RNA polymerase, which plays a key role in posttranscriptional (trans)gene silencing (Mourrain et al., 2000)] mutant in the same genetic background (Elmayan et al., 1998) were sown and the seedlings grown until early flowering stage in the greenhouse.

Tobacco (*Nicotiana benthamiana*) plants were grown under greenhouse conditions from sterilized seeds. The youngest leaves of fully developed (approx. 8-weeks-old) plants were then used for infiltration with a needle-less syringe.

*Mycosphaerella fijiensis* Morelet (M.f.) is the causal agent of the devastating widespread banana leaf streak disease called black Sigatoka.

*Colletotrichum musae*[(Berk. & M. A. Curtis) Arx 1957] (C.m.) is a banana fruit pathogen, but it can also be inoculated on leaves (Postmaster et al., 1997). This pathogen was used because it is more efficient in in vitro inoculation experiments than M.f.

2. Inoculation and Infection Experiments

*Colletotrichum musae*

Leaf pieces (5×5 cm) were cut from young leaves of greenhouse plants (GN and TG), surface sterilized in 70% (v/v) ethanol, rinsed in sterile water and dried. Next, a hole (5 mm diameter) was pierced with a cork borer in the center and the leaf piece was placed abaxial side up in a 9-cm Petri dish containing sterile Whatman paper saturated with 3 ml water. From a Petri dish containing potato dextrose agar medium containing 2% (w/v) glucose and 1.5% (w/v) agar and 7-day sporulating C.m. cultures, a plug (5 mm diameter) was stabbed out (Nemestothy and Guest, 1990). The plug was placed with the fungus side down in the center hole of the leaf piece. The Petri dish was incubated at 28° C. and after 48 h total RNA was isolated from inoculated leaves (Table 2).

TABLE 2

| In vitro infections with *Colletotrichum musae* | | | |
|---|---|---|---|
| Landrace | Hole in leaf piece | C.m. plug | Code |
| GN | + | − | GN0 |
|  | + | + | GNC |
| TG | + | − | TG0 |
|  | + | + | TGC |

*Mycosphaerella fijiensis*

Leaf material was collected at naturally infected experimental field plots of CORBANA (Corporación Bananera Nacional) in Guapiles, Costa Rica in the beginning of the rainy season (mid June). 'Grande Naine' (GN) and 'Calcutta 4' (CA) plants were selected at two different locations. One half of the youngest and second youngest leaf (not the cigar leaf) of these plants was collected in the morning, placed on dry ice, transported to Belgium on dry ice and total RNA was isolated. The remaining halves of the leaves were observed every 3 to 4 days until symptoms became visible. These data indicated that at the time of collection the leaves were indeed infected (Table 3).

Two days after collecting the leaves, corm cubes containing the meristem were dissected from the selected plants, disinfected and placed on initiation medium for transportation. Upon arrival in Belgium all cultures turned out to be contaminated by microbial infection, so the meristems were aseptically excised and regenerated into plantlets. In the winter (January), two plants of each landrace were transferred to pots in the greenhouse and one month later transferred to soil. When 4-5 months later (May) the plants had reached an acceptable height total RNA was isolated. The selected plants had been tested for the presence of BSV, CMV and potyvirus, but none of them was completely virus free (Table 3).

TABLE 3

| Plant characterization and field infections with *Mycosphaerella fijiensis* | | | | | | | | | |
|---|---|---|---|---|---|---|---|---|---|
| | | | | | Symptoms (days)[h] | | Code | | |
| | | Virus testing | | | | | Uninfected | Infected | |
| Land race | Plant code | BSV[e] | CMV[f] | PV[g] | Leaf 1[i] | Leaf 2[j] | Leaf 0[l] | Leaf 1[i] | Leaf 2[j] |
| GN | KUL2 | + | − | + | 12 | 6 | $GN_20$ | $GN_21$ | $GN_22$ |
| CA | KUL4 | + | − | + | 48 | 39 | $CA_40$ | $CA_41$ | $CA_42$ |
| CA | KUL5 | + | − | − | 84 | 75 | $CA_50$ | $CA_51$ | $CA_52$ |

[e]Banana streak virus.

[f]Cucumber mosaic virus.

[g]Potyvirus.

[h]Days (after collection of half leaves) when symptoms became visible on the remaining halves of the leaves.

[i]Leaf 1 is the youngest leaf, apart from the cigar leaf, of an infected plant.

[j]Leaf 2 is the second youngest leaf, apart from the cigar leaf, of an infected plant.

[l]Leaf 0 is the youngest leaf, apart from the cigar leaf, of an uninfected plant.

3. Software and Computer Analysis

Software

All sequence manipulations (alignments, translations, etc.) were done with the OMIGA version 1.1.3 software (Oxford Molecular Group, PLC). For quantitative measurement of nucleic acid concentrations the Biolise (Labsystems) software was employed Conserved Primer Design Forward primers and reverse primers were designed based on the alignment of conserved regions of ten PAL genes in six other plant species (Table 4).

TABLE 4

Heterologous PAL genes for conserved primer design

| Class | Plant species | GenBank accession |
|---|---|---|
| monocot | Oryza sativa | X87946 |
|  |  | X16099 |
|  | Triticum aestivum | X99705 |
| dicot | Nicotiana tabacum | AB008199 |
|  |  | AB008200 |
|  |  | X78269 |
|  | Pisum sativum | D10002 |
|  |  | D10003 |
|  | Medicago sativa | X58180 |
|  | Persea americana | U16130 |

Sequence Analysis

Homologies to the obtained sequences were searched for in GenBank (National Centre for Biotechnology Information, NCBI) with the BLAST software via internet (Altschul et al., 1990 and 1997). To compare nucleotide sequences to nucleotide sequences in the database, BLASTn (standard nucleotidenucleotide BLAST) was used against the "nr" database (GenBank+RefSeq Nucleotides+EMBL+DDBJ+PDB) with default settings except the low complexity filter. The sequences were also subjected to BLASTn searches in expressed sequence tag (EST) databases of rice, of the Rice Genome Project, and of the Global Musa Genomics Consortium.

To compare nucleotide sequences to amino acid sequences in the database, BLASTx (nucleotide query—protein db) was employed against the "nr" database with default settings except the low complexity filter.

To compare amino acid sequences to amino acid sequences in the database, BLASTp (standard protein—protein BLAST) was used together with the "nr" database and default settings except the low complexity filter. A sequence was considered to be homologous with a match in the databases if the expected E-value was below a threshold of $e^{-05}$, but each case was also evaluated individually by eye.

The identified PAL genes were checked by the domain search software interpro (Mulder et al., 2003; http://www.ebi.ac.uk/interpro/). Protein domains were also searched for with the SMART software (Schultz et al., 1998; http://smart.embl-heidelberg.de/) under default settings.

The first analysis of the cloned promoter sequences was done by querying them via the internet in the PLACE database (www.dna.affrc.go.jp/PLACE/). Repeats and long terminal repeats (LTRs) were analysed with the palindrome software (http://bioweb.pasteur.fr/seqanal/interfaces/palindrome.html).

Statistical Analysis

For the statistical evaluation of expression data collected during field evaluation of transgenic plants STATISTICA® software package (version 5, StatSoft) was employed to perform analysis of variance (ANOVA). For a valid interpretation of ANOVA two conditions have to be met: (i) variances are homogeneous across different samples, and (ii) data of the dependent variable (e.g. tissues, leaf age, etc.) fit the normal distribution within the groups (treatments). For homogeneity of variance Levene's test was used (Levene, 1960): if the resulting p-value of Levene's test was higher than 0.05, the obtained small differences in sample variances are likely to have caused by random sampling effects. Thus, the null hypothesis of equal variances was maintained and it was concluded that there is no difference between the variances in the population. If this condition was not fulfilled, data were first subjected to logarithmic [ log(x)] or square root transformations, and Levene's tests were repeated. For normality evaluation of small- or medium-scale (up to 5000) samples the Shapiro-Wilk test (Shapiro and Wilk, 1965) is regarded the most reliable: if the resulting p-value of the Shapiro-Wilk test was higher than 0.05, the null hypothesis of data normality was maintained and the parametric ANOVA was proceeded. Alternatively, the identification of outliers (see below) was used as a simple check of normality.

Once a statistically significant overall difference is determined by ANOVA, post hoc tests can typically identify the groups that are significantly different from one another. For this purpose, Duncan's multiple range test (Duncan, 1955) was used as it tolerates unequal group sizes. All the above tests are embedded in STATISTICA®, and thus were performed from within this package. The obtained results were then presented in the form of standard boxplots.

4. Nucleic Acid Manipulations

Manipulation of DNA and RNA was carried out using known methods such as those described by Sambrook et al. (*Molecular Cloning: a Laboratory Manual,* 2nd Ed., Cold Spring Harbour Laboratory Press, Cold Spring Harbour N.Y. [1989], the entire content of which is incorporated herein by cross-reference). Reagents and other material were obtained from commercial sources or as otherwise indicated.

5. Nucleic Acid Isolation

Plasmid DNA isolation was done with the Plasmid Mini Kit (Qiagen) or QIAprep Spin Miniprep Kit (Qiagen) according to the manufacturer's instructions.

Genomic DNA was isolated according to a combination of modified Dellaporta protocol (Dellaporta et al., 1983) and DNeasy Plant Mini Kit (Qiagen).

RNA was isolated from banana leaves of the C.m. inoculation experiment using the RNeasy protocol (Qiagen) and from leaves of the M.f. infection experiment using the Aljanabi protocol. Total RNA was stored in 1 mM Na-citrate, pH 6.4 (this is the composition of the RNA Storage Solution, Ambion).

RNeasy protocol: RNA was isolated using the RNeasy Plant Mini Kit (Qiagen) according to the manufacturer's instructions. The RLT buffer was supplemented with 2% (w/v) polyvinylpyrrolidone (PVP MW 10,000) and 1% (v/v) β-mercaptoethanol.

Modified Aljanabi method: A genomic DNA isolation protocol (Aljanabi and Martinez, 1997) that resulted in high amounts of coisolated RNA was modified for RNA isolation. The extraction buffer was supplemented with 2% (w/v) PVP and 1% (v/v) β-mercaptoethanol, and RNA was extracted with chloroform, then precipitated with 6 M LiCl to separate it from the DNA in solution.

6. Quantitation of Nucleic Acids

DNA concentrations were determined using PicoGreen reagent (Molecular Probes). After excitation at 480 nm, the fluorescence was measured at 520 nm in a SPECTRAFluor Plus microtiterplate reader (Tecan). Data were analyzed with Biolise software (Labsystems).

RNA concentrations were determined using SYBR Green II reagent (Molecular Probes) (Schmidt and Ernst, 1995). After excitation at 495 nm, the fluorescence was measured at 530 nm in SPECTRAFluor Plus microtiterplate reader. Data were analyzed with Biolise software.

7. DNase I Treatment of RNA

RNA to be used in RT-PCR was treated with DNase I in order to remove DNA contamination and thus to avoid false positive results.

For DNase I treatment, 20 μg total RNA and 20 U DNase I (Ambion) was incubated in 1×Mn-buffer (660 μM $MnCl_2$ and 10 mM Tris-HCl, pH 7.8) at 37° C. for 30 min. Next, EDTA was added to a final concentration of 2.5 mM to avoid degradation of the RNA in the presence of divalent cations during the heat inactivation step, and the enzyme was inactivated by incubation at 75° C. for 5 min. DNase I treatment was verified by performing PCR with ACTIN primers. Negative PCR results indicated total DNA removal.

8. Amplification Reactions 8.1. PCR. The following parameters are specified for our standard PCR protocol:

Enzyme: 0.025 U/μL Taq DNA polymerase (Qiagen) or 0.025 U/μL Hot Star Taq DNA polymerase (Qiagen)
Buffer: 1×PCR buffer (1.5 mM $MgCl_2$) (Qiagen)
dNTPs: 200 μM
Primers: 0.5 μM Calculation of melting temperatures of primers: $T_m = 2 (\#AT) + 4 (\#GC)$ Primer sequences are always written in 5' to 3' direction. The forward primers have the same sequence as the mRNA; the reverse primers have the reverse complementary sequence.

Template: 0.25 ng/μL DNA

| Program: | initial denaturation | 94° C. | 02'00" or |
| --- | --- | --- | --- |
| | denaturation | 95° C. | 15'00" for Hot Star Taq |
| | denaturation | 94° C. | 00'15" |
| | primer annealing | 54 to 58° C. | 00'20" (temperature depending on primers) |
| | primer extension | 72° C. | 00'20" to 1'00" (time depending on expected product size) |
| | cycle number | x 35 (starting from denaturation) | |
| | final extension | 72° C. | 02'00" |
| Equipment: | Eppendorf Mastercycler Gradient (or Perkin-Elmer Gene Amp 9700) | | |

8.2 Two-step RT-PCR. In two-step RT-PCR, reverse transcription using a poly(dT) primer was carried out first and the resulting total cDNA was added to a separate PCR-reaction.

| Reaction components: | 1 x | RT buffer (Qiagen) |
| --- | --- | --- |
| | 500 μM | dNTPs |
| | 1 μM | $dT_{12-18}$ primer |
| | 1 U/μL | ANTI-RNase (Ambion) to inhibit RNases |
| | 0.2 U/μL | Omniscript reverse transcriptase (Qiagen) |
| | 100 ng/μL | DNase-treated total ARNA (heated at 65° C. for 5 min to denature RNA) |
| Reaction conditions: | incubation at 37° C. for 1 h | |

The total cDNA was used as template in PCR (7.5 ng/μL RNA-equivalent) using Hot Star Taq DNA polymerase in the second step:

| Enzyme: | 0.025 U/μL Hot Star Taq DNA polymerase |
| --- | --- |
| Buffer: | 1 x PCR buffer (1.5 mM $MgCl_2$) |
| dNTPs: | 300 μM |
| Primers: | 0.5 μM (PALF2-PALR1, Table 6) |
| Template: | 7.5 ng DNase-treated RNA |

| Program: | initial denaturation | 95° C. | 15'00" |
| --- | --- | --- | --- |
| | denaturation | 94° C. | 00'15" |
| | primer annealing | 53° C. | 00'20" |
| | primer extension | 72° C. | 00'20" |
| cycle number | x 35 (ACTIN x 24) | | |
| | final extension | 72° C. | 02'00" |
| Equipment: | Mastercycler Gradient (Eppendorf) | | |

8.3 Semi-Quantitative Duplex RT-PCR (SQD RT-PCR)

In order to interpret RT-PCR results quantitatively, amplification has to be in the linear range. The linear range of amplification was determined by dividing an RT-PCR reaction over several aliquots and analyzing each of them after different cycle numbers. The optimized parameters for the ACTIN primers in SQD RT-PCR were: 150 ng template, 24-28 cycles, and 51-56° C. annealing temperature.

| Enzyme: | Hot Star Taq DNA polymerase | | |
| --- | --- | --- | --- |
| Primers: | ACTINF-ACTINR plus PALF2-PALR1 | | |
| Program: | reverse transcription | 60° C. | 30'00" |
| | initial denaturation | 95° C. | 15'00" |
| | denaturation | 94° C. | 00'15" |
| | primer annealing | 51° C. | 00'20" |
| | primer extension | 72° C. | 00'20" |
| cycle number | x 36 (ACTIN: x 28) | | |
| | final extension | 72° C. | 10'00" |
| Equipment: | Mastercycler Gradient | | |

Total cDNA was synthesized according to the two-step RT-PCR. Then, the linear amplification range was determined for the ACTIN primers (see above) and the specific PAL primers. This was done based on differences in intensity of amplification products from different templates, which indicates the linear range. Duplex RT-PCR was then performed, but first only the primer pair with the highest cycle number needed for linear amplification was added. After the required number of cycles, the other primer pair was also added to the PCR reaction. The final concentration of both primer pairs in the reaction was 0.5 μM.

For every SQD RT-PCR, the simplex reactions (one with ACTIN primers and one with the PAL-specific primers) were also performed in parallel as a control for the duplex RT-PCR. Relative band intensities (estimated by eye or measured by the ImageJ software version 1.37k, NIH, USA) of the separate reactions were usually similar to those of the duplex reaction (data not shown). Rates of PAL gene expression were always considered relative to that of ACTIN, with both amplifications in their respective linear range.

For group-specific SQD RT-PCR the following parameters were employed:
Enzyme: Hot Star Taq DNA polymerase
Primer combinations: PALGNF1-PALGNR1, PALGNF2-PALGNR2, PALGNF3-PALGNR3, PALCAF4-PALCAR4 (see Table 10)

| Program: | reverse transcription | 60° C. | 30'00" | |
| --- | --- | --- | --- | --- |
| | initial denaturation | 95° C. | 15'00" | |
| | denaturation | 94° C. | 00'15" | |
| | primer annealing | 67.5° C. | 00'20" | group1 |
| | | 67.0° C. | | group2 |
| | | 62.0° C. | | group3 |
| | | 63.0° C. | | group4 |
| | primer extension | 72° C. | 00'20" | |
| cycle number | x 35 group 1 and 4 (ACTIN: x 30) | | | |
| | x 34 group 2 | | | |
| | x 40 group 3 | | | |
| | final extension | 72° C. | 02'00" | |
| Equipment: | Mastercycler Gradient | | | |

9. Gene Walking by TAIL-PCR

TAIL-PCR (Thermal Asymmetric Interlaced PCR) is a method that consists of three consecutive PCR rounds with arbitrary (degenerate) primers and nested gene-specific primers (Liu and Huang, 1998; Terauchi and Kahl, 2000).

Primer Design

The forward primer in each round was an arbitrary degenerate primer (AD1, AD2 or AD3) or an arbitrary primer (RA1 to RA5). The nested reverse primers were based on the group 2-specific (GS) sequences: PALCAR2 or PAL2TAILR1 in the primary PCR, PALGNR2 or PAL2TAILR2 in the secondary PCR, and PAL2IR or PAL2TAILR in the tertiary PCR of the first and second elongation step, respectively (Table 5).

TABLE 5

TAIL primers

| Name | Orientation | Sequence (5' - 3') | $T_m$ (° C.) | Position | SEQ ID NO: |
|---|---|---|---|---|---|
| AD1 | forward | SCA CNT CST NGT NTC T | 49 | n.a. | 5 |
| AD2 | forward | NGT CGA SWG ANA WGA A | 46 | n.a. | 6 |
| AD3 | forward | WGT GNA GWA NCA NAG A | 45 | n.a. | 7 |
| RA1 | forward | GAG CTT GAA C | 30 | n.a. | 8 |
| RA2 | forward | ATC TCG CTA G | 30 | n.a. | 9 |
| RA3 | forward | CTG ATC CAT G | 30 | n.a. | 10 |
| RA4 | forward | TCC ACT GGC A | 32 | n.a. | 11 |
| RA5 | forward | GGT ACT CCA C | 32 | n.a. | 12 |
| PALCAR2 | reverse | TTC CCG ATG GCG GCG AC | 58 | 308-324* | 13 |
| PALGNR2 | reverse | GAT GGA CTT GGT GGA GGC G | 62 | 166-184* | 14 |
| PAL2IR | reverse | TCC TGC TTC GGC TTC TGC AGT | 66 | 88-108* | 15 |
| PAL2TAILR1 | reverse | ACC CTA ACC GCC GAG TGG | 60 | 572-589** | 16 |
| PAL2TAILR2 | reverse | CTG CCG TTC GCA TGG ACG | 60 | 386-403** | 17 |
| PAL2TAILR | reverse | CTT CAA CCA CTG GAT CGG TC | 62 | 199-218** | 18 |

Abbreviations: S = G + C, N = A + G + C + T, W = A + T, n.a.: not applicable.
*based on the sequence alignment in FIG. 4,
**distance from the AD2 primer in the first-step TAIL-PCR Protocol AD or RA (forward) primers: 2 M GS (reverse) primers: 0.15 µM Primary PCR Primer combinations: AD1/2/3+PALGNR2 (1$^{st}$ step), RA1/2/3/4/5+PAL2TAILR1 (2$^{nd}$ step)

| Program: | 94° C. | 02'00" | |
| | 94° C. | 01'00" | |
| | 64° C. | 00'20" | |
| | 72° C. | 03'00" | x5 |
| | 94° C. | 01'00" | |
| | 27.5° C. | 03'00" | |
| | 72° C. | 03'00" | |
| followed by 15 cycles of: | 94° C. | 00'30" | |
| | 64° C. | 01'00" | |
| | 72° C. | 03'00" | x2 |
| | 94° C. | 00'30" | |
| | 44° C. or 42° C. | 01'00" (for AD or RA primers, respectively) | |
| | 72° C. | 03'00" | |
| followed by: | 72° C. | 03'00" | |

Enzyme: double amount of Taq DNA polymerase in primary PCR

Template (1$^{st}$ step): DNA GN, DNA CA, pPALGN1 (10$^{-5}$ dilution), pPALCA2 (10$^{-5}$ dilution), pPALGN3 (10$^{-5}$ dilution), pPALCA4 (10$^{-5}$ dilution) (see Table 9 & footnotes thereof)

Template (2$^{nd}$ step): DNA GN, DNA CA, pPAL2AD2CA07 (10$^{-5}$ dilution, see Table 11), pPAL4AD1GN12 (10$^{-5}$ dilution, group 4-specific control)

Secondary PCR

Primer combinations: AD1/2/3+PALCAR2 (1$^{st}$ step), RA1/2/3/4/5+PAL2TAILR2 (2$^{nd}$ step)

| Program: | 12 cycles of: | | |
| | 94° C. | 00'30" | |
| | 64° C. | 01'00" | |
| | 72° C. | 03'00" | x2 |
| | 94° C. | 00'30" | |
| | 44° C. or 42° C. | 01'00" (for AD or RA primers, respectively) | |
| | 72° C. | 03'00" | |
| followed by: | 72° C. | 03'00" | |
| Template: | primary PCR 100x diluted | | |

Tertiary PCR

Primer combinations: AD1/2/3+PAL2IR (1$^{st}$ step), RA1/2/3/4/5+PAL2TAILR (2$^{nd}$ step)

Program: 10 cycles as in secondary PCR:

Template: secondary PCR 100× diluted

10. PCR Cloning and Clone Analysis

PCR products were directly cloned using the TOPO TA Cloning Kit or the TOPO TA Cloning Kit for Sequencing (both Invitrogen) according to the manufacturer's instructions. Large PCR products (>3 kb) were directly cloned using the TOPO XL PCR Cloning Kit (Invitrogen) according to the manufacturer's instructions.

Blue-white screening was done according to Maas (1999). X-Gal was spread onto overnight-grown plates instead of adding the substrate into the agar medium. Blue color appeared after 3 h when using an X-Gal concentration of 500 µg/mL.

For PCR clone analysis, loading dye (0.25×) was directly added to the PCR reaction (Menossi et al., 2000).

11. Nucleotide Sequencing

Clones were custom sequenced at the Genetic Service Facility of the Flemish Institute for Biotechnology (VIB, Wilrijk, Belgium). After template or plasmid preparation, sequencing was performed using the ABI PRISM® Big-Dye™ Terminator Cycle Sequencing kit (Applied Biosystems, Foster City, Calif., USA) and reactions were run on a Applied Biosystems 3730 DNA Analyzer.

12. Vector Construction

Figure 1A:
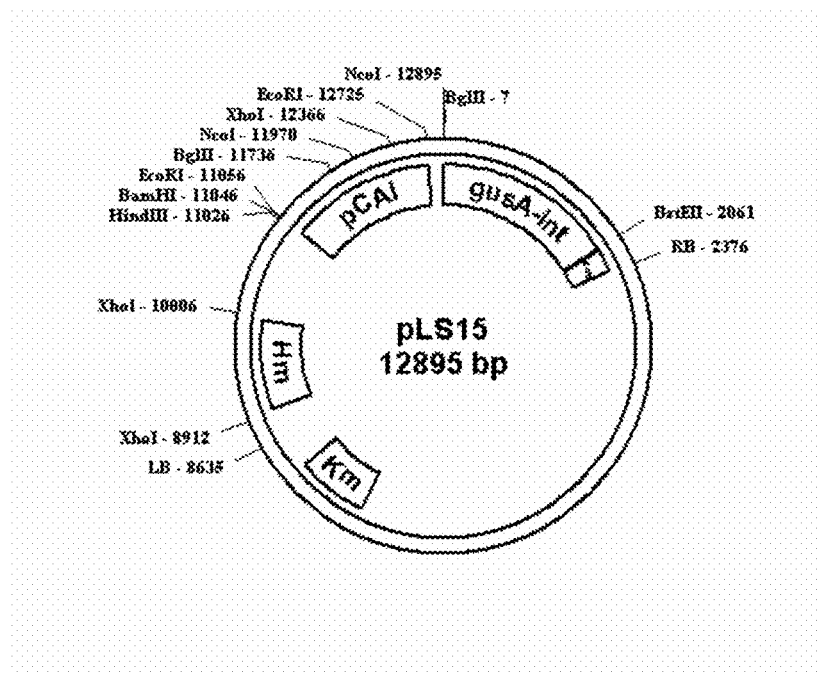
FIG. 1 represents the expression vectors for use in plant transformations, comprising promoter sequence SEQ ID NO:1 (A-pCAL) or SEQ ID NO:3 (B-pCAS).
Figure 1B:
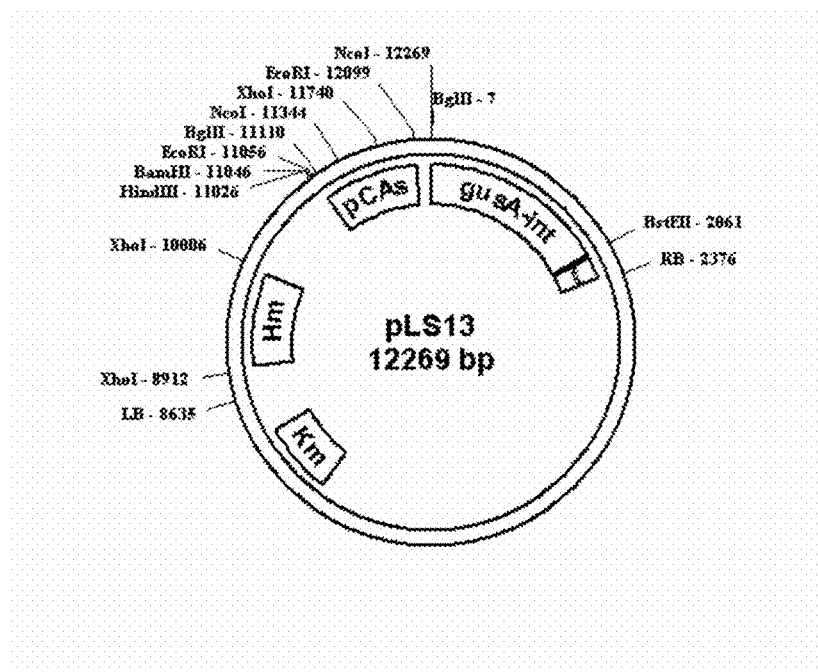
Figure 2A:
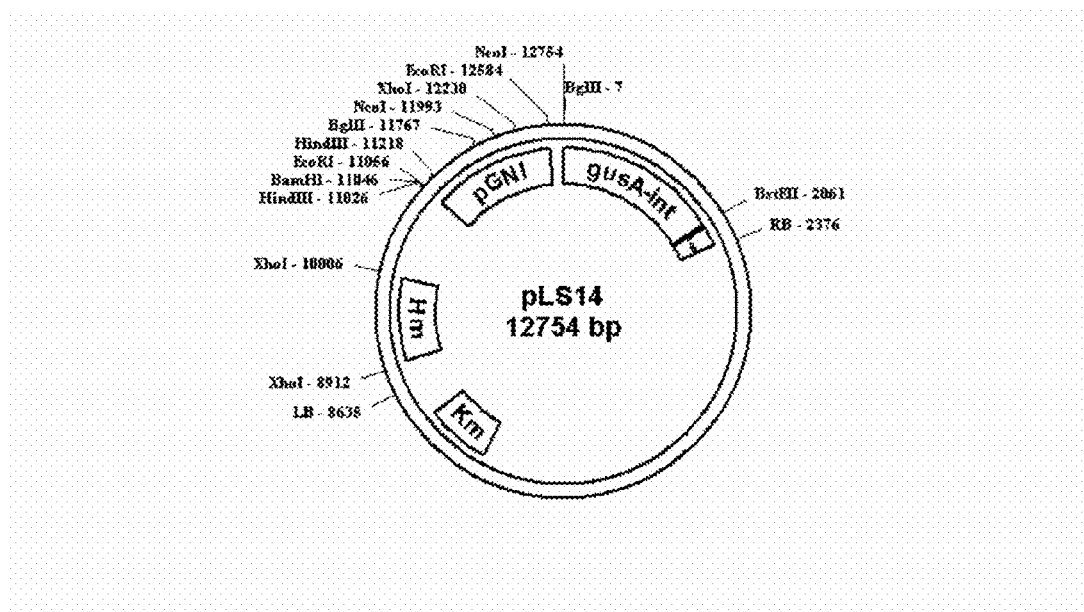
FIG. 2 represents the expression vectors for use in plant transformations, comprising promoter sequence SEQ ID NO:2 (A-pGNL) or SEQ ID NO:3 (B-pGNS).
Figure 2B:
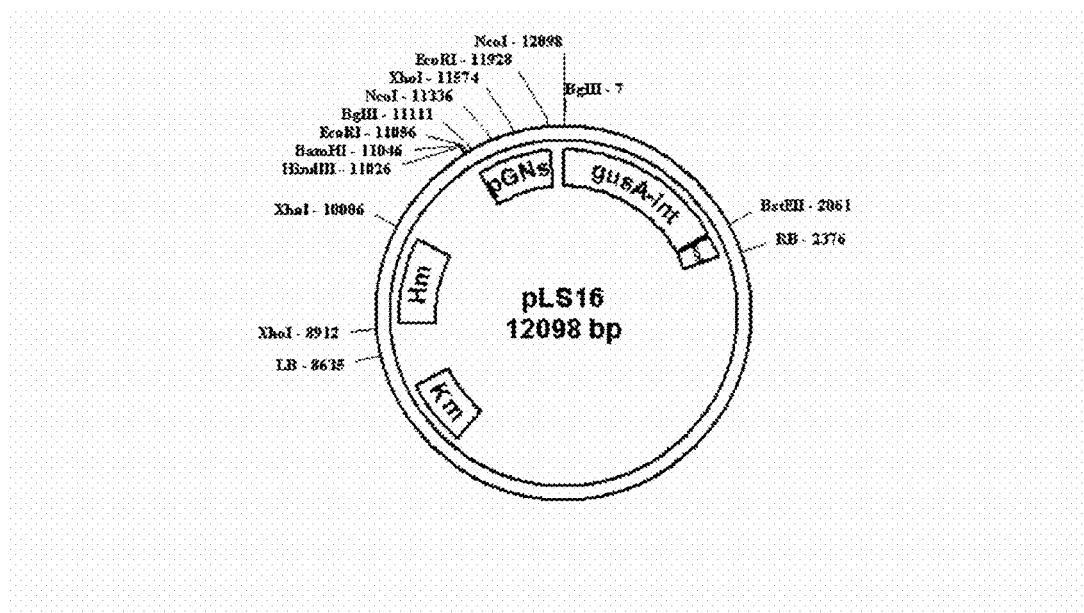

The binary expression vector pCAMBIA1391z (11,226 bp, GenBank accession No. AF234312) served as common vector, which ensured that all constructs had the same backbone and T-DNA, except for the inserted promoters. pCAMBIA1391z contains a promoterless intron-containing gusA$^{INT}$ gene as reporter gene and a chimeric hygromycin phosphotransferase (hpt) gene as selectable marker gene. An EcoRI site (sequence position 11,056) served as insertion point for four banana promoter sequences to generate the vectors pLS13-16 (FIGS. 1 & 2). For control promoters, a double digest of either BamHI/HindIII (Cauliflower Mosaic Virus 35S RNA and maize ubi1 promoters, pLS23 and pLS25, respectively) or NcoI/HindIII (*Arabidopsis* plant defensin promoter, pLS26) was employed in the same multicloning region (between sequence positions 11,026-11,061). Recombinant clones were verified by nucleotide sequencing (as above) and correct clones were transformed by electroporation into the *Agrobacterium tumefaciens* strain EHA105. In addition, for *Arabidopsis* transformation, another five uid-A$^{INT}$ constructs (pLS35-39, Table 13) were prepared in the pFAJ3160 vector (De Bolle et al., 2003), which contains a chimeric bar selectable marker gene for plant resistance to glufosinate herbicides instead of the hpt selectable marker gene. pFAJ3160 vector also contains the 35S control promoter::uidA$^{INT}$ fusion.

For transient gene expression assays via particle bombardment pLS7-8 (pCAS and pGNL) and pLS11-12 (pCAL and pGNS) were prepared in pCAMBIA1291z (11,378 bp, GenBank accession No. AF234295) which is identical to pCAMBIA1391z except for the bacterial selectable marker gene. pAHC27 (Christensen and Quail, 1996) served as positive control, which contained the same but intronless uidA gene under control of the maize ubi1 promoter.

13. Plant Transformations

Banana

Transient transformation of banana embryogenic cells (see above) was performed by particle bombardment in a homemade particle inflow gun as described by Sági et al. (1995). Transient reporter gene expression was determined by histochemical assay for GUS expression (see below).

Transgenic plants in banana were generated by *Agrobacterium*-mediated transformation of embryogenic cell suspensions, followed by selection of transgenic colonies and plant differentiation therefrom according to standard protocols (Pérez-Hernández et al., 2006). *Agrobacterium tumefaciens* strain EHA105 containing individual promoter::gusA$^{INT}$ pLS vectors were grown in YEP medium (10 g/L Bacto yeast extract, 10 g/L Bacto peptone, 5 g/L NaCl, pH 7.5) supplemented with the appropriate antibiotics for 20-24 h. Bacterial cultures were diluted to an OD$_{600}$ of approximately 0.4 units and then transferred to antibiotic-free ZZ medium (pH 5.6) containing 200 µM acetosyringone (AS) for induction.

Two-hundred µL embryogenic suspension cells of the commercial dessert banana cultivar 'Grande Naine' (GN, cell lines 128f and 128h) at 33% settled cell volume (±50 mg fresh weight cells) were mixed with 1 mL of induced agrobacteria in a well of a 24-well plate and incubated in the dark at 25° C. on a rotary shaker at 25 rpm for 6 h. Following 1 week of cocultivation on ZZ medium (pH 5.6) supplemented with 200 µM AS, the mesh with cells was transferred to selective ZZ medium (pH 5.8) containing 50 mg/L hygromycin and 200 mg/L timentin and subcultured every 2 weeks for 2 to 3 months. Further regeneration of individually picked independent transgenic cell colonies to complete plants was done as described previously (Dhed'a et al., 1991; Sági et al., 1995).

Other Plant Species

Rice transformation was carried out by *Agrobacterium*-mediated cocultivation of mature seed-derived embryogenic calli of the standard *japonica* cultivar 'Nipponbare' as described by Sallaud et al. (2003). Selected primary regenerants were subjected to histochemical GUS staining.

*Arabidopsis* plants (ecotype Col0, see 1.1.1.) in early flowering stage were transformed by following the in planta procedure of Clough and Bent (1998). Seeds were harvested, sown in soil followed by selection with herbicide (Basta) spraying and histochemical GUS staining.

Tobacco (*Nicotiana benthamiana*) was transiently transformed by *Agrobacterium* infiltration of fully grown leaves on potted plants. Two days after infiltration, leaves were detached and stained for histochemical GUS assay.

14. Analysis of Transgenic Plants

PCR

To check if the transgene was present in banana plants, PCR (see 2.5.1.) was performed on DNA templates isolated from in vitro plantlets. The primers (forward: 5'-CTTCTA-CACAGCCATCGGTC-3' (SEQ ID NO:19) and reverse: 5'-GACCTGCCTGAAACCGAACTG-3') (SEQ ID NO:20) amplified a 668-bp fragment of the hygromycin phosphotransferase (hpt) gene that had been employed as selectable marker gene.

The PCR cycling program was: 2 min at 95° C., (30 sec at 95° C., 30 sec at T$_{ann}$, 1 min at 68° C.)×3 at each T$_{ann}$ of 68° C., 66° C., 64° C. and 62° C., (30 sec at 95° C., 30 sec at 60° C., 1 min at 68° C.)×30, and finally 2 min at 68° C. prior to storing at 4° C.

Histochemical GUS Assay

Staining solution containing 1 mg/mL X-Gluc (5-bromo-4-chloro-3-indolyl-(3-D-glucuronic acid) substrate was prepared as described by Mendel et al. (1989). Plant tissues (leaf, root, flower, peduncle, pulp, peel and seed) from diverse plant species (banana, rice, *Arabidopsis* and *N. benthamiana*) were incubated in the staining solution for 3 h at 37° C. and kept at room temperature overnight before taking photographic images. The staining solution was usually supplemented with the zwitterionic detergent CHAPS (3-[(3-cholamidopropyl)-dimethylammonio]-1-propanesulfonate) at 0.2% (w/v) to enhance substrate penetration into plant (mainly banana leaf) tissues.

Quantitative GUS Enzyme Activity Assay

GUS enzyme activity in transgenic banana plants was determined by a standard quantitative fluorometric assay (Cervera, 2004). The method consisted of total protein extraction in 50 mM sodium-phosphate buffer (pH 7) containing 10 mM sodium-EDTA, 20% (v/v) methanol, 2% (w/v) PVP (MW 10,000), 0.1% (w/v) sodium lauryl sarcosine, 0.1% (v/v) Triton X-100 and 0.07% (v/v) β-mercaptoethanol followed by the determination of protein concentration with Bradford assay using bovine serum albumin as calibration standard. GUS activity was then measured with 4-methylumbelliferyl-β-D-glucuronide substrate, and the fluorescent 4-methylumbelliferone as calibration standard. After 1 h of incubation at 37° C., reactions were stopped with 0.2 M sodium carbonate solution (pH 9.5), and fluorescence was measured in the SPECTRAFluor Plus microtiterplate reader. Specific GUS enzymatic activity was expressed in pmoles MU/h/µg total protein.

15. Transgenic Field Evaluation

In total, 145 banana events, i.e. 126 transgenic events (of which 66 events contained one of the four banana PAL promoters, and 60 independent events contained each one of the three control promoters) and 20 untransformed controls (also regenerated in vitro from the same GN cell suspensions, see above) were transferred to the field in Costa Rica after obtaining permission from the national biosafety authority. Of each event, at least six plants were planted in miniblocks of three plants distributed in two main blocks that were treated and not treated with fungicides. The position of miniblocks was randomized within the two main blocks. In addition, a control experiment was designed for 54 (82%) of the 66 transgenic banana PAL promoter events in a screenhouse to test whether fungicide treatment alone had an effect on promoter activity. Both the field as well as the screenhouse were regularly inspected by an independent biosafety auditor.

Transgenic lines containing constructs pLS13-16, pLS 23 and pLS25-26 as well as the untransformed control lines were coded alphabetically (A-H) to ensure blind and unbiased evaluations in the field. Samples collected in different seasons from different parts (one or more leaves, roots, pseudostems, peduncles, pulp and peel) of the plants were transferred into labelled aluminium bags and immediately frozen on dry ice in the field. Frozen samples were stored on dry ice in a −20° C. freezer until transportation. Upon arrival to Belgium, all samples were stored in −80° C. freezers until fluorescent or histochemical GUS assays.

Example 1

Figure 3:
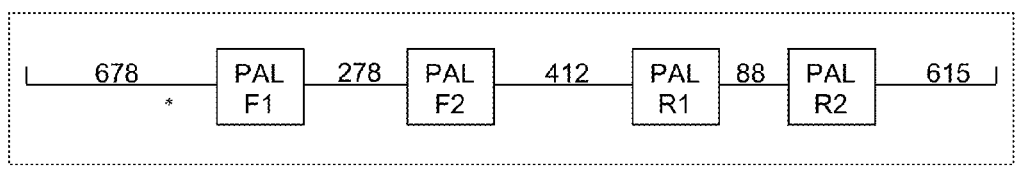
FIG. 3 shows the schematic position of conserved PAL primers on the coding sequence. Intron position is indicated by asterisk.

Identification and Cloning of PAL Genes and Promoters in Banana 1.1. Design of Conserved Primers Conserved primers were designed based on nucleotide sequences of ten PAL genes from six plant species (see Table 4). Alignments of conserved regions in the ten PAL genes analysed allowed the design of four conserved PAL primers. Based on these alignments two forward primers (PALF1 and PALF2) and two reverse primers (PALR1 and PALR2) were designed as summarized in Table 6. The expected product sizes after (RT-)PCR with all combinations of these primers are outlined in Table 7 together with their approximate position on the PAL coding region (FIG. 3).

TABLE 6

Sequence and melting temperature ($T_m$) of conserved PAL primers

| Name | Sequence (5' - 3') | $T_m$ (° C.) | SEQ ID NO: |
|---|---|---|---|
| PALF1 | TCK YTK TCY TAC ATT GCY GG | 60.0 | SEQ ID NO: 21 |
| PALF2 | AAG YTG AAG CAY CAY CCH GG | 62.0 | SEQ ID NO: 22 |
| PALR1 | TT GAA VCC RTA RTC CAA GCT | 58.0 | SEQ ID NO: 23 |
| PALR2 | GA GTT SAC RTC YTG GTT GTG | 60.0 | SEQ ID NO: 24 |

Abbreviations: K = G + T, Y = C + T, H = A + C + T, V = A + G + C, R = A + G, S = G + C

TABLE 7

Expected (RT-)PCR product sizes (bp) obtained with conserved PAL primers

| Primer | PALR1 | PALR2 |
|---|---|---|
| Primer | 750 | 858 |
|  | no introns | no introns |
| PALF2 | 452 | 560 |
|  | no introns | no introns |

1.2. (RT-)PCR Analysis with Conserved PAL Primers

PCR analysis: All primer combinations, except for PALF1-PALR2, gave products of the expected size. Even if the annealing temperature was lowered to 47° C. this primer combination remained negative (data not shown).

RT-PCR analysis: For the C.m. inoculations, all templates yielded the expected 452 bp band with primer combination PALF2-PALR1. Products from inoculated leaves were more intense than bands from control leaves, with TG having been more intensely induced than GN (data not shown). For the M.f. infections, product sizes were also correct, but their intensities were irregular among infected leaves with CA being in general more intense than GN (data not shown). These observations confirmed prior knowledge that M.f. infections are not reproducible, and C.m. inoculations, on the other hand, result in detectable induction of PAL gene expression in leaves of banana landraces.

Semi-quantitative duplex RT-PCR analysis (SQD RT-PCR): For the M.f. infections, most templates yielded the expected 452 bp band with primer combination PALF2-PALR1 (data not shown). Products from infected leaves were more intense than those from control leaves (data not shown). Considering the intensity ratios with ACTIN, PAL appears to be weakly induced by infection in GN and more strongly induced in CA. This result confirms the previous RT-PCR experiments.

The PAL (RT-)PCR products were cloned from all samples and sequenced to identify the member(s) of the gene family (Table 8). In total, 20 sequences were obtained from GN (14 from cDNA and 6 from gDNA) and 17 sequences from CA (9 from cDNA and 8 from gDNA). These 37 clones were grouped according to their nucleotide sequence. Clones PAL-CA-05, PAL-CA-15, PAL-CA1-09, PAL-GN2-07 and PAL-GN-03 were not included in the grouping because they were significantly different from the groups or their sequence quality was not good enough. Among the remaining 32 clones, four groups of PAL sequences could be distinguished; each contained subgroups, which differed only by a few nucleotides (Table 9). The sequences of groups 1-4 were all homologous to PAL genes from other plants. The homology between the four groups ranged from 86% to 95% at the nucleotide level (FIG. 4) and 95% to 97% for the translated sequences. Groups 1, 2 and 4 contained fragments obtained from infected leaves (Table 9).

TABLE 8

Overview of sequenced clones from (RT-)PCR reactions

| Template | Code clone | Template | Code clone |
|---|---|---|---|
| RNA GN20 | PAL-GN0-01 | RNA CA40 | — |
| RNA GN21 | PAL-GN1-02 | RNA CA51 | PAL-CA1-07 |
|  | PAL-GN1-03 |  | PAL-CA1-09 |
|  | PAL-GN1-10 |  |  |
|  | PAL-GN1-11 |  |  |
|  | PAL-GN1-12 |  |  |

TABLE 8-continued

Overview of sequenced clones from (RT-)PCR reactions

| Template | Code clone | Template | Code clone |
|---|---|---|---|
| RNA GN22 | PAL-GN2-01 | RNA CA52 | PAL-CA2-01 |
|  | PAL-GN2-02 |  | PAL-CA2-03 |
|  | PAL-GN2-07 |  | PAL-CA2-11 |
|  | PAL-GN2-08 |  | PAL-CA2-19 |
|  | PAL-GN2-11 |  | PAL-CA2-24 |
|  | PAL-GN2-12 |  | PAL-CA2-26 |
|  | PAL-GN2-15 |  | PAL-CA2-29 |
|  | PAL-GN2-16 |  |  |
| DNA GN | PAL-GN-01 | DNA CA | PAL-CA-02 |
|  | PAL-GN-03 |  | PAL-CA-04 |
|  | PAL-GN-05 |  | PAL-CA-05 |
|  | PAL-GN-06 |  | PAL-CA-06 |
|  | PAL-GN-15 |  | PAL-CA-07 |
|  | PAL-GN-17 |  | PAL-CA-08 |
|  |  |  | PAL-CA-09 |
|  |  |  | PAL-CA-15 |

TABLE 9

Grouping of PAL sequences

| Group | Code clones |
|---|---|
| Group 1A | PAL-CA2-03, -11, -29, PAL-CA-04 |
| Group 1B | PAL-CA1-07, PAL-CA2-19, -24, -26 |
| Group 1C | PAL-GN1-12[1], PAL-GN-05, -15, -17 |
| Group 1D | PAL-CA-08, -09 |
| Group 2A | PAL-GN1-10, PAL-GN2-02, -08, -11 |
| Group 2B | PAL-GN2-15, -16 |
| Group 2C | PAL-GN2-12, PAL-CA2-01[2] |
| Group 2D | PAL-GN1-11, PAL-GN2-01 |
| Group 3A | PAL-CA-02, -07 |
| Group 3B | PAL-GN0-01[3], PAL-GN-06 |
| Group 3C | PAL-GN-01 |
| Group 4A | PAL-GN1-02, -03 |
| Group 4B | PAL-CA-06[4] |

[1] Clone representing group 1 and its plasmid is referred to as pPALGN1.
[2] Clone representing group 2 and its plasmid is referred to as pPALCA2.
[3] Clone representing group 3 and its plasmid is referred to as pPALGN3.
[4] Clone representing group 4 and its plasmid is referred to as pPALCA4.

Group-Specific Semi-Quantitative Duplex RT-PCR (SQD RT-PCR)

Group-specific primers were designed for PAL groups 1 to 4 (Table 10, FIG. 4).

TABLE 10

Group-specific PAL primers for SQD RT-PCR

| Group | Name | Sequence (5' - 3') | $T_m$ (° C.) | Position* | Size (bp) | SEQ ID No: |
|---|---|---|---|---|---|---|
| Group 1 | PALGNF1 | TCA CGA GCA AGA CCC GCT G | 62 | 73-91 | 112 | 25 |
|  | PALGNR1 | GAT GGA CTT GGT GGC GGA G | 62 | 166-184 |  | 26 |
| Group 2 | PALCAF2 | GCT CCA CGA GCA AGA CCC AC | 66 | 70-89 | 255 | 27 |
|  | PALCAR2 | TTC CCG ATG GCG GCG AC | 58 | 308-324 |  | 28 |
| Group 3 | PALGNF3 | CCA CGA AGT CCA TCG AAC GT | 62 | 171-190 | 222 | 29 |
|  | PALGNR3 | AAA GGT TCG AGG GGA GCC CA | 64 | 373-392 |  | 30 |
| Group 4 | PALCAF4 | CCT CGA CGG AAG CTC GTT T | 60 | 34-52 | 313 | 31 |
|  | PALCAR4 | GGA GAA CTG GGC GAA CAT C | 60 | 328-346 |  | 32 |

*based on the sequence alignment in FIG. 4

RT-PCR conditions (e.g. annealing temperature) were optimized for group-specific primers to amplify only fragments of their group. The results of group-specific (SQD) RT-PCR analysis are summarized as follows:

Group 1: For both GN and CA, slight induction in the youngest leaf but equal expression or downregulation by infection in the older leaf (data not shown).

Group 2: For GN, slight induction in the youngest leaf and equal expression in the older leaf. Strong induction by infection for CA (data not shown).

Group 3: For GN, slight induction in the youngest leaf but downregulation by infection in the older leaf. Downregulation by infection also for CA (data not shown).

Group 4: Slight induction by infection for both GN and CA (data not shown).

Thus, RT-PCR confirmed the inducible character of groups 2 and 4, while group 1 and, as expected, group 3 were not inducible or were even downregulated upon infection. In groups 2 and 4, a significantly stronger signal was observed for the infected samples compared to the control samples. The high specificity of the primers was shown by the fact that primers only bound (and specifically amplified) to the original clone of the group they are derived from, while reactions with the other specific control plasmids were negative. Moreover, two more RT-PCR products, one from $CA_40$ and one from $CA_51$ that had been amplified with primers specific for group 4 were sequenced and they were 100% identical to the original group 4 sequence (data not shown). This also indicates that the sequence differences between the groups are real and not caused by polymerase misincorporations or sequencing errors.

1.3. (RT-)PCR Analysis with Conserved PAL Primers

Group 2 was selected to isolate regions upstream of the known PAL sequences, including the promoter. Several approaches were tried; however, neither Inverse-PCR (Pang and Knecht, 1997), nor Anchored-PCR (Pérez Hernández, 2000) yielded clear bands larger than 1 kb. In contrast, TAIL-PCR (Thermal Asymmetric Interlaced PCR), a method that consists of three PCR rounds with arbitrary degenerate (AD) primers and nested gene-specific primers (Liu and Huang, 1998; Terauchi and Kahl, 2000), gave satisfying results.

First Elongation Step by TAIL-PCR

All reactions with the AD3 forward primer resulted in a smear, and useful products were obtained in the tertiary PCR only with the AD2 primer. The reverse primers were group-specific because only the corresponding group 2 plasmid produced amplification products of ca. 2.4 kb, while the specific control plasmids gave the expected negative results. Two products of 2.4 kb were cloned and sequenced (Table 11). These TAIL-PCR products were group-specific as the sequences overlapped and were identical there with the sequence of group 2. The maximum distance reached upstream of the translational start codon was 361 bp for GN and 366 bp for CA. Both sequences were almost identical apart from a 6 bp deletion in GN.

TABLE 11

Results of first elongation step by TAIL-PCR

| Band | Size (kb) | Code clone | Sequenced from end | Size sequenced region (bp) |
|---|---|---|---|---|
| PAL2AD2GN | 2.4 | PAL2AD2GN01 | 5' | 417 |
|  |  | PAL2AD2GN02 | 3' | 680 |
|  |  | PAL2AD2GN03 | 3' | 544 |
| PAL2AD2CA | 2.4 | PAL2AD2CA07* | 5' | 720 |
|  |  | PAL2AD2CA08 | 5' | 392 |
|  |  | PAL2AD2CA11 | 5' | 608 |

*used as group 2-specific control plasmid (p07) in the second elongation step of TAIL-PCR Second Elongation Step by TAIL-PCR A second step of TAIL-PCR was done in order to elongate the sequence further upstream. The nested reverse primers were based on the group-specific sequences obtained in the first elongation step of TAIL-PCR: PAL2TAILR1 for the primary PCR, PAL2TAILR2 for the secondary PCR, and PAL2TAILR for the tertiary PCR. Since the forward AD primers in combination with these reverse primers resulted in a smear, further arbitrary primers (RA1 to RA5) were used instead (Table 5).

Useful products were obtained in the tertiary PCR only with the RA1, RA3 and RA4 primers. The reverse primers proved again group-specific because only the corresponding group 2 plasmid (but not the group 4-specific one) produced amplification products, except for RA3 where it was negative (data not shown). Three products of 1.1 to 3.0 kb were cloned and sequenced (Table 12). The two clones obtained from the 2TAIL01GN product contained the RA1 primer on both ends, so this was a misprimed sequence. The other products were bordered by the correct primer sequences and they were group 2-specific because the sequence upstream of the PAL2TAILR primer overlapped (219 bp and 214 bp for CA and GN, respectively) and was identical there with the products of the previous elongation TAIL-PCR. For 2TAIL16GN, approximately 190 bp in the middle were not reached, while 2TAIL12CA was fully sequenced (see below).

TABLE 12

Results of second elongation step by TAIL-PCR

| Band | Size (kb) | Code clone | Size sequenced region (bp) |
|---|---|---|---|
| 2TAIL01GN | 3.0 | 2TAIL01-04 | 1146 |
|  |  | 2TAIL01-09 | 1129 |
| 2TAIL12CA | 1.1 | 2TAIL12-06 | 967 |
|  |  | 2TAIL12-08 | 966 |
| 2TAIL16GN | 1.6 | 2TAIL16-03 | 1400 |

Example 2

Sequencing and Sequence Analysis

Merging sequences obtained from the first and second elongation steps of TAIL-PCR resulted in 1114 bp and approximately 1530 bp (because ca. 190 bp in the middle part was not yet precisely determined) upstream of the translational start codon for CA and GN, respectively. In further steps, first this unknown part (189 bp) was sequenced in the GN promoter region, and then CA was elongated to the same 5' end position as the GN sequence. These finishing steps provided a final sequence length of 1661 bp for CA and 1524 bp for GN, both counted from the PAL translational start site.

The main differences between the CA and GN sequences, apart from several single nucleotide polymorphisms (SNPs), were located in two defined regions. There were five deletions of 3 bp to 15 bp in CA beyond 1100 bp from the translational start site, and four deletions in GN up to about 800 bp, i.e. (i) the previously mentioned 6 bp deletion (see example 1), situated in a repeat region (266 bp upstream of the translational start codon), (ii) another 3 bp and a 7 bp deletion, and, more significantly, (iii) a 156 bp deletion 404 bp from the translational start site (FIG. 15). It seemed therefore rational to separate these two regions in order to study their (combined or individual) effect on gene expression. For this purpose, full-length and truncated versions were designed for both the CA and GN sequences, which were designated as: pCAL (long, 1661 bp) and pCAS (short, 1038 bp) for CA, and pGNL (long, 1524 bp) and pGNS (short, 867 bp) for GN.

In addition, no significant homology to known sequences was found in any database with the BLAST algorithms, which indicates that the cloned sequences are not likely to be transcribed or derived from a coding region, and that they might be novel sequences with regulatory function.

Additional indications for the possible promoter activity of the obtained fragments can be deduced from computer analysis of the DNA sequences. An anonymous query to the PLACE database that contains most currently known plant promoters was performed and the most important functional elements are shown in FIG. 15. When all the four (full and truncated) promoter sequences were aligned and compared several interesting features could be observed.

A putative TATA box was identified 97-104 bp upstream of the translation start site (position 1556 and 1415 in pCAL and pGNL, respectively) indicating the presence of a short untranslated leader region. A few possible promoter elements including two typical PAL boxes could be located in the 600-700 bp region upstream of the putative TATA box. The most striking feature, however, was the 156 bp deletion in the promoter region of GN, which may be responsible for a differential expression pattern upon infection. Interestingly, several potential promoter elements were located in this additional region of CA (FIG. 15).

Example 3

Vector Construction and Generation of Transgenic Plants

In order to obtain experimental evidence for promoter activity of the cloned banana sequences, in total seven different promoters were inserted into the binary vector pCAMBIA1391z and pFAJ3160 to generate a common backbone for seven and five constructs, respectively, for *Agrobacterium*-mediated plant transformation (Table 13). The four banana promoters cloned into expression vectors were: a full (pCAL: 1649 bp, pLS15 and pLS37) and a truncated (pCAS:

1026 bp, pLS13 and pLS35) version from CA, as well as a full (pGNL: 1512 bp, pLS14 and pLS36) and a truncated (pGNS: 855 bp, pLS16 and pLS38) promoter from GN. This setup also represents an initial step towards functional analysis because the absence or presence of essential DNA regions can be identified by comparison of the full and truncated versions. In addition, three control promoters were employed: the 35S RNA promoter (872 bp, p35S) from Cauliflower Mosaic Virus, which is a classical constitutive control, mainly for dicotyledonous plants; the promoter and first intron of the maize ubiquitin) gene (ca. 2000 bp, pUBI), which is a similarly widespread constitutive control for monocotyledonous plants; and a plant defensin promoter (1234 bp, pPDF) from *Arabidopsis*, which is a standard pathogen-inducible promoter in dicotyledonous plants.

Each of the seven promoters was fused to the bacterial uidA$^{INT}$ reporter gene, which codes for a β-glucuronidase (GUS) enzyme and contains a 190 bp intron from the castor bean catalase gene (Ohta et al., 1990) to inhibit reporter gene expression in agrobacteria. Thus, positive reporter gene activity in plant cells indicates that the integrated promoter is indeed transcriptionally active in transgenic plants. The cloning has been done in pCAMBIA1391z; the banana promoters were generated by PCR from genomic DNA with sequence-specific primers. Two steps were performed: first, transformation of recombinant clones in *E. coli* for confirmation by DNA sequencing, and the correct constructs were then transferred to *Agrobacterium* by electroporation.

In addition, another five uidA$^{INT}$ constructs (pLS35-39, Table 13) were prepared in pFAJ3160, which contained a bar selectable marker gene for resistance to glufosinate herbicides instead of the hpt selectable marker gene. The reason for making this additional set of vectors was that while working well in banana and rice, hygromycin selection did not prove efficient in *Arabidopsis*. The average transformation frequency with six hpt constructs (pLS13-16, pLS23 and pLS26) was 0.03% out of ca. 240,000 seeds, whereas with the new bar vectors an average of 2.4% (140,000 seeds) was reached.

Finally, for transient gene expression assays via particle bombardment pLS7-8 (pCAS and pGNL) and pLS11-12 (pCAL and pGNS) were prepared in pCAMBIA1291z vector containing the same uidA reporter gene.

This makes a total number of 16 GUS constructs (plus pFAJ3160 control ready for use) prepared in this study for plant transformation.

In total, 249 independent transgenic banana lines were generated from GN embryogenic cell suspensions distributed among the following constructs: pLS13 (pCAS)—24 lines, pLS14 (pGNL)—21 lines, pLS15 (pCAL)—26 lines, pLS16 (pGNS)—35 lines, pLS23 (p35S)—49 lines, pLS25 (pUBI)—45 lines, and pLS26 (pPDF)—49 lines. All these lines were then multiplied to about 8-10 plants/line for field testing.

Rice transformation experiments were performed as well. The pLS15 (pCAL) construct was first successfully introduced in the *japonica* cultivar 'Nipponbare' and six independent plants were regenerated. All these plants were analyzed for promoter activity by histochemical GUS staining. Additionally, more plants were generated with other constructs and seed progenies were collected in the greenhouse: pLS13 (pCAS)—8 lines, pLS14 (pGNL)—5 lines, pLS15 (pCAL)—4 lines, pLS16 (pGNS)—16 lines, pLS23 (p35S)—9 lines.

In total, 3405 transgenic *Arabidopsis* plants were selected from 140,000 seeds obtained by in planta transformations with constructs pLS36, pLS38-39 in two genotypes (Col0 and sgs2) and pFAJ3160 as control (Table 13) in sgs2 only. Out of these, in total 252 lines (36 lines for each construct and each genotype) were selected for histochemical analysis.

Example 4

Analysis of Transgenic Plants in vitro and in Greenhouse 4.1. Transient Expression The first experimental evidence for promoter activity of the cloned banana sequences came from transient expression analysis of the introduced uidA gene in banana and tobacco.

Banana

GN embryogenic suspension cells were bombarded with microparticles coated with DNA of the different expression vector constructs. One day later, histochemical GUS assay revealed expression by all banana PAL promoters (FIG. 5C-F) similarly to the positive control UBI (FIG. 5A), visible as blue spots in the cells, while untransformed cells showed no background activity (FIG. 5B). Based on the density of the blue foci there seemed to be no major difference between the different constructs, and thus the strength of the corresponding promoters. The results also indicate that the promoters from the wild diploid CA are active in the cultivated triploid GN.

TABLE 13

List of banana promoter constructs for use in *Agrobacterium*-mediated plant transformation

| Reporter Gene | Promoters | | | | | | |
|---|---|---|---|---|---|---|---|
| | "Calcutta 4" | | "Grande Naine" | | Controls | | |
| (protein) | Short | Long | Short | Long | 35S | UBI | PDF |
| uidA (GUS) bombardment | pLS07 | pLS11 | pLS12 | pLS08 | | | |
| uidA$^{INT}$ (GUS) | | | | | | | |
| For banana, rice (hpf) | pLS13* | pLS15* | pLS16* | pLS14* | pLS23* | pLS25* | pLS26* |
| for *Arabidopsis* (bar) | pLS35 | pLS37 | pLS38 | pLS36 | pFAJ3160 | — | pLS39 |
| Promoter lenth (bp) | 1026 | 1648 | 854 | 1507 | 872 | ±2000 | 1234 |
| Abbreviation | pCAS | pCAL | pGNS | pGNL | p35S | pUBI | pPDF |

*vectors used for transgenic field testing.

Tobacco

Histochemical GUS staining was done on transiently transformed tobacco (*Nicotiana benthamiana*) leaves 2 days after infiltration with *Agrobacterium* harboring the expression vectors pLS13-16, pLS23 and pLS26 (staining data not shown). Similarly to transient expression in banana, all four banana PAL promoters were active in tobacco leaves, visible as a blue coloration of the leaves, together with the two controls known to be active in dicots and with no GUS background in untransformed control leaves. Again, there appeared no major difference in strength between the banana PAL promoters, except that CAS seemed a bit stronger. The PDF promoter was somewhat weaker, as expected, because this is an inducible one (Penninckx et al., 1996). In addition, the results indicate that the banana promoters are active beyond the species and genus border, in a dicotyledonous species, too.

4.2. PCR Analysis in Banana

In order to verify the presence of the hpt selectable marker gene in putative transgenic plants, PCR analysis was performed with gene-specific primers that amplify a 668-bp product. In total, 233 events were analyzed out of the 249 independent events regenerated, and overall 146 (63%) of them was PCR positive (Table 14).

TABLE 14

Summary of PCR screening for presence of the hpt selectable marker gene in transgenic banana plants

| Promoter | No. of events | PCR + | % |
|---|---|---|---|
| CAS | 24 | 9 | 38 |
| CAL | 25 | 21 | 84 |
| GNS | 32 | 23 | 72 |
| GNL | 21 | 16 | 76 |
| 35S | 47 | 30 | 64 |
| UBI | 43 | 24 | 56 |
| PDF | 41 | 23 | 56 |
| Total | 233 | 146 | 63 |
| Negative | 25 | 0 | 0 |

4.3. GUS Expression Analysis in Transgenic Plants (in vitro and Greenhouse)

Banana in vitro Plants

GUS expression analysis of banana in vitro plants (GN) was performed by histochemical GUS staining of leaves and roots (staining data not shown) and a fluorometric assay to quantitate GUS enzymatic activity in leaves. Both tests demonstrated that the four banana PAL promoters are active in stably transformed leaves and roots under in vitro conditions, similarly to the two positive controls. In accordance with transient expression in banana cells, CA promoters were active in the GN cultivar. Confirming transient expression results in tobacco, the CAS promoter again appeared strong. In addition, the PDF promoter did not show any expression in leaves nor in roots, similarly to the untransformed control, which indicates that this (inducible) *Arabidopsis* promoter may not be active in monocots, at least not in terms of baseline expression.

Quantitative analysis and statistical analysis of GUS expression in transgenic banana in vitro leaves (FIG. 6, Table 15) confirmed the histochemical GUS assay: the four banana PAL promoters were similarly active (p>0.05), with CAS having a high average activity. In addition, the constitutive control promoters 35S and UBI were significantly (p≤0.05) stronger than the banana PAL promoters but were not different from each other.

TABLE 15

Summary of GUS expression analysis in transgenic banana in vitro plants and GUS enzymatic activity in leaf of in vitro banana plantlets expressing PAL promoters and control promoter constructs.
Specific GUS enzymatic activity expressed in pmoles MU/h/µg total protein. Means separated by different letters are significantly (p ≤ 0.001) different from each other (Duncan's multiple range test).
n = number of replicates (samples) tested

| Promoter | No. of events | Histochemical GUS + | % | Fluorometric GUS in leaves + | % | Mean Spec. Activity (n) |
|---|---|---|---|---|---|---|
| CAS | 24 | 9 | 38 | 8/23 | 35 | 2609 a (7) |
| CAL | 25 | 18 | 72 | 18 | 72 | 1409 a (17) |
| GNS | 32 | 23 | 72 | 21/31 | 68 | 2770 a (20) |
| GNL | 21 | 16 | 76 | 16 | 76 | 1733 a (16) |
| 35S | 47 | 27 | 57 | 17 | 36 | 5294 b (21) |
| UBI | 43 | 21 | 49 | 21 | 49 | 5677 b (20) |
| PDF | 41 | 0 | 0 | 0 | 0 | NT |
| Total/average | 233 | 114 | 59 | 101 | 53 | NA |
| Negative | 25 | 0 | 0 | 0 | 0 | 0 | p = 0.000000
NT not tested; NA not applicable.

In order to provide some insight into how solid are these data and conclusions, observations were compared between the histochemical and fluorometric analyses (Table 15). Except for the 35S group, the two sets of data showed almost perfect equivalence. In addition, they correlated very well with the frequency and identity of positive events as revealed by PCR (Table 14). These observations prove that the cloned banana PAL sequences indeed possess promoter activities, which are stable and reproducible in banana, including that CA promoters are active in GN plants as well. Finally, stable expression in leaves and roots (and transiently in embryogenic cells) indicates that the banana PAL promoters are probably active in a wide range of organs and tissues.

Banana Greenhouse Plants

Due to the size of banana plants, only a limited number was transferred to the greenhouse for a first expression analysis under in vivo conditions. Three transgenic GN plants were grown for each banana PAL promoters as well as two untransformed control plants.

Each plant was histochemically analysed for GUS expression in different tissues of the leaf: petiole, leaf blade and vascular bundles in order to assess tissue-specificity of the PAL promoters' activity in leaves (staining data not shown). All promoters were positive in all tissues tested (petiole, leaf and vascular tissue), whereas none of the untransformed control tissues showed background GUS activity. In leaf blades only the wounded edges were stained due to restricted penetration of the X-Gluc substrate across the waxy epidermis. Petioles are characterized with a loose tissue structure, therefore the substrate was taken up more efficiently and staining was intense. In vascular sections staining was more pronounced in and around the midvein. These observations indicate that all banana PAL promoters are active in several banana leaf tissues under in vivo growing conditions.

Rice in vitro Plants

All six in vitro plants generated after transformation with pLS15 (pCAL) were analyzed for promoter activity by histochemical GUS staining of roots and leaves. According to the results (staining data not shown), the CAL promoter was active in roots and leaves in three (50%) of these plants whereas two untransformed control plants showed no background GUS activity in these tissues. Seeds were harvested from the plants for further analysis of the progeny. However, two of the three GUS expressing plants set only empty husks and the remaining one GUS positive plant yielded more than 100 seeds. These observations confirm transient expression analysis in tobacco that banana PAL promoters are active beyond the species border, in other monocot species, and this in a stable manner. Also, the results are in accordance with in vitro expression in banana, where the PAL promoters directed GUS expression in roots as well as leaves of transgenic plants.

Arabidopsis Greenhouse Plants

In total, 252 independent transgenic lines (36 lines for constructs pLS36, pLS38-39 in two genotypes, Col0 and sgs2, and for pFAJ3160 in sgs2 only) were selected for histochemical GUS analysis. As negative control, six untransformed lines were taken in Col0. Isolated leaves were analyzed for all transgenic and control lines simultaneously (staining data not shown). Expression in flowers, peduncles and seed husks was studied in lines transformed with pLS38 (GNS) and pLS36 (GNL) together with untransformed controls.

All 252 transgenic lines were positive and all six control lines were negative for GUS expression in leaves, which suggests a very reliable expression pattern of the banana promoters in Arabidopsis. A closer qualitative examination, however, revealed characteristic promoter-specific differences independently of the genotype: the two banana (GN) PAL promoters were active mainly in the vascular tissues, whereas the Arabidopsis PDF promoter exerted more uniform expression in the leaf, confirming the previous report of Manners et al. (1998). Interestingly, the 35S promoter directed in leaves a patchy expression that appeared to be random while untransformed controls remained negative.

In terms of specificity in generative organs, the banana PAL promoters were active in the flower, the peduncle and the seed husk of Arabidopsis with no background activity in negative (untransformed) controls. The lack of background GUS activity can be attributed to the high pH of the staining solution (see Materials and Methods), which suppresses endogenous GUS-like enzymes reported for Arabidopsis (Sudan et al., 2006).

These results indicate that—besides tobacco—the banana PAL promoters are also active in another dicot species. In addition, this is the first indication that the banana promoters direct transgene expression not only in vegetative tissues but in generative organs as well.

Example 5

Transgenic Field Test of Banana

Before practical agricultural applications, in the first place for banana, a detailed characterization in the field under real, tropical conditions is an indispensable requirement. Therefore, we carried out a systematic field evaluation of expression patterns in transgenic (banana) plants by the promoters of the invention fused to the uidA$^{INT}$ reporter gene.

In total, 146 independent banana events, including 126 transgenic events (66 banana PAL promoter events and 60 control promoter events) and 20 untransformed controls (Table 16) were planted to the field in Costa Rica. Of each event, at least six plants were planted in miniblocks of three plants distributed in two main blocks that were treated (block B) and not treated with fungicides (block C). In addition, a control experiment was designed for 54 (>81%) of the 66 transgenic banana PAL promoter events in a screenhouse to test whether fungicide treatment alone had an effect on promoter activity.

TABLE 16

List of transgenic banana events selected for field testing

| Agrobacterium construct | # events |
|---|---|
| Experimental treatments: | |
| pLS13 (CAS-GUS) | 9 |
| pLS15 (CAL-GUS) | 19 |
| pLS16 (GNS-GUS) | 22 |
| pLS14 (GNL-GUS) | 16 |
| Subtotal | 65 |
| Control treatments: | |
| pLS23 (35S-GUS) | 20 |
| pLS25 (UBI-GUS) | 20 |
| pLS26 (PDF-GUS) | 20 |
| Negative control: untransformed | 20 |
| Subtotal | 80 |
| TOTAL | 146 |

For a comprehensive analysis five experiments were designed in order to study:
- tissue-specific expression and promoter strength (experiment T),
- effects of fungicide spraying under control conditions (no infection) in screenhouse (exp. C),
- inducibility by fungus infection, comparison of plants of the same events between the two main blocks (exp. F and X),
- developmental expression in different leaves of the same events (exp. D), and
- intra-event variation, i.e. the same leaves from different plants of the same events (exp. I).

5.1. Tissue-Specificity Study (Exp. T)

Field plants in the generative phase were sampled in the sprayed block B (so that to have a higher chance for more developed bunches). Five samples, the youngest full leaf, roots, bunch peduncle, pulp and peel of the fruits were taken (separately) from one plant per event. Multiplication by four events per treatment and by eight treatments (eight constructs) brought this to a total of 160 samples in experiment T, which were subjected to histochemical GUS staining (staining data not shown). All banana PAL promoters as well as the 35S and the UBI control promoters were active in all tissues of transgenic banana plants in the field, as evidenced by their blue coloration, whereas the untransformed control remained negative.

Some systematic differences appeared visually between the promoters when compared for each tissue individually: the constitutive promoters (35S and UBI) gave more intense staining in the root and the peduncle than the banana PAL promoters did. All six promoters were active in all tissues but expression in the peduncle was reproducibly higher for all promoters than in the other tissues. These data confirmed previous results in Arabidopsis (example 4) that the banana PAL promoters are active in tissues formed during generative development. The negative (untransformed) control collected from the same field did not show background GUS activity in any of the tissues tested, which indicates that the observed GUS expression patterns were not caused by endogenous plant GUS-like activity or by endophytic organisms possessing a functional GUS gene but they reflect the genuine effect of the integrated promoters. Quantitative GUS enzymatic analysis was also performed and statistically analyzed. There was no significant interaction between the two dependent variables (tissue and promoter) tested, therefore one-way ANOVA was performed for each variable separately.

Tissue: in transgenic plants expressing GUS by the banana PAL promoters (FIG. 7; Table 17A), expression in the peduncle was significantly higher (p≤0.001) than in the other tested tissues. In the fruit, GUS expression was significantly lower in the pulp than in the peel. In transgenic plants expressing GUS by the constitutive control promoters 35S and UBI (FIG. 8, Table 17B), the expression in leaves was significantly lower (p≤0.001) and in the peduncle was again significantly higher than in the other tested tissues.

TABLE 17A

GUS enzymatic activity in leaf, root, peduncle, pulp and peel of independent transgenic banana plants expressing banana PAL promoter constructs in the field. Specific GUS enzymatic activity expressed in pmoles MU/h/μg total protein. Means represented by different letters are significantly (p ≤ 0.001) different from each other (Duncan's multiple range test on log10 transformed data).
n = number of replicates (samples) tested.

| Tissue | Mean | n |
|---|---|---|
| Pulp | 1839.5a | 8 |
| Root | 2147.5ab | 8 |
| Leaf | 2641.6ab | 8 |
| Peel | 3729.4ab | 8 |
| Peduncle | 7288.3c | 8 | p = 0.000122 (ANOVA)

TABLE 17B

GUS enzymatic activity in leaf, root, peduncle, pulp and peel of independent transgenic banana field expressing constitutive promoter constructs in the field. Specific GUS enzymatic activity expressed in pmoles MU/h/μg total protein. Means separated by different letters are significantly (p ≤ 0.001) different from each other (Duncan's multiple range test). n = number of replicates (samples) tested.

| Tissue | Mean | n |
|---|---|---|
| leaf | 3756.4a | 4 |
| peel | 7517.4b | 4 |
| root | 9322.2b | 4 |
| pulp | 9544.5b | 4 |
| peduncle | 13374.1c | 4 | p = 0.000113

Construct: The difference in expression level between the banana promoters and the control promoters was evaluated (FIGS. 7 & 8 & Table 18. The expression level of the GUS gene is not significantly different when driven by the control promoters compared to the banana PAL promoters in leaf. However, expression levels of the GUS gene in the peduncle, the root, pulp and peel of the fruit was significantly higher when the GUS gene was driven by the control promoters.

TABLE 18

Statistical analysis (univariate tests) of quantitative GUS measurements of field plants of experiment T.
Grouping variant: banana promoter vs control promoter.

| | P value | Significantly different? |
|---|---|---|
| Leaf | 0.2152 | NO |
| Peduncle | 0.0095 | YES |
| Pulp | <0.0001 | YES |
| Peal | 0.0083 | YES |
| root | <0.0001 | YES |

Quantitative GUS enzymatic analysis confirmed histochemical GUS staining in that the peduncle is the most expressive tissue and that there are no major strength differences among the banana PAL promoters. As a similarly good accordance between quantitative and histochemical GUS assay was also found in transgenic banana in vitro plants this correlation can be regarded as sound.

5.1. Screenhouse Control (Exp. C)

The field experiment was divided into a sprayed block (to protect plants and minimize possible induction by infection) and an unsprayed block (to ensure induction by natural infection). However, fungicides themselves might also influence promoter expression patterns and thus interfere with conclusions on fungus inducibility. Therefore, we needed to test the effect of fungicide sprays under no infection but otherwise very similar conditions to the field. For this purpose, vegetative progeny plants (suckers') from transgenic field lines were grown up in a screenhouse outside the banana cultivation area to minimize possible infections. In addition, shoots were completely cut back so that to remove leaves possibly exposed to spores.

Where possible, two suckers were taken from transgenic banana PAL promoter event sampled for Experiment F (see 5.3) (Block B and C) and from 12 untransformed control plants. One of the duplicates was treated on a regular basis with the same fungicides as in the field and the other plant was not sprayed to serve as control. Plants were grown for 3 months before taking leaf samples. Experiment C consisted of 254 samples.

Quantitative GUS enzymatic analysis was performed and statistically analyzed. Only paired data (events samples in both blocks) were considered. There was no significant interaction between the two dependent variables (promoters and spray) tested, therefore one-way ANOVA was performed for each variable separately.

Construct: There was no significant difference (p>0.05) in expression of the GUS gene between the different PAL promoters and the control promoters in leaves of the screenhouse plants of the control element. The same result was seen when the analyses was done on data from sprayed plants.

PAL promoters: there were no significant differences (p>0.05) among the promoters for GUS expression in leaves of the screenhouse plants (FIG. 9). The level of expression for all banana promoters was similar to that observed in vitro and ca. 2 times lower than in the field, which suggests that transfer to soil alone is not sufficient to explain the difference and developmentally related factors may also be involved.

Spray: spraying the plants with fungicides had no significant effect (p>0.05) on the expression level of the GUS gene when controlled by the PAL promoters in leaves of screenhouse plants (FIG. 10). Similar results were obtained when the data were further divided per individual construct (results not shown).

This control experiment showed that fungicide spraying alone exhibited no detectable effect on the expression pattern of banana PAL promoters, thus comparison of the sprayed and not sprayed blocks in the field was suitable to assess fungus inducibility.

5.3. Fungus Inducibility (Exp. F)

In order to test the influence of fungus infection on the activity of the promoters, a first experiment was performed with samples collected from symptomatic leaves of field plants before they reached the generative phase. Where possible, leaf samples were taken from two plants per event (one from sprayed block B, i.e. not infected, and one from not sprayed block C, i.e. *Mycosphaerella* infected plants) from all 145 events. In total 290 samples are taken for this experiment. Quantitative GUS enzymatic analysis was performed and statistically analyzed. Only paired data (events samples in both blocks) were considered. There was no significant interaction between the two dependent variables (infection and construct) tested, therefore one-way ANOVA was performed for each variable separately.

Infection: although the expression of the GUS gene was consistently higher in leaves of naturally infected (not sprayed) plants compared to the sprayed ones, statistical analysis of the data (FIG. 11) did not reveal a significant difference (p>0.05) for all the constructs overall (univariate tests of significance–effect=infection: p=0.074). This could be caused by high variance in the data. Similar results were obtained when the data were further divided per individual construct or per groups (banana and control) constructs (results not shown). A second experiment (exp. X) was therefore designed to decrease data variation (see below).

Promoter: in transgenic plants expressing GUS by the different PAL and control promoters (FIG. 12), there was no significant difference (p>0.05) in sprayed leaves of field plants. Similar results were obtained when the data were analysed for naturally infected (not sprayed) plants (results not shown). When statistical analysis was performed for sprayed and not sprayed plants combined, some differences were observed (result not shown); therefore more sample collection was designed (see below, exp. X).

5.4. Fungus Inducibility (exp. X)

It turned out from the first fungus induction experiment (exp. F) that it is important to minimize the variance of the data. Therefore, in a second experiment (exp. X) only 3 events were selected per construct, events that exhibited comparable expression levels, and increased numbers of independent samples were collected per event.

Per event 24 samples were taken, from 4 plants (2 plants infected and 2 plants not infected). Per plant, Leaf 1, 2 and 3 from the mother and the sucker were sampled. This makes 12 samples per condition (infected, not infected). Likewise, twenty-four leaf samples were taken from two events for the pos control (Ubi) (none for pos control 35S), and one for the negative control, which brings the total sample number (24× 16) to 384. The 24 samples were taken as follows: 12-12 samples each from sprayed and non-sprayed plants (two blocks). Out of these 12 samples, six were collected from one plant number and six from a second plant number from the same event. The mother and the first sucker from both event numbers were sampled (leaf 1,2,3). With this sampling strategy additional conclusions can be drawn about any variation in expression within plants and between mother plants and the suckers. All sampling was done on symptomatic plants, while plants with a bunch were not sampled and in this case the next strongest plant was considered as mother plant.

Infection: After statistical analysis of the data (not shown), it can be concluded that there is no significant difference (p>0.05) in expression level of the GUS gene driven by the banana PAL promoters, between infected plants and not infected plants. Likewise, the expression level of the GUS gene driven by the Ubiquitin promoter was not significantly different (p>0.05) between infected plants and not infected plants.

Mother & sucker: After statistical analysis of the data (not shown), it can be concluded that there is no significant difference (p>0.05) in expression level of the GUS gene driven by the banana PAL promoters or by the UBI promoter, between the mother and sucker plants.

Differences between leaf 1, 2 and 3: After statistical analysis of the data it can be concluded that the expression level of the GUS gene driven by the banana PAL promoter is significantly higher in leaf 1 than in leaf 2 (p<0.05) (Table 19). There was no significant difference (p>>0.05) in expression level of the GUS gene driven by the ubiquitin promoter, between leaf 1, 2 and 3.

TABLE 19

GUS enzymatic activity in leaf 1, 2 and 3 of independent transgenic banana field expressing PAL promoter constructs in the field. Specific GUS enzymatic activity expressed in pmoles MU/h/µg total protein. Means separated by different letters are significantly (p ≤ 0.001) different from each other (Duncan's multiple range test).
n = number of replicates (samples) tested.

| Leaf | Mean | n |
|---|---|---|
| 3 | 1074.4a | 97 |
| 2 | 1171.6a | 101 |
| 1 | 1454.3b | 100 | p < 0.00001

5.5. Developmental Study (Exp. D)

To characterize stability of promoter expression during (vegetative) development, consecutive leaves with different age on the same plant were analysed. Five samples, the cigar and leaf numbers 1-3-5-8 were collected from two plants per event: one plant from sprayed block B and another one from naturally infected block C. Multiplication by four events per construct and by eight constructs brought this to a total of 320 (2×160) samples in experiment D, which were subjected to quantitative GUS enzymatic analysis.

According to statistical analysis, there was no significant interaction between the three dependent variables (leaf number block and construct) tested, therefore one-way ANOVA was performed for the variables separately.

Leaf number: in transgenic plants expressing GUS by the banana PAL promoters (FIG. 13) and the control promoters (FIG. 14), there was no significant difference (p>0.05) between the different leaves of field plants, though in leaf3 (PAL, 35S and UBI) and leaf5 (PAL) expression was somewhat lower. We can see a trend that expression in the cigar and the first leaf is somewhat higher (in line with the results in experiment X), but this is in this experimental setop not statistically significant. Similar results were obtained when the data were further divided per block or per individual construct (results not shown). All promoters taken together, the results indicate that the banana PAL promoters (similarly to the constitutive ones) exhibit a stable expression throughout vegetative development of banana plants in the field. This means that in case of a transgenic fungal control strategy, for example, one could expect very uniform expression of the antifungal gene and thus equal protection across all leaves in a plant.

Infection: in transgenic plants expressing GUS by the banana PAL promoters combined for all leaves together (not shown), there was no significant difference (p>0.05) between the two (sprayed and non-sprayed) blocks. Similar results were obtained when the data were further divided per individual construct (results not shown). This result again implies that natural infection in the field has no significant influence on the activity of the banana PAL promoters.

5.5. Intra-Event Variation (Exp. I)—Stability and Reproducibility

For multipication and distribution of promising commercial (transgenic) lines, it is crucial to know how uniform is the inter-plant or intra-event variation.

Leaf samples (leaf 1) are taken in Block A and Block C, both blocks are not sprayed with fungicides. Samples are collected from 4 plants per event and 4 events per construct (8 constructs). Experiment I consisted of 128 samples. 4 plants of 1 event and 4 events per construct were measured. To be able to analyze the data statistically, the 4 measurements of 1 event are ranked from low to high, being 1 the lowest and 4 the highest. This is done for all the events. Means are calculated per ranking.

After statistical analysis of the data (Table 20), it can be concluded that there is a significant difference (p<0.05) in expression level of the GUS gene driven by the PAL promoters, between the different plants of 1 event. Results from rank 1 and 2 are significantly lower than those of rank 3 and 4. When analysis is done per construct there are no significant differences (not shown). Similar findings were obtained for the GUS gene expression driven by the control promoters (results not shown). Results of rank 1 (1126.9 pmoles MU/h/µg total protein) are significantly lower than those of rank 2 (1732.7 pmoles MU/h/µg total protein), 3 (2276.2 pmoles MU/h/µg total protein) and 4 (2505.4 pmoles MU/h/µg total protein) and the results of rank 2 are significantly lower than those of rank 3 and 4. However, variances were too big, making it difficult to draw good conclusions.

TABLE 19

GUS enzymatic activity between the different plants of 1 event of independent transgenic banana field expressing PAL promoter constructs in the field. Specific GUS enzymatic activity expressed in pmoles MU/h/µg total protein. Means separated by different letters are significantly (p ≤ 0.001) different from each other (Duncan's multiple range test). n = number of replicates (samples) tested.

| Ranking | Mean | n |
|---|---|---|
| 1 | 1152.7a | 14 |
| 2 | 1407.9a | 16 |
| 3 | 1928.9b | 16 |
| 4 | 2318.2b | 15 | p < 0.00012

CONCLUSION

Two banana promoters were cloned and sequenced: one from the fungal disease resistant wild diploid 'Calcutta 4' (CA) and another from the susceptible commercial dessert triploid cultivar 'Grande Naine'. Next, transgenic banana and heterologous plants were generated using vectors comprising the banana promoters (full-length or truncated) and compared to transgenic plants transformed with vectors comprising different constitutive or inducible control promoters.

Demonstration and detailed monitoring of PAL promoter expression patterns under in vitro (or greenhouse) and real field (and screenhouse) conditions, respectively, confirmed that:

a. the promoters are active in other banana landraces, i.e. from wild diploid 'Calcutta 4' in commercial triploid 'Grande Naine',
b. the promoters are functional in a broad host range such as other monocotyledonous and dicotyledonous species,
c. the respective full-length and truncated promoter versions have slightly different strength but identical activity in terms of expression pattern (stability and tissue specificity),
d. the promoters' strength in vitro is significantly (ca. 50%) lower than the standard constitutive promoters (35S and UBI), whereas in the field they appear to be not different,
e. the promoters are not affected significantly by fungicides or fungus infection in the field,
f. the promoters are active in a wide range of vegetative or generative organs and specific banana tissues in the field,
g. the promoters are stably and uniformly expressed during development of banana plants in the field, and
h. the PAL promoters are stably expressed after micropropagation of transgenic banana lines.

On the basis of an original and comprehensive large-scale field study we can thus conclude that a set of very well characterized and stable banana PAL promoters are now available for routine and/or commercial transgenic applications in higher plants as well as for cisgenic or intragenic use in banana.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

Aljanabi S M, Martinez I (1997) Universal and rapid salt-extraction of high quality genomic DNA for PCR-based techniques. Nucleic Acids Res 25:4692-4693.

Altschul S F, Gish W, Miller W, Myers E W, Lipman D J (1990) Basic local alignment search tool. J Mol Biol 215: 403-410.

Altschul S F, Madden T L, Schäffer A A, Zhang J, Zhang Z, Miller W, Lipman D J (1997) Gapped BLAST and PSI-BLAST: a new generation of protein database search programs. Nucleic Acids Res 25:3389-3402.

Cervera M (2004) Histochemical and fluorometric assays for uidA (GUS) gene detection. In: Peña L (ed.) Transgenic Plants: Methods and Protocols (Methods in Molecular Biology, Vol. 286), Humana Press Inc., pp. 203-213.

Christensen A H, Quail P H (1996) Ubiquitin promoter-based vectors for high-level expression of selectable and/or screenable marker genes in monocotyledonous plants. Transgenic Res 5:213-218.

Clough S J, Bent A F (1998) Floral dip: a simplified method for *Agrobacterium*-mediated transformation of *Arabidopsis thaliana*. Plant J 16:735-743.

De Bolle M F C, Butaye K M J, Coucke W J W, Goderis I J W M, Wouters F J, van Boxel N, Broekaert W F, Cammue B P A (2003) Analysis of the influence of promoter elements and a matrix attachment region on the inter-individual variation of transgene expression in population of *Arabidopsis thaliana*. Plant Sci 165:169-179.

Dellaporta S, Wood J, Hicks J B (1983) A plant DNA mini-preparation: version II. Plant Mol Biol Rep 1:19-21.

Dhed'a D, Dumortier F, Panis B, Vuylsteke D, De Langhe E (1991) Plant regeneration in cell suspension cultures of the cooking banana cv. 'Bluggoe' (*Musa* spp. ABB group). Fruits 46:125-135.

Duncan D B (1955) Multiple range and multiple F tests. Biometrics 11:1-42.

Elmayan T, Balzergue S, Béon V, Daubremet J, Guénet Y, Mourrain P, Palauqui J-C, Vernhettes S, Vialle T, Wostrikoff K, Vaucheret H (1998) *Arabidopsis* mutants impaired in cosuppression. Plant Cell 10:1747-1757.

Levene H (1960) Robust tests for equality of variances. In: Olkin I, Hotelling H et al. Contributions to Probability and Statistics: Essays in Honor of Harold Hotelling. Stanford University Press, pp. 278-292.

Liu Y G, Huang N (1998) Efficient amplification of insert end sequences from bacterial artificial chromosome clones by thermal asymmetric interlaced PCR. Plant Mol Biol Rep 16:175-181.

Maas S (1999) Efficient and rapid procedure for blue-white screening of recombinant bacterial clones. BioTechniques 27:1126-1128.

Manners J M, Penninckx I A M A, Vermaere K, Kazan K, Brown R L, Morgan A, Maclean D J, Curtis M D, Cammue B P A, Broekaert W F (1998) The promoter of the plant defensin gene PDF1.2 from *Arabidopsis* is systemically activated by fungal pathogens and responds to methyl jasmonate but not to salicylic acid. Plant Mol Biol 38:1071-1080.

Mendel R R, Müller B, Schulze J, Kolesnikov V, Zelenin A (1989) Delivery of foreign genes to intact barley cells by high-velocity microprojectiles. Theor Appl Genet 78:31-34.

Menossi M, Cremonese N Jr, Maron L G, Arruda P (2000) Making colony PCR easier by adding gel-loading buffer to the amplification reaction. BioTechniques 28:424-426.

Mourrain P, Béclin C, Elmayan T, Feuerbach F, Godon C, Morel J B, Jouette D, Lacombe A M, Nikic S, Picault N, Rémoué K, Sanial M, Vo T A, Vaucheret H (2000) *Arabidopsis* SGS2 and SGS3 genes are required for posttranscriptional gene silencing and natural virus resistance. Cell 101:533-542.

Murashige T, Skoog F (1962) A revised medium for rapid growth and bioassays with tobacco tissue cultures. Physiol Plantarum 15:473-497.

Nemestothy G S, Guest D I (1990) Phytoalexin accumulation, phenylalanine ammonia lyase activity and ethylene biosynthesis in fosetyl-Al treated resistant and susceptible tobacco cultivars infected with *Phytophthora nicotianae* var. *nicotianae*. Physiol Mol Plant Pathol 37:207-219.

Ohta S, Mita S, Hattori T, Nakamura K (1990) Construction and expression in tobacco of a β-glucuronidase (GUS) reporter gene containing an intron in the coding sequence. Plant Cell Physiol 31:805-813.

Pang K M, Knecht D A (1997) Partial inverse PCR: a technique for cloning flanking sequences. BioTechniques 22:1046-1048.

Penninckx I A M A, Eggermont K, Terras F R G, Thomma B P H J, De Samblanx G W, Buchala A, Métraux J-P, Manners J M, Broekaert W F (1996) Pathogen-induced systemic activation of a plant defensin gene in *Arabidopsis* follows a salicylic acid-independent pathway. Plant Cell 8:2309-2323.

Pérez-Hernández J B (2000) Development and application of *Agrobacterium*-medated genetic transformation to indrease fungus-resistance in banana (*Musa* spp.). Diss. Doct. 442. Katholieke Universiteit Leuven, Faculteit Landbouwkundige en Toegepaste Biologische Wetenschappen. Departement Toegepaste Plantwetenschappen.

Pérez Hernández J B, Remy S, Swennen R, Sági L (2006) Banana (*Musa* sp.). In: Wang K (ed.) *Agrobacterium* Protocols Vol. 2 (Methods in Molecular Biology, Vol. 344), Humana Press Inc., pp. 167-175.

Postmaster A, Kuo J, Sivasithamparam K, Turner D W (1997) Interaction between *Colletotrichum musae* and antagonistic microorganisms on the surface of banana leaf discs. Sci Horticulturae 71:113-125.

Sági L, Panis B, Remy S, Schoofs H, De Smet K, Swennen R, Cammue B P A (1995) Genetic transformation of banana and plantain (*Musa* spp.) via particle bombardment. Nature Biotechnology 13:481-485.

Sallaud C, Meynard D, van Boxtel J, Gay C, Bes M, Brizard J P, Larmande P, Ortega D, Raynal M, Portefaix M, Ouwerkerk P B F, Rueb S, Delseny M, Guiderdoni E (2003) Highly efficient production and characterization of T-DNA plants for rice (*Oryza sativa* L.) functional genomics. Theor Appl Genet 106:1396-1408.

Schmidt D M, Ernst J D (1995) A fluorometric assay for the quantification of RNA in solution with nanogram sensitivity. Anal Biochem 232:144-146.

Schultz J, Milpetz F, Bork P, Ponting C P (1998) SMART, a simple modular architecture research tool: identification of signaling domains. Proc Natl Acad Sci USA 95:5857-5864.

Shapiro S S, Wilk M B (1965) An analysis of variance test for normality. Biometrika 52:591-599.

Sudan C, Prakash S, Bhomkar P, Jain S, Bhalla-Sarin N (2006) Ubiquitous presence of beta-glucuronidase (GUS) in plants and its regulation in some model plants. Planta 224:853-864.

Terauchi R, Kahl G (2000) Rapid isolation of promoter sequences by TAIL-PCR: the 5'-flanking regions of Pal and Pgi genes from yams (*Dioscorea* ). Mol Gen Genet 263: 554-560.

Wiame I, Remy S, Swennen R, Sági L (2000) Irreversible heat inactivation of DNase I without RNA degradation. BioTechniques 29:252-256.

---

What is claimed is:

1. A polynucleotide construct comprising a polynucleotide having plant promoter activity operably linked to a heterologous regulatory sequence and/or a heterologous coding sequence, wherein said polynucleotide having plant promoter activity comprises a polynucleotide having the nucleotide sequence of SEQ ID NO:1, SEQ ID NO:2, SEQ ID NO: 3 or SEQ ID NO:4.

2. The polynucleotide construct according to claim 1, wherein said heterologous coding sequence is a polynucleotide which encodes an RNA or a polypeptide.

3. A vector comprising the polynucleotide construct according to claim 1.

4. A transformed host cell comprising the polynucleotide construct according to claim 1, wherein said host cell is a plant cell.

5. The plant cell according to claim 4, wherein said plant cell is derived from a monocot or a dicot plant.

6. The plant cell according to claim 5, wherein said plant is a species belonging to Solanaceae, Brassicaceae, Musaceae, or Poaceae, or wherein said plant is soybean, sunflower, sugar beet, alfalfa, peanut, cotton, coffee, coconut, pineapple or citrus tree.

7. A transgenic plant or progeny thereof, plant part, plant tissue or reproductive material of a plant comprising the polynucleotide construct according to claim 1.

8. A transgenic plant or progeny thereof, plant part, plant tissue or reproductive material of a plant comprising the polynucleotide construct according to claim 1 stably incorporated in the plant genome.

9. A method for producing transformed plant cells, comprising: (a) introducing the polynucleotide construct according to claim 1 into regenerable plant cells so as to yield transformed plant cells; and (b) identifying or selecting transformed plant cells.

10. A method for producing a transgenic plant, comprising: (a) introducing the polynucleotide construct according to claim 1 into regenerable plant cells so as to yield regenerable transformed plant cells; (b) identifying or selecting a population of transformed plant cells; and (c) regenerating a differentiated transgenic plant from said population.

11. A method of expressing a product in a host cell, said method comprising introducing the polynucleotide construct according to claim 1 into a host cell.

12. A processed food or non-food product, comprising the polynucleotide construct according to claim 1.

\* \* \* \* \*

SEQUENCE LISTING

```
<160> NUMBER OF SEQ ID NOS: 40

<210> SEQ ID NO 1
<211> LENGTH: 1664
<212> TYPE: DNA
<213> ORGANISM: MUSA

<400> SEQUENCE: 1
gcttcctttg tttttgctag ttagatcctt atgccaaggc tcatgtgatt tggctgtcat      60
ggttggtggt gaagagcatt ccacaccaaa ctcccagtct cataaacaaa ggcttgcatt     120
caattttctc acccttgacc agaatttcca attttggttg gtggaaattt ccttcagaca     180
aaagaaaaac tattggccac aaggttaaat tgacagcaag tttggagcat gtctcatcaa     240
taaactgata ggtgtgtcca cttgactcaa atctttagtc ggtaaagatt ttgatagttt     300
atcgtaagac tctgaactca aatctgtctt tgtaaaaaaa ataatataaa tattcattga     360
aacaaaaaat caagtatcaa aagattaagt taacgtctct caaacataag aattgtatgc     420
```

```
cgaggttcca cttaagtcat gttaagtatc taataattga accaaggaag gaaggagtgt      480
tgtttgttgt catgatagag gtaaaaagag tttatgatgt cataatactt gtattaacaa      540
ccattcatcc atgcatacca tctgaattaa gtggtaatcc tgtacaagat tgttcaagtg      600
gaatttgact gtcaaaagag taagctgcat actaaggatc tgtcatctac aactaatctt      660
gtggaagatc tgaatcgaag aacctgagct tggaaacaac tcccaagata ttgtgtcttt      720
catttctcag aaagtctagg gacttaaaag tatgttcaac aagccatatt cctttaatct      780
tgctgaggaa ttggattaca tcttccttgc aattcctctc catttgcatg gcaattcggc      840
agctatttct tacttggttc tatgagggaa gggagaaggg aggttggtga ggacaattcc      900
catggcaatt tggcagctac ttccatacct acttcattag aggagagagg ttggtgggga      960
caatgacctg tgtggcaggc agtagtacaa caactcactt gcgtttcttc tcctatactt     1020
aaatgacgac aaaatcttcg attgggttca atttaattaa aattattatt ttatatgatt     1080
tacacaaact aaatagttca ttctaataga aaactgtggg atcagaagcc acacacaaaa     1140
aaaaaaagac aaaactatag aatcgaactt atctttaatt tatattttt atatctaaaa      1200 cattaatatg ataataatat acttactaga tacacatagt tgccatgatc aacattacta     1260
gaagaagatg aaaagaatga tgaatgctta tatgactcga gtatgacatg aacgtggaaa     1320
tcaccttcta ctcaggagaa gcaatcgtca tatccgcggg atcgtcctgg aaagagagag     1380
agagagagat agagagaaga cgaggggatg aggaaggaag aattggtgag gaaaacgatg     1440
gcatgcatgc ctcatatctc cacccacccc tctcctcccc tccatctttg acgagaccga     1500
tccagtggtt gaagtattat gcccacctaa ctctctccat gccaccacaa gctgctctat     1560
ttaacccttc cttgtgctcc tctctacctc agggttatct caccttcctt accttccacc     1620
tcctcccttc tggtctttcg tcggatctcg ttccgtgatc gatg                      1664

<210> SEQ ID NO 2
<211> LENGTH: 1527
<212> TYPE: DNA
<213> ORGANISM: MUSA

<400> SEQUENCE: 2
gcttcctttg tttttgctag ttagatcctt atgccaaagg ctcatgtgat ttggctgtca       60
tgtttggtgg tgaagagcat tccacaccaa actcccagtc tcataaacag aggctttcat      120
tcaattttct caccccttga cagaatttcc aagcttggtt ggtggaaatt tccttcagac      180
aaaagaaaaa ctattggcca caaggttaaa ttgacagcaa gttcggagca tgtctcatca      240
ataaactgat aggtgtgtcc agttgactca aatctttagt cgataaagat tttgatagtt      300
tatcgtaaga ctctgaactc aaatctcgtc tttgtaaaaa aaaaaaaat actataaata      360 ttcattgaaa caaaaaatca agtatcaaaa gattaacaat ttgatgacga aattaacgtt      420
tctcaaacat aagaattgta tgccgaggga ggttccactt aagtcatgtt aagtatctaa      480
taattgaacc aaggaaggaa ggaaggagtg ctgtttgttg tcatgataga ggtcaaaaga      540
gtttatgatg tcataatact tgtattaaca accattcatc catacatacc atctgaatta      600
agtggtaatc ctgtacaaga ttgttcaagt ggaatttgac tgtcaaaaga gtaagctgct      660
gcatactaag gatctgtcat ctacaactaa tcttgtggaa gatctgaatc gaagaccttg      720
agctcggaaa caacttccaa gatattgtgt ctttcatttc tcagaaagta tagggactta      780 aaagtatgc tcaacaagcc atattccttt aatcttgttg aggaattgga ttacatcttc      840
cttgcaattc ctctccattt gcatggcaat tcggcagcta tttcttactt ggttctatga      900
```

-continued

```
gggaagggag gttggtgagg acaattccca tggaaatttg gcagctactt ccatacctac      960
ttcattagag gagagaggtt ggtggggata atgacctgtg tggcaggcag tacaacaact     1020
cacttgcgtt tcttctccta tacttaaatg acgacaaaat ctttgattgg gttcaattta     1080
attaaaatta ttgttttata tgatttacac aaactaaata acattactag aagaagatga     1140
aaagaaagat gaatgcttat atgactcgag tgtgacatga acgtggaaat caccttctac     1200
tcgggagaag caatcgtcat atccgcggga tcgtcctgga agagagagag agagagaga     1260 ggacgagggg atgaggaagg aagaattggt gaggaaaacg atggcatgca tgcctcttat     1320
ctccacccac ccctcctctc ccctccatct ttgacgagac cgatccagtg gttgaagtat     1380
tatgcccacc taactctctc catgccacca caagctgctc tatttaaccc ttccttgtgc     1440
tcctctctac ctcagggtta tctcaccttc cttaccttcc acttcctccc ttctggtctt     1500
tcgtcggatc tcgttccgtg atcgatg                                         1527

<210> SEQ ID NO 3
<211> LENGTH: 1041
<212> TYPE: DNA
<213> ORGANISM: MUSA

<400> SEQUENCE: 3
gctgcatact aaggatctgt catctacaac taatcttgtg gaagatctga atcgaagaac       60
ctgagcttgg aaacaactcc caagatattg tgtctttcat ttctcagaaa gtctagggac      120
ttaaaagtat gttcaacaag ccatattcct ttaatcttgc tgaggaattg gattacatct      180
tccttgcaat tcctctccat ttgcatggca attcggcagc tatttcttac ttggttctat      240
gagggaaggg agaagggagg ttggtgagga caattcccat ggcaatttgg cagctacttc      300
catacctact tcattagagg agagaggttg gtggggacaa tgacctgtgt ggcaggcagt      360
agtacaacaa ctcacttgcg tttcttctcc tatacttaaa tgacgacaaa atcttcgatt      420
gggttcaatt taattaaaat tattatttta tatgatttac acaaactaaa tagttcattc      480
taatagaaaa ctgtgggatc agaagccaca cacaaaaaaa aaaagacaaa actatagaat      540
cgaacttatc tttaatttat atttttata tctaaaacat taatatgata ataatatact      600
tactagatac acatagttgc catgatcaac attactagaa gaagatgaaa agaatgatga      660
atgcttatat gactcgagta tgacatgaac gtggaaatca ccttctactc aggaagcaa     720 atcgtcatat ccgcgggatc gtcctggaaa gagagagaga gagataga gagaagacga      780 ggggatgagg aaggaagaat tggtgaggaa aacgatggca tgcatgcctc tatctccac     840 ccaccctct cctcccctcc atctttgacg agaccgatcc agtggttgaa gtattatgcc      900
cacctaactc tctccatgcc accacaagct gctctattta acccttcctt gtgctcctct      960
ctacctcagg gttatctcac cttccttacc ttccacctcc cccttctgg tctttcgtcg      1020 gatctcgttc cgtgatcgat g                                              1041

<210> SEQ ID NO 4
<211> LENGTH: 870
<212> TYPE: DNA
<213> ORGANISM: MUSA

<400> SEQUENCE: 4
gctgcatact aaggatctgt catctacaac taatcttgtg gaagatctga atcgaagacc       60
ttgagctcgg aaacaacttc caagatattg tgtctttcat ttctcagaaa gtatagggac      120
ttaaaaagta tgctcaacaa gccatattcc tttaatcttg ttgaggaatt ggattacatc      180
```

```
ttccttgcaa ttcctctcca tttgcatggc aattcggcag ctatttctta cttggttcta      240
tgagggaagg gaggttggtg aggacaattc ccatggaaat ttggcagcta cttccatacc      300
tacttcatta gaggagagag gttggtgggg ataatgacct gtgtggcagg cagtacaaca      360
actcacttgc gtttcttctc ctatacttaa atgacgacaa aatctttgat tgggttcaat      420
ttaattaaaa ttattgtttt atatgattta cacaaactaa ataacattac tagaagaaga      480
tgaaaagaaa gatgaatgct tatatgactc gagtgtgaca tgaacgtgga aatcaccttc      540
tactcgggag aagcaatcgt catatccgcg ggatcgtcct ggaaagagag agagagagag      600
agaggacgag gggatgagga aggaagaatt ggtgaggaaa acgatggcat gcatgcctct      660
tatctccacc cacccctctc ctcccctcca tctttgacga gaccgatcca gtggttgaag      720
tattatgccc acctaactct ctccatgcca ccacaagctg ctctatttaa cccttccttg      780
tgctcctctc tacctcaggg ttatctcacc ttccttacct tccacttcct cccttctggt      840
ctttcgtcgg atctcgttcc gtgatcgatg                                       870
```

```
<210> SEQ ID NO 5
<211> LENGTH: 16
<212> TYPE: DNA
<213> ORGANISM: ARTIFICIAL
<220> FEATURE:
<223> OTHER INFORMATION: primer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 5
scacntcstn gtntct                                                       16

<210> SEQ ID NO 6
<211> LENGTH: 16
<212> TYPE: DNA
<213> ORGANISM: ARTIFICIAL
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 6
ngtcgaswga nawgaa                                                       16

<210> SEQ ID NO 7
<211> LENGTH: 16
<212> TYPE: DNA
<213> ORGANISM: ARTIFICIAL
<220> FEATURE:
<223> OTHER INFORMATION: primer
<220> FEATURE:
<221> NAME/KEY: misc_feature
<222> LOCATION: (5)..(5)
<223> OTHER INFORMATION: n is a, c, g, or t
```

```
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 7
wgtgnagwan canaga                                                    16

<210> SEQ ID NO 8
<211> LENGTH: 10
<212> TYPE: DNA
<213> ORGANISM: ARTIFICIAL
<220> FEATURE:
<223> OTHER INFORMATION: primer

<400> SEQUENCE: 8
gagcttgaac                                                           10

<210> SEQ ID NO 9
<211> LENGTH: 10
<212> TYPE: DNA
<213> ORGANISM: ARTIFICIAL
<220> FEATURE:
<223> OTHER INFORMATION: primer

<400> SEQUENCE: 9
atctcgctag                                                           10

<210> SEQ ID NO 10
<211> LENGTH: 10
<212> TYPE: DNA
<213> ORGANISM: ARTIFICIAL
<220> FEATURE:
<223> OTHER INFORMATION: primer

<400> SEQUENCE: 10
ctgatccatg                                                           10

<210> SEQ ID NO 11
<211> LENGTH: 10
<212> TYPE: DNA
<213> ORGANISM: ARTIFICIAL
<220> FEATURE:
<223> OTHER INFORMATION: primer

<400> SEQUENCE: 11
tccactggca                                                           10

<210> SEQ ID NO 12
<211> LENGTH: 10
<212> TYPE: DNA
<213> ORGANISM: ARTIFICIAL
<220> FEATURE:
<223> OTHER INFORMATION: primer

<400> SEQUENCE: 12
ggtactccac                                                           10

<210> SEQ ID NO 13
<211> LENGTH: 17
<212> TYPE: DNA
<213> ORGANISM: ARTIFICIAL
```

```
<220> FEATURE:
<223> OTHER INFORMATION: primer

<400> SEQUENCE: 13
ttcccgatgg cggcgac                                                17

<210> SEQ ID NO 14
<211> LENGTH: 19
<212> TYPE: DNA
<213> ORGANISM: ARTIFICIAL
<220> FEATURE:
<223> OTHER INFORMATION: primer

<400> SEQUENCE: 14
gatggacttg gtggaggcg                                              19

<210> SEQ ID NO 15
<211> LENGTH: 21
<212> TYPE: DNA
<213> ORGANISM: ARTIFICIAL
<220> FEATURE:
<223> OTHER INFORMATION: primer

<400> SEQUENCE: 15
tcctgcttcg gcttctgcag t                                           21

<210> SEQ ID NO 16
<211> LENGTH: 18
<212> TYPE: DNA
<213> ORGANISM: ARTIFICIAL
<220> FEATURE:
<223> OTHER INFORMATION: primer

<400> SEQUENCE: 16
accctaaccg ccgagtgg                                               18

<210> SEQ ID NO 17
<211> LENGTH: 18
<212> TYPE: DNA
<213> ORGANISM: ARTIFICIAL
<220> FEATURE:
<223> OTHER INFORMATION: primer

<400> SEQUENCE: 17
ctgccgttcg catggacg                                               18

<210> SEQ ID NO 18
<211> LENGTH: 20
<212> TYPE: DNA
<213> ORGANISM: ARTIFICIAL
<220> FEATURE:
<223> OTHER INFORMATION: primer

<400> SEQUENCE: 18
cttcaaccac tggatcggtc                                             20

<210> SEQ ID NO 19
<211> LENGTH: 20
<212> TYPE: DNA
<213> ORGANISM: ARTIFICIAL
<220> FEATURE:
<223> OTHER INFORMATION: primer

<400> SEQUENCE: 19
cttctacaca gccatcggtc                                             20
```

```
<210> SEQ ID NO 20
<211> LENGTH: 21
<212> TYPE: DNA
<213> ORGANISM: ARTIFICIAL
<220> FEATURE:
<223> OTHER INFORMATION: primer

<400> SEQUENCE: 20
gacctgcctg aaaccgaact g                                          21

<210> SEQ ID NO 21
<211> LENGTH: 20
<212> TYPE: DNA
<213> ORGANISM: ARTIFICIAL
<220> FEATURE:
<223> OTHER INFORMATION: primer

<400> SEQUENCE: 21
tckytktcyt acattgcygg                                            20

<210> SEQ ID NO 22
<211> LENGTH: 20
<212> TYPE: DNA
<213> ORGANISM: ARTIFICIAL
<220> FEATURE:
<223> OTHER INFORMATION: primer

<400> SEQUENCE: 22
aagytgaagc aycaycchgg                                            20

<210> SEQ ID NO 23
<211> LENGTH: 20
<212> TYPE: DNA
<213> ORGANISM: ARTIFICIAL
<220> FEATURE:
<223> OTHER INFORMATION: primer

<400> SEQUENCE: 23
ttgaavccrt artccaagct                                            20

<210> SEQ ID NO 24
<211> LENGTH: 20
<212> TYPE: DNA
<213> ORGANISM: ARTIFICIAL
<220> FEATURE:
<223> OTHER INFORMATION: primer

<400> SEQUENCE: 24
gagttsacrt cytggttgtg                                            20

<210> SEQ ID NO 25
<211> LENGTH: 19
<212> TYPE: DNA
<213> ORGANISM: ARTIFICIAL
<220> FEATURE:
<223> OTHER INFORMATION: primer

<400> SEQUENCE: 25
tcacgagcaa gacccgctg                                             19

<210> SEQ ID NO 26
<211> LENGTH: 19
<212> TYPE: DNA
<213> ORGANISM: ARTIFICIAL
<220> FEATURE:
<223> OTHER INFORMATION: primer
```

```
<400> SEQUENCE: 26
gatggacttg gtggcggag                                            19

<210> SEQ ID NO 27
<211> LENGTH: 20
<212> TYPE: DNA
<213> ORGANISM: ARTIFICIAL
<220> FEATURE:
<223> OTHER INFORMATION: primer

<400> SEQUENCE: 27
gctccacgag caagacccac                                           20

<210> SEQ ID NO 28
<211> LENGTH: 17
<212> TYPE: DNA
<213> ORGANISM: ARTIFICIAL
<220> FEATURE:
<223> OTHER INFORMATION: primer

<400> SEQUENCE: 28
ttcccgatgg cggcgac                                              17

<210> SEQ ID NO 29
<211> LENGTH: 20
<212> TYPE: DNA
<213> ORGANISM: ARTIFICIAL
<220> FEATURE:
<223> OTHER INFORMATION: primer

<400> SEQUENCE: 29
ccacgaagtc catcgaacgt                                           20

<210> SEQ ID NO 30
<211> LENGTH: 20
<212> TYPE: DNA
<213> ORGANISM: ARTIFICIAL
<220> FEATURE:
<223> OTHER INFORMATION: primer

<400> SEQUENCE: 30
aaaggttcga ggggagccca                                           20

<210> SEQ ID NO 31
<211> LENGTH: 19
<212> TYPE: DNA
<213> ORGANISM: ARTIFICIAL
<220> FEATURE:
<223> OTHER INFORMATION: primer

<400> SEQUENCE: 31
cctcgacgga agctcgttt                                            19

<210> SEQ ID NO 32
<211> LENGTH: 19
<212> TYPE: DNA
<213> ORGANISM: ARTIFICIAL
<220> FEATURE:
<223> OTHER INFORMATION: primer

<400> SEQUENCE: 32
ggagaactgg gcgaacatc                                            19
```

```
<210> SEQ ID NO 33
<211> LENGTH: 409
<212> TYPE: DNA
<213> ORGANISM: Musa

<400> SEQUENCE: 33
ccagatcgag gccgccgcca tcatggagca catcctcgac ggcagctcct acatgaagat      60
ggccaagaag cttcacgagc aagacccgct gcagaagccg aagcaggacc ggtacgccct     120
ccgcacctcc ccgcagtggc tcggcccca gatcgaggtc atccgctccg ccaccaagtc     180
catcgagcgg gagatcaact ctgtcaacga caacccctc atcgacgtct ccaggaacaa     240
ggccctgcac ggcggcaact tccagggcac gcccatcggc gtgtccatgg acaacacccg     300
cctggccctc gccgccatcg ggaagctcat gttcgcgcag ttctcggagc tcgtcaacga     360
cttctacaac aacgggctgc cgtcgaacct ctccggcggg cgcaacccg              409

<210> SEQ ID NO 34
<211> LENGTH: 409
<212> TYPE: DNA
<213> ORGANISM: Musa

<400> SEQUENCE: 34
ccagatcgag gccgccgcta ttatggagca catcctcgac ggcagctcct acatgaagat      60
ggccaagaag cttccacgagc aagacccact gcagaagccg aagcaggacc gctacgccct    120
ccgcacctcc ccgcagtggc tcggcccca gatcgaggtc atccgcgcct ccaccaagtc     180
catcgagagg gagatcaact ccgtcaacga caacccctc atcgacgtct ccaggaacaa     240
ggccctccac ggcggcaact tccagggcac ccccatcggt gtgtcgatgg acaacacccg     300
cctggccgtc gctgccatcg ggaagctcat gttcgcgcag ttctccgagc tcgtcaacga     360
cttctacaac aacggcctgc cctcgaacct ctccggtggg cgcaaccc              409

<210> SEQ ID NO 35
<211> LENGTH: 409
<212> TYPE: DNA
<213> ORGANISM: Musa

<400> SEQUENCE: 35
ccaaatcgaa gccgccgcta tcatggagca cgtcctcgag ggcagctcct acatgaagat      60
ggcgaagaag cttccatgagc aagacccgct ccagaagcca aagcaggacc gctacgccct    120
ccgcacctca ccgcagtggc tcggcccca gatcgaagtc atccggtcgt ccacgaagtc     180
catcgaacgt gagatcaact cggtgaacga caacccctc attgacgtct cccggaacaa     240
ggccttgcac ggtggcaact tccagggac cccgatcggt gtctccatgg acaacacccg     300
cttagccatt gccgccatcg gcaaactcat gttcgcacag ttctcagagc tcgtcaacga     360
cttctacaac aatgggctcc cctcgaacct ttccggtgga agaaacccg              409

<210> SEQ ID NO 36
<211> LENGTH: 409
<212> TYPE: DNA
<213> ORGANISM: Musa

<400> SEQUENCE: 36
ccagatcgag gccgccgcca tcatggagca catcctcgac ggaagctcgt ttatgaagat      60
agcgaagaag ctccatgagc aagacccctt gcagaagccg aagcaggatc gctacgccct    120
gcgcacctcc ccgcagtggc tcggccctca gatcgaggtc atccgctcgt ccaccaagtc     180
```

```
catcgagcgg gagatcaact ccgtcaacga caaccccctc atcgacgtct ccaggaacaa      240
ggccctccac ggcggcaact tccagggcac acccatcggc gtgtccatgg acaacacccg      300
cctcgccctc gcggccatcg ggaagctgat gttcgcccag ttctccgagc tcgtcaacga      360
tttctataac aacggcctgc cgtcgaacct ctccggcggg cgcaccccg                  409
```

<210> SEQ ID NO 37
<211> LENGTH: 1663
<212> TYPE: DNA
<213> ORGANISM: Musa

<400> SEQUENCE: 37

```
gcttcctttg tttttgctag ttagatcctt atgccaaggc tcatgtgatt tggctgtcat       60
ggttggtggt gaagagcatt ccacaccaaa ctcccagtct cataaacaaa ggcttgcatt      120
caatttctc acccttgacc agaatttcca attttggttg gtggaaattt ccttcagaca       180
aaagaaaaac tattggccac aaggttaaat tgacagcaag tttggagcat gtctcatcaa      240
taaactgata ggtgtgtcca cttgactcaa atctttagtc ggtaaagatt ttgatagttt      300
atcgtaagac tctgaactca atctgtcttt gtaaaaaaa ataatataaa tattcattga       360
aacaaaaaat caagtatcaa aagattaagt taacgtctct caaacataag aattgtatgc      420
cgaggttcca cttaagtcat gttaagtatc taataattga accaaggaag gaaggagtgt      480
tgtttgttgt catgatagag gtaaaaagag tttatgatgt cataatactt gtattaacaa      540
ccattcatcc atgcatacca tctgaattaa gtggtaatcc tgtacaagat tgttcaagtg      600
gaatttgact gtcaaaagag taagctgcat actaaggatc tgtcatctac aactaatctt      660
gtggaagatc tgaatcgaag aacctgagct tggaaacaac tcccaagata ttgtgtcttt      720
catttctcag aaagtctagg gacttaaaag tatgttcaac aagccatatt cctttaatct      780
tgctgaggaa ttggattaca tcttccttgc aattcctctc catttgcatg gcaattcggc      840
agctatttct tacttggttc tatgagggaa gggagaaggg aggttggtga ggacaattcc      900
catggcaatt tggcagctac ttccataccT acttcattag aggagagagg ttggtgggga      960
caatgacctg tgtggcaggc agtagtacaa caactcactt gcgtttcttc tcctatactt     1020
aaatgacgac aaaatcttcg attgggttca atttaattaa aattattatt ttatatgatt     1080
tacacaaact aaatagttca ttctaataga aaactgtggg atcagaagcc acacacaaaa     1140
aaaaaaagac aaaactatag aatcgaactt atctttaatt tatatttttt atatctaaaa     1200
cattaatatg ataataatat acttactaga tacacatagt tgccatgatc aacattacta     1260
gaagaagatg aaaagaatga tgaatgctta tatgactcga gtatgacatg aacgtggaaa     1320
tcaccttcta ctcaggagaa gcaatcgtca tatccgcggg atcgtcctgg aaagagagag     1380
agagagagat agagagaaga cgaggggatg aggaaggaag aatggtgagg aaaacgatgg     1440
catgcatgcc tcatatctcc acccaccccT ctcctcccct ccatctttga cgggaccgat     1500
ccagtggttg aagtattatg cccacctaac tctctccatg ccaccacaag ctgctctatt     1560
taacccttcc ttgtgctcct ctctacctca gggttatctc accttcctta ccttccacct     1620
cctcccttct ggtctttcgt cggatctcgt tccgtgatcg atg                       1663
```

<210> SEQ ID NO 38
<211> LENGTH: 1041
<212> TYPE: DNA
<213> ORGANISM: Musa

<400> SEQUENCE: 38

```
agctgcatac taaggatctg tcatctacaa ctaatcttgt ggaagatctg aatcgaagaa      60
cctgagcttg gaaacaactc ccaagatatt gtgtctttca tttctcagaa agtctaggga     120
cttaaaagta tgttcaacaa gccatattcc tttaatcttg ctgaggaatt ggattacatc     180
ttccttgcaa ttcctctcca tttgcatggc aattcggcag ctatttctta cttggttcta     240
tgagggaagg gagaagggag gttggtgagg acaattccca tggcaatttg gcagctactt     300
ccatacctac ttcattagag gagagaggtt ggtggggaca atgacctgtg tggcaggcag     360
tagtacaaca actcacttgc gtttcttctc ctatacttaa atgacgacaa aatcttcgat     420
tgggttcaat ttaattaaaa ttattatttt atatgattta cacaaactaa atagttcatt     480
ctaatagaaa actgtgggat cagaagccac acacaaaaaa aaaagacaa aactatagaa      540
tcgaacttat ctttaattta tattttttat atctaaaaca ttaatatgat aataatatac     600
ttactagata cacatagttg ccatgatcaa cattactaga agaagatgaa agaatgatg      660
aatgcttata tgactcgagt atgacatgaa cgtggaaatc accttctact caggagaagc     720
aatcgtcata tccgcgggat cgtcctggaa agagagagag agagagatag agagaagacg     780
agggggatgag gaaggaagaa tggtgaggaa acgatggca tgcatgcctc atatctccac     840
ccacccctct cctcccctcc atctttgacg ggaccgatcc agtggttgaa gtattatgcc     900
cacctaactc tctccatgcc accacaagct gctctattta acccttcctt gtgctcctct     960
ctacctcagg gttatctcac cttccttacc ttccacctcc tcccttctgg tctttcgtcg    1020
gatctcgttc cgtgatcgat g                                              1041
```

<210> SEQ ID NO 39
<211> LENGTH: 869
<212> TYPE: DNA
<213> ORGANISM: Musa

<400> SEQUENCE: 39

```
agctgcatac taaggatctg tcatctacaa ctaatcttgt ggaagatctg aatcgaagac      60
cttgagctcg gaaacaactt ccaagatatt gtgtctttca tttctcagaa gtatagggac     120
ttaaaaagta tgctcacaag ccatattcct ttaatcttgt tgaggaattg gattacatct     180
tccttgcaat tcctctccat ttgcatggca attcggcagc tatttcttac ttggttctat     240
gagggaaggg aggttggtga ggacaattcc catggaaatt tggcagctac ttccatacct     300
acttcattag aggagagagg ttggtgggga taatgacctg tgtggcaggc agtacaacaa     360
ctcacttgcg tttcttctcc tatacttaaa tgacgacaaa atctttgatt gggttcaatt     420
taattaaaat tattgtttta tatgatttac acaaactaaa taacattact agaagaagat     480
gaaaagaaag atgaatgctt atatgactcg agtgtgacat gaacgtggaa atcaccttct     540
actcgggaga agcaatcgtc atatccgcgg gatcgtcctg gaaagagaga gagagagaga     600
gaggacgagg ggatgaggaa ggaagaattg tgaggaaaa cgatggcatg catgcctctt     660
atctccaccc accccctctcc tccccctccat cttttgacgag accgatccag tggttgaagt     720
attatgccca cctaactctc tccatgccac cacaagctgc tctatttaac ccttccttgt     780
gctcctctct acctcagggt tatctcacct tccttacctt ccacttcctc ccttctggtc     840
tttcgtcgga tctcgttccg tgatcgatg                                        869
```

```
<210> SEQ ID NO 40
<211> LENGTH: 1522
<212> TYPE: DNA
<213> ORGANISM: Musa

<400> SEQUENCE: 40
gcttcctttg tttttgctag ttagatcctt atgccaaagg ctcatgtgat ttggctgtca      60
tgtttggtgg tgaagagcat tccacaccaa actcccagtc tcataaacag aggctttcat     120
tcaattttct cacccttgac cagaatttcc aagcttggtt ggtggaaatt tccttcagac     180
aaaagaaaaa ctattggcca caaggttaaa ttgacagcaa gttcggagca tgtctcatca     240
ataaactgat aggtgtgtcc agttgactca aatctttagt cgataaagat tttgatagtt     300
tatcgtaaga ctctgaactc aaatctcgtc tttgtaaaaa aaaaaaaaat actataaata     360
ttcattgaaa caaaaaatca agtatcaaaa gattaacaat ttgatgacga aattaacgtt     420
tctcaaacat aagaattgta tgccgaggga ggttccactt aagtcatgtt aagtatctaa     480
taattgaacc aaggaaggaa ggaaggagtg ctgtttgttg tcatgataga ggtcaaaaga     540
gtttatgatg tcataatact tgtattaaca accattcatc catacatacc atctgaatta     600
agtggtaatc ctgtacaaga ttgttcaagt ggaatttgac tgtcaaaaga gtaagctgca     660
tactaaggat ctgtcatcta caactaatct tgtggaagat ctgaatcgaa gaccttgagc     720
tcggaaacaa cttccaagat attgtgtctt tcatttctca gaagtatagg gacttaaaaa     780
gtatgctcac aagccatatt cctttaatct tgttgaggaa ttggattaca tcttccttgc     840
aattcctctc catttgcatg gcaattcggc agctatttct tacttggttc tatgagggaa     900
gggaggttgg tgaggacaat tcccatggaa atttggcagc tacttccata cctacttcat     960
tagaggagag aggttggtgg ggataatgac ctgtgtggca ggcagtacaa caactcactt    1020
gcgtttcttc tcctatactt aaatgacgac aaaatctttg attgggttca atttaattaa    1080
aattattgtt ttatatgatt tacacaaact aaataacatt actagaagaa gatgaaaaga    1140
aagatgaatg cttatatgac tcgagtgtga catgaacgtg gaaatcacct tctactcggg    1200
agaagcaatc gtcatatccg cgggatcgtc ctggaaagag agagagagag agagaggacg    1260
aggggatgag gaaggaagaa ttggtgagga aaacgatggc atgcatgcct cttatctcca    1320
cccacccctc tcctcccctc catctttgac gagaccgatc cagtggttga agtattatgc    1380
ccacctaact ctctccatgc caccacaagc tgctctattt aaccctctcct tgtgctcctc    1440 tctacctcag ggttatctca ccttccttac cttccacttc ctcccttctg gtctttcgtc    1500
ggatctcgtt ccgtgatcga tg                                             1522
```